(12) United States Patent
Stanton et al.

(10) Patent No.: US 12,252,470 B2
(45) Date of Patent: Mar. 18, 2025

(54) LIPIDS AND NANOPARTICLE COMPOSITIONS THEREOF

(71) Applicant: Generation Bio Co., Cambridge, MA (US)

(72) Inventors: Matthew G. Stanton, Cambridge, MA (US); Birte Nolting, Cambridge, MA (US)

(73) Assignee: Generation Bio Co., Cambridge, MA (US)

( * ) Notice: Subject to any disclaimer, the term of this patent is extended or adjusted under 35 U.S.C. 154(b) by 0 days.

(21) Appl. No.: 18/644,728

(22) Filed: Apr. 24, 2024

(65) Prior Publication Data

US 2024/0294474 A1   Sep. 5, 2024

Related U.S. Application Data

(63) Continuation of application No. 17/913,498, filed as application No. PCT/US2021/024413 on Mar. 26, 2021.

(60) Provisional application No. 63/000,990, filed on Mar. 27, 2020.

(51) Int. Cl.
| | |
|---|---|
| *C12N 15/88* | (2006.01) |
| *A61K 9/51* | (2006.01) |
| *A61P 3/00* | (2006.01) |
| *C07D 211/22* | (2006.01) |

(52) U.S. Cl.
CPC .......... *C07D 211/22* (2013.01); *A61K 9/5123* (2013.01); *A61P 3/00* (2018.01); *C12N 15/88* (2013.01)

(58) Field of Classification Search
CPC ..... C07D 211/22; A61K 9/5123; C12N 15/88
See application file for complete search history.

(56) References Cited

U.S. PATENT DOCUMENTS

| | | | | |
|---|---|---|---|---|
| 2021/0023008 A1* | 1/2021 | Nakai | ................. | C12N 15/88 |
| 2023/0159459 A1* | 5/2023 | Stanton | ................. | C12N 15/88 514/317 |

FOREIGN PATENT DOCUMENTS

| | | |
|---|---|---|
| WO | 2012/123430 A1 | 9/2012 |
| WO | 2017/152149 A1 | 9/2017 |
| WO | WO-2019188867 A1 * | 10/2019 ............. A61K 47/22 |
| WO | 2021/046265 A1 | 3/2021 |
| WO | 2022/016089 A2 | 1/2022 |

OTHER PUBLICATIONS

Li et al., Production and characterization of novel recombinant adeno-associated virus replicative-form genomes: a eukaryotic source of DNA for gene transfer. PLoS One. Aug. 1, 2013;8(8):e69879, 14 pages.
Pubchem, Substance Record, SID 386915928. Nov. 2, 2019. <URL: https://pubchem.ncbi.nlm.nih.gov/substance/386915928>.
International Search Report and Written Opinion for Application No. PCT/US2021/024413, dated Oct. 21, 2021, 9 pages.

* cited by examiner

*Primary Examiner* — Amanda L. Aguirre
*Assistant Examiner* — Chris E Simmons
(74) *Attorney, Agent, or Firm* — McCarter & English, LLP; Marcie B. Clarke; Yelena Margolin

(57) ABSTRACT

Provided herein are lipids having the Formula (I):

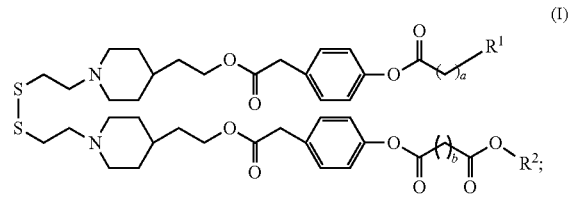

and pharmaceutically acceptable salts thereof, wherein $R^1$, $R^2$, a, and b are as defined herein. Also provided herein are lipid nanoparticle (LNP) compositions comprising lipid having the Formula (I) and a capsid-free, non-viral vector (e.g., ceDNA). In one aspect of any of the aspects or embodiments herein, these LNPs can be used to deliver a capsid-free, non-viral DNA vector to a target site of interest (e.g., cell, tissue, organ, and the like).

20 Claims, 5 Drawing Sheets

Specification includes a Sequence Listing.

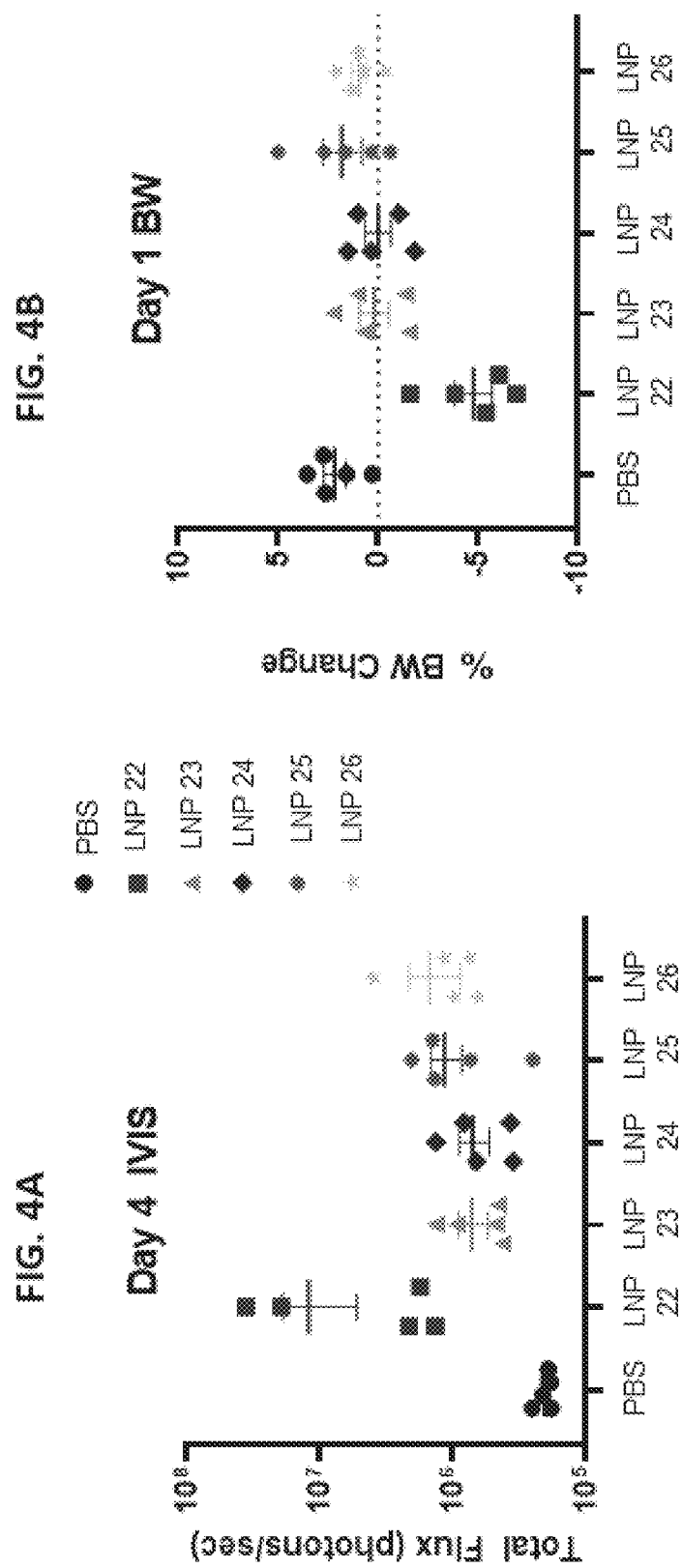
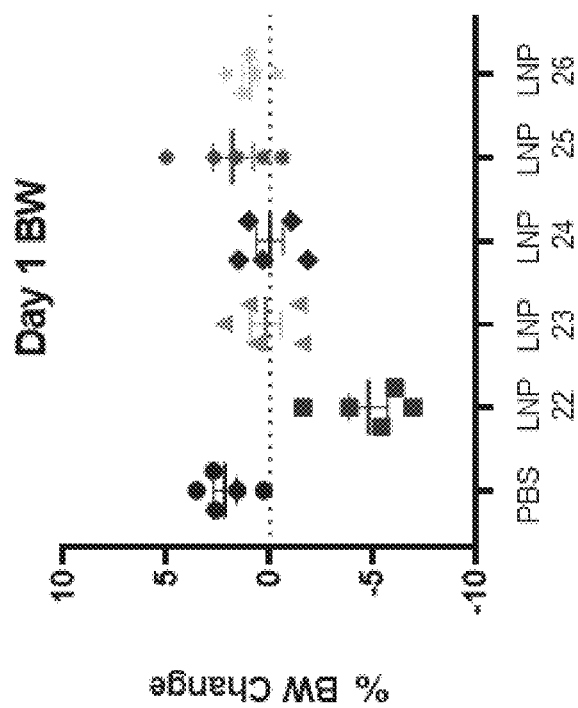
FIG. 4A
FIG. 4B

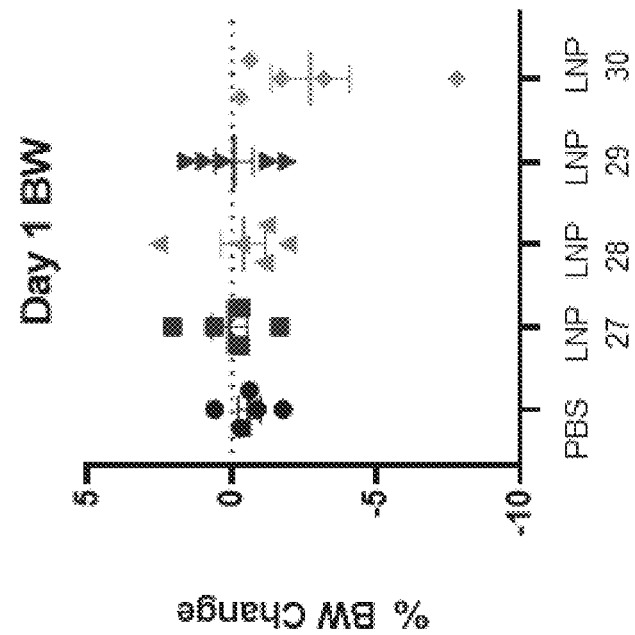
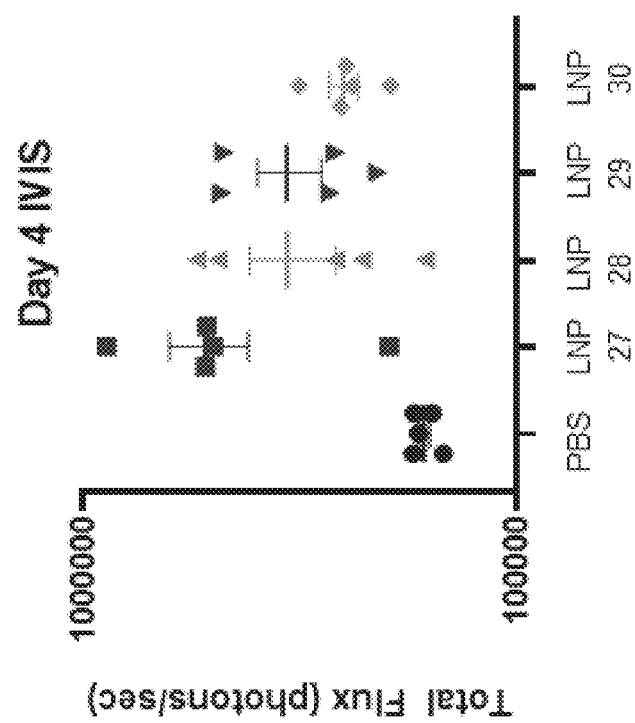
FIG. 5A
FIG. 5B

LIPIDS AND NANOPARTICLE COMPOSITIONS THEREOF

RELATED APPLICATIONS

This application is a continuation of U.S. application Ser. No. 17/913,498, filed on Sep. 22, 2022; which is a 35 U.S.C. § 371 national stage filing of International Application No. PCT/US2021/024413, filed on Mar. 26, 2021; which claims priority to U.S. Provisional Application No. 63/000,990, filed on Mar. 27, 2020. The entire contents of each of the foregoing applications are hereby incorporated herein by reference.

SEQUENCE LISTING

The instant application contains a Sequence Listing which has been filed electronically in XML format and is hereby incorporated by reference in its entirety. Said XML copy, created on Apr. 10, 2024, is named 131698-07703_SL.xml and is 1,729 bytes in size.

BACKGROUND

Gene therapy aims to improve clinical outcomes for patients suffering from either genetic disorders or acquired diseases caused by an aberrant gene expression profile. Various types of gene therapy that deliver therapeutic nucleic acids into a patient's cells as a drug to treat disease have been developed to date.

Delivery and expression of a corrective gene in the patient's target cells can be carried out via numerous methods, including the use of engineered viral gene delivery vectors, and potentially plasmids, minigenes, oligonucleotides, minicircles, or variety of closed-ended DNAs. Among the many virus-derived vectors available (e.g., recombinant retrovirus, recombinant lentivirus, recombinant adenovirus, and the like), recombinant adeno-associated virus (rAAV) is gaining acceptance as a versatile, as well as relatively reliable, vector in gene therapy. However, viral vectors, such as adeno-associated vectors, can be highly immunogenic and elicit humoral and cell-mediated immunity that can compromise efficacy, particularly with respect to re-administration.

Non-viral gene delivery circumvents certain disadvantages associated with viral transduction, particularly those due to the humoral and cellular immune responses to the viral structural proteins that form the vector particle, and any de novo virus gene expression. Among the non-viral gene delivery technologies is use of cationic lipids as a carrier. Ionizable lipids are roughly composed of an amine moiety and a lipid moiety, and the cationic amine moiety and a polyanion nucleic acid interact electrostatically to form a positively charged liposome or lipid membrane structure. Thus, uptake into cells is promoted and nucleic acids are delivered into cells.

Some widely used ionizable lipids are CLinDMA, DLinDMA (also known as DODAP), and cationic lipid such as DOTAP. Of note, these lipids have been employed for siRNA delivery to liver but suffer from non-optimal delivery efficiency along with liver toxicity at higher doses. In view of the shortcomings of the current cationic lipids, there is a need in the field to provide lipid scaffolds that not only demonstrate enhanced efficacy along with reduced toxicity, but with improved pharmacokinetics and intracellular kinetics such as cellular uptake and nucleic acid release from the lipid carrier.

SUMMARY

In one aspect, provided herein are ionizable lipids having the Formula (I):

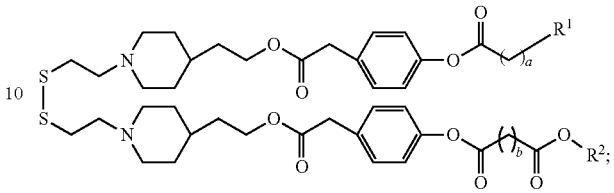

as well as pharmaceutically acceptable salts thereof, wherein $R^1$, $R^2$, a, and b are as defined herein.

Also provided are pharmaceutical compositions comprising a disclosed ionizable lipid, or a pharmaceutically acceptable salt thereof; and a pharmaceutically acceptable carrier.

Another aspect of the present disclosure relates to a composition comprising a lipid nanoparticle (LNP) comprising an ionizable lipid described herein, or a pharmaceutically acceptable salt thereof, and a nucleic acid. In one embodiment of any of the aspects or embodiments herein, the nucleic acid is encapsulated in the ionizable lipid. In a particular embodiment, the nucleic acid is a closed-ended DNA (ceDNA).

According to some embodiments of any of the aspects or embodiments herein, the LNP further comprises a sterol. According to some embodiments of any of the aspects or embodiments herein, the sterol can be a cholesterol, or beta-sitosterol.

According to some embodiments of any of the aspects or embodiments herein, the cholesterol is present at a molar percentage of about 20% to about 40%, for example about 20% to about 35%, about 20% to about 30%, about 20% to about 25%, about 25% to about 35%, about 25% to about 30%, or about 30% to about 35%, and the ionizable lipid is present at a molar percentage of about 80% to about 60%, for example about 80% to about 65%, about 80% to about 70%, about 80% to about 75%, about 75% to about 60%, about 75% to about 65%, about 75% to about 70%, about 70% to about 60%, or about 70% to about 60%. According to some embodiments of any of the aspects or embodiments herein, the cholesterol is present at a molar percentage of about 20% to about 40%, for example about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, or about 40%, and wherein the ionizable lipid is present at a molar percentage of about 80% to about 60%, for example about 80%, about 79%, about 78%, about 77%, about 76%, about 75%, about 74%, about 73%, about 72%, about 71%, about 70%, about 69%, about 68%, about 67%, about 66%, about 65%, about 64%, about 63%, about 62%, about 61%, or about 60%. According to some embodiments of any of the aspects or embodiments herein, the cholesterol is present at a molar percentage of about 40%, and wherein the ionizable lipid is present at a molar percentage of about 50%.

According to some embodiments of any of the aspects or embodiments herein, the composition further comprises a cholesterol, a PEG-lipid conjugate, and a non-cationic lipid. According to some embodiments of any of the aspects or embodiments herein, the PEG-lipid conjugate is present at about 1.5% to about 3%, for example about 1.5% to about 2.75%, about 1.5% to about 2.5%, about 1.5% to about 2.25%, about 1.5% to about 2%, about 2% to about 3%, about 2% to about 2.75%, about 2% to about 2.5%, about 2% to about 2.25%, about 2.25% to about 3%, about 2.25% to about 2.75%, or about 2.25% to about 2.5%. According to some embodiments of any of the aspects or embodiments herein, the PEG-lipid conjugate is present at about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, or about 3%. According to some embodiments of any of the aspects or embodiments herein, the cholesterol is present at a molar percentage of about 30% to about 50%, for example about 30% to about 45%, about 30% to about 40%, about 30% to about 35%, about 35% to about 50%, about 35% to about 45%, about 35% to about 40%, about 20% to about 40%, about 40% to about 50%, or about 45% to about 50%. According to some embodiments of any of the aspects or embodiments herein, the cholesterol is present at a molar percentage of about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50%.

According to some embodiments of any of the aspects or embodiments herein, the LNP further comprises a polyethylene glycol (PEG)-lipid. According to some embodiments of any of the aspects or embodiments herein, the PEG-lipid is 1-(monomethoxy-polyethyleneglycol)-2,3-dimyristoylglycerol (PEG-DMG). According to some embodiments of any of the aspects or embodiments herein, the LNP further comprises a non-cationic lipid. According to some embodiments of any of the aspects or embodiments herein, the non-cationic lipid is selected from the group consisting of distearoyl-sn-glycero-phosphoethanolamine, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), monomethyl-phosphatidylethanolamine (such as 16-O-monomethyl PE), dimethyl-phosphatidylethanolamine (such as 16-O-dimethyl PE), 18-1-trans PE, 1-stearoyl-2-oleoyl-phosphatidyethanolamine (SOPE), hydrogenated soy phosphatidylcholine (HSPC), egg phosphatidylcholine (EPC), dioleoylphosphatidylserine (DOPS), sphingomyelin (SM), dimyristoyl phosphatidylcholine (DMPC), dimyristoyl phosphatidylglycerol (DMPG), distearoylphosphatidylglycerol (DSPG), dierucoylphosphatidylcholine (DEPC), palmitoyloleyolphosphatidylglycerol (POPG), dielaidoyl-phosphatidylethanolamine (DEPE), 1,2-dilauroyl-sn-glycero-3-pho sphoethanolamine (DLPE); 1,2-diphytanoyl-sn-glycero-3-phosphoethanolamine (DPHyPE); lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidicacid, cerebrosides, dicetylphosphate, lysophosphatidylcholine, dilinoleoylphosphatidylcholine, or mixtures thereof. According to some embodiments of any of the aspects or embodiments herein, the non-cationic lipid is selected from the group consisting of dioleoylphosphatidylcholine (DOPC), distearoylphosphatidylcholine (DSPC), and dioleoyl-phosphatidylethanolamine (DOPE).

According to some embodiments of any of the aspects or embodiments herein, the PEG-lipid conjugate is present at about 1.5% to about 4%, for example about 1.5% to about 3%, about 2% to about 3%, about 2.5% to about 3%, about 1.5% to about 2.75%, about 1.5% to about 2.5%, about 1.5% to about 2.25%, about 1.5% to about 2%, about 1.5% to about 1.75%, about 2% to about 3%, about 2% to about 2.75%, about 2% to about 2.5%, about 2% to about 2.25%. According to some embodiments of any of the aspects or embodiments herein, the PEG-lipid conjugate is present at about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, or about 3%. According to some embodiments of any of the aspects or embodiments herein, the ionizable lipid is present at a molar percentage of about 42.5% to about 62.5%. According to some embodiments of any of the aspects or embodiments herein, the ionizable lipid is present at a molar percentage of about 42.5%, about 43%, about 43.5%, about 44%, about 44.5%, about 45%, about 45.5%, about 46%, about 46.5%, about 47%, about 47.5%, about 48%, about 48.5%, about 49%, about 49.5%, about 50%, about 50.5%, about 51%, 51.5%, about 52%, about 52.5%, about 53%, about 53.5%, about 54%, about 54.5%, about 55%, about 55.5%, about 56%, about 56.5%, about 57%, 57.5%, about 58%, about 58.5%, about 59%, about 59.5%, about 60%, about 60.5%, about 61%, about 61.5%, about 62%, or about 62.5%. According to some embodiments of any of the aspects or embodiments herein, the non-cationic lipid is present at a molar percentage of about 2.5% to about 12.5%. According to some embodiments of any of the aspects or embodiments herein, the cholesterol is present at a molar percentage of about 40%, the ionizable lipid is present at a molar percentage of about 52.5%, the non-cationic lipid is present at a molar percentage of about 7.5%, and wherein the PEG-lipid is present at about 3%.

According to some embodiments of any of the aspects or embodiments herein, the LNP composition further comprises dexamethasone palmitate.

According to some embodiments of any of the aspects or embodiments herein, the LNP is in size ranging from about 50 nm to about 110 nm in diameter, for example about 50 nm to about 100 nm, about 50 nm to about 95 nm, about 50 nm to about 90 nm, about 50 nm to about 85 nm, about 50 nm to about 80 nm, about 50 nm to about 75 nm, about 50 nm to about 70 nm, about 50 nm to about 65 nm, about 50 nm to about 60 nm, about 50 nm to about 55 nm, about 60 nm to about 110 nm, about 60 nm to about 100 nm, about 60 nm to about 95 nm, about 60 nm to about 90 nm, about 60 nm to about 85 nm, about 60 nm to about 80 nm, about 60 nm to about 75 nm, about 60 nm to about 70 nm, about 60 nm to about 65 nm, about 70 nm to about 110 nm, about 70 nm to about 100 nm, about 70 nm to about 95 nm, about 70 nm to about 90 nm, about 70 nm to about 85 nm, about 70 nm to about 80 nm, about 70 nm to about 75 nm, about 80 nm to about 110 nm, about 80 nm to about 100 nm, about 80 nm to about 95 nm, about 80 nm to about 90 nm, about 80 nm to about 85 nm, about 90 nm to about 110 nm, or about 90 nm to about 100 nm. According to some embodiments of any of the aspects or embodiments herein, the LNP is less than about 100 nm in size, for example less than about 105 nm, less than about 100 nm, less than about 95 nm, less than about 90 nm, less than about 85 nm, less than about 80 nm, less than about 75 nm, less than about 70 nm, less than about 65 nm, less than about 60 nm, less than about 55 nm, less than about 50 nm, less than about 45 nm, less than about 40 nm, less than about 35 nm, less than about 30 nm, less than about 25 nm, less than about 20 nm, less than about 15 nm, or less than about 10 nm in size. According to some embodiments of any of the aspects or embodiments herein, the LNP is less than about 70 nm in size, for example less than about 65 nm, less than about 60 nm, less than about 55 nm, less than about 50 nm, less than about 45 nm, less than about 40 nm, less than about 35 nm, less than about 30 nm, less than about 25 nm, less than about 20 nm, less than about 15 nm, or less than about 10 nm in size. According to some embodiments, the LNP is less than about 60 nm in size, for example less than about 55 nm, less than about 50 nm, less than about 45 nm, less than about 40 nm, less than about 35 nm, less than about 30 nm, less than about 25 nm, less than about 20 nm, less than about 15 nm, or less than about 10 nm in size.

According to some embodiments of any of the aspects or embodiments herein, the LNP composition has a total lipid to nucleic acid ratio of about 10:1. According to some embodiments of any of the aspects or embodiments herein, the LNP composition has a total lipid to nucleic acid ratio of about 20:1. According to some embodiments of any of the aspects or embodiments herein, the composition has a total lipid to nucleic acid ratio of about 30:1. According to some embodiments of any of the aspects or embodiments herein, the composition has a total lipid to nucleic acid ratio of about 40:1. According to some embodiments of any of the aspects or embodiments herein, the composition has a total lipid to nucleic acid ratio of about 50:1.

According to some embodiments of any of the aspects or embodiments herein, the LNP further comprises a tissue targeting moiety. The tissue targeting moiety can be a peptide, oligosaccharide or the like, which can be used for the delivery of the LNP to one or more specific tissues such as cancer, the liver, the CNS, or the muscle. According to some embodiments of any of the aspects or embodiments herein, the tissue targeting moiety is linked to the PEG-lipid conjugate. According to some embodiments of any of the aspects or embodiments herein, the tissue targeting moiety is a ligand for liver specific receptors. According to some embodiments of any of the aspects or embodiments herein, the ligand of liver specific receptors used for liver targeting is an oligosaccharide such as N-Acetylgalactosamine (GalNAc).

According to some embodiments of any of the aspects or embodiments herein, the GalNAc-linked GalNAc-linked PEG-lipid conjugate is present in the lipid nanoparticle at a molar percentage of 1.5%, 1.4%, 1.3%, 1.2%, 1.1%, 1.0%, 0.9%, 0.8%, 0.7%, 0.6%, 0.5%, 0.4%, 0.3%, 0.2%, or 0.1%. According to some embodiments of any of the aspects or embodiments herein, the GalNAc-linked PEG-lipid conjugate is present in the LNP at a molar percentage of 0.2%. According to some embodiments of any of the aspects or embodiments herein, the GalNAc-linked PEG-lipid conjugate is present in the LNP at a molar percentage of 0.3%. According to some embodiments of any of the aspects or embodiments herein, the GalNAc-linked PEG-lipid conjugate is present in the LNP at a molar percentage of 0.4%. According to some embodiments of any of the aspects or embodiments herein, the GalNAc-linked PEG-lipid conjugate is present in the LNP at a molar percentage of 0.5%. According to some embodiments of any of the aspects or embodiments herein, the GalNAc-linked PEG-lipid conjugate is present in the LNP at a molar percentage of 0.6%. According to some embodiments of any of the aspects or embodiments herein, the GalNAc-linked PEG-lipid conjugate is present in the LNP at a molar percentage of 0.7%. According to some embodiments of any of the aspects or embodiments herein, GalNAc-linked PEG-lipid conjugate is present in the LNP at a molar percentage of 0.8%. According to some embodiments of any of the aspects or embodiments herein, the GalNAc-linked PEG-lipid conjugate is present in the LNP at a molar percentage of 0.9%. According to some embodiments of any of the aspects or embodiments herein, the GalNAc-linked PEG-lipid conjugate is present in the LNP at a molar percentage of 1.0%. According to some embodiments of any of the aspects or embodiments herein, the GalNAc-linked PEG-lipid conjugate is present in the LNP at a molar percentage of about 1.5%. According to some embodiments of any of the aspects or embodiments herein, the GalNAc-linked PEG-lipid conjugate is present in the LNP at a molar percentage of 2.0%.

According to some embodiments of any of the aspects or embodiments herein, the LNP composition is prepared in a buffer such as malic acid. In some embodiments of any of the aspects and embodiments herein, the composition is prepared in about 10 mM to about 30 mM malic acid, for example about 10 mM to about 25 mM, about 10 mM to about 20 mM, about 10 mM to about 15 mM, about 15 mM to about 25 mM, about 15 mM to about 20 mM, about 20 mM to about 25 mM. According to some embodiments of any of the aspects or embodiments herein, the composition is prepared in about 10 mM malic acid, about 11 mM malic acid, about 12 mM malic acid, about 13 mM malic acid, about 14 mM malic acid, about 15 mM malic acid, about 16 mM malic acid, about 17 mM malic acid, about 18 mM malic acid, about 19 mM malic acid, about 20 mM malic acid, about 21 mM malic acid, about 22 mM malic acid, about 23 mM malic acid, about 24 mM malic acid, about 25 mM malic acid, about 26 mM malic acid, about 27 mM malic acid, about 28 mM malic acid, about 29 mM malic acid, or about 30 mM malic acid. According to some embodiments of any of the aspects or embodiments herein, the composition comprises about 20 mM malic acid.

According to some embodiments of any of the aspects or embodiments herein, the LNP composition is prepared in a solution having about 30 mM to about 50 mM NaCl, for example about 30 mM to about 45 mM NaCl, about 30 mM to about 40 mM NaCl, about 30 mM to about 35 mM NaCl, about 35 mM to about 45 mM NaCl, about 35 mM to about 40 mM NaCl, or about 40 mM to about 45 mM NaCl. According to some embodiments of any of the aspects or embodiments herein, the LNP composition is prepared in a solution having about 30 mM NaCl, about 35 mM NaCl, about 40 mM NaCl, or about 45 mM NaCl. According to some embodiments of any of the aspects or embodiments herein, the LNP composition is prepared in a solution having about 40 mM NaCl.

According to some embodiments of any of the aspects or embodiments herein, the LNP composition is prepared in a solution having about 20 mM to about 100 mM $MgCl_2$, for example about 20 mM to about 90 mM $MgCl_2$, about 20 mM to about 80 mM $MgCl_2$, about 20 mM to about 70 mM $MgCl_2$, about 20 mM to about 60 mM $MgCl_2$, about 20 mM to about 50 mM $MgCl_2$, about 20 mM to about 40 mM $MgCl_2$, about 20 mM to about 30 mM $MgCl_2$, about 320 mM to about 90 mM $MgCl_2$, about 30 mM to about 80 mM $MgCl_2$, about 30 mM to about 70 mM $MgCl_2$, about 30 mM to about 60 mM $MgCl_2$, about 30 mM to about 50 mM $MgCl_2$, about 30 mM to about 40 mM $MgCl_2$, about 40 mM to about 90 mM $MgCl_2$, about 40 mM to about 80 mM $MgCl_2$, about 40 mM to about 70 mM $MgCl_2$, about 40 mM to about 60 mM $MgCl_2$, about 40 mM to about 50 mM MgCl$_2$, about 50 mM to about 90 mM MgCl$_2$, about 50 mM to about 80 mM MgCl$_2$, about 50 mM to about 70 mM MgCl$_2$, about 50 mM to about 60 mM MgCl$_2$, about 60 mM to about 90 mM MgCl$_2$, about 60 mM to about 80 mM MgCl$_2$, about 60 mM to about 70 mM MgCl$_2$, about 70 mM to about 90 mM MgCl$_2$, about 70 mM to about 80 mM MgCl$_2$, or about 80 mM to about 90 mM MgCl$_2$.

According to some embodiments of any of the aspects or embodiments herein, the ceDNA is closed-ended linear duplex DNA. According to some embodiments of any of the aspects or embodiments herein, the ceDNA comprises an expression cassette comprising a promoter sequence and a transgene.

According to some embodiments of any of the aspects or embodiments herein, the ceDNA comprises expression cassette comprising a polyadenylation sequence.

According to some embodiments of any of the aspects or embodiments herein, the ceDNA comprises at least one inverted terminal repeat (ITR) flanking either 5' or 3' end of said expression cassette. According to some embodiments of any of the aspects or embodiments herein, the expression cassette is flanked by two ITRs, wherein the two ITRs comprise one 5' ITR and one 3' ITR. According to some embodiments of any of the aspects or embodiments herein, the expression cassette is connected to an ITR at 3' end (3' ITR). According to some embodiments of any of the aspects or embodiments herein, the expression cassette is connected to an ITR at 5' end (5' ITR). According to some embodiments of any of the aspects or embodiments herein, at least one of 5' ITR and 3' ITR is a wild-type AAV ITR. According to some embodiments of any of the aspects or embodiments herein, at least one of 5' ITR and 3' ITR is a modified ITR. According to some embodiments of any of the aspects or embodiments herein, the ceDNA further comprises a spacer sequence between a 5' ITR and the expression cassette.

According to some embodiments of any of the aspects or embodiments herein, the ceDNA further comprises a spacer sequence between a 3' ITR and the expression cassette. According to some embodiments of any of the aspects or embodiments herein, the spacer sequence is at least 5 base pairs long in length. According to some embodiments of any of the aspects or embodiments herein, the spacer sequence is 5 to 100 base pairs long in length. According to some embodiments of any of the aspects or embodiments herein, the spacer sequence is 5, 10, 15, 20, 25, 30, 35, 40, 45, 50, 55, 60, 65, 70, 75, 80, 85, 90, 95 or 100 base pairs long in length. According to some embodiments of any of the aspects or embodiments herein, the spacer sequence is 5 to 500 base pairs long in length. According to some embodiments of any of the aspects or embodiments herein, the spacer sequence is 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, or 495 base pairs long in length.

According to some embodiments of any of the aspects or embodiments herein, the ceDNA has a nick or a gap.

According to some embodiments of any of the aspects or embodiments herein, the ITR is an ITR derived from an AAV serotype, derived from an ITR of goose virus, derived from a B19 virus ITR, a wild-type ITR from a parvovirus. According to some embodiments of any of the aspects or embodiments herein, the AAV serotype is selected from the group comprising of AAV1, AAV2, AAV3, AAV4, AAV5, AAV6, AAV7, AAV8, AAV9, AAV10, AAV11 and AAV12.

According to some embodiments of any of the aspects or embodiments herein, the ITR is a mutant ITR, and the ceDNA optionally comprises an additional ITR which differs from the first ITR. According to some embodiments of any of the aspects or embodiments herein, the ceDNA comprises two mutant ITRs in both 5' and 3' ends of the expression cassette, optionally wherein the two mutant ITRs are symmetric mutants. According to some embodiments of any of the aspects or embodiments herein, the ceDNA is a CELiD, DNA-based minicircle, a MIDGE, a ministering DNA, a dumbbell shaped linear duplex closed-ended DNA comprising two hairpin structures of ITRs in the 5' and 3' ends of an expression cassette, or a Doggybone™ DNA. According to some embodiments of any of the aspects or embodiments herein, the pharmaceutical composition further comprises a pharmaceutically acceptable excipient.

According to some aspects, the disclosure provides a method of treating a genetic disorder in a subject, the method comprising administering to the subject an effective amount of the pharmaceutical composition according to any of the aspects or embodiments herein. According to some embodiments of any of the aspects or embodiments herein, the subject is a human. According to some embodiments of any of the aspects or embodiments herein, the genetic disorder is selected from the group consisting of sickle-cell anemia, melanoma, hemophilia A (clotting factor VIII (FVIII) deficiency) and hemophilia B (clotting factor IX (FIX) deficiency), cystic fibrosis (CFTR), familial hypercholesterolemia (LDL receptor defect), hepatoblastoma, Wilson disease, phenylketonuria (PKU), congenital hepatic porphyria, inherited disorders of hepatic metabolism, Lesch Nyhan syndrome, sickle cell anemia, thalassemia, xeroderma pigmentosum, Fanconi's anemia, retinitis pigmentosa, ataxia telangiectasia, Bloom's syndrome, retinoblastoma, mucopolysaccharide storage diseases (e.g., Hurler syndrome (MPS Type I), Scheie syndrome (MPS Type I S), Hurler-Scheie syndrome (MPS Type I H-S), Hunter syndrome (MPS Type II), Sanfilippo Types A, B, C, and D (MPS Types III A, B, C, and D), Morquio Types A and B (MPS IVA and MPS IVB), Maroteaux-Lamy syndrome (MPS Type VI), Sly syndrome (MPS Type VII), hyaluronidase deficiency (MPS Type IX)), Niemann-Pick Disease Types A/B, C1 and C2, Fabry disease, Schindler disease, GM2-gangliosidosis Type II (Sandhoff Disease), Tay-Sachs disease, Metachromatic Leukodystrophy, Krabbe disease, Mucolipidosis Type I, II/III and IV, Sialidosis Types I and II, Glycogen Storage disease Types I and II (Pompe disease), Gaucher disease Types I, II and III, Fabry disease, cystinosis, Batten disease, Aspartylglucosaminuria, Salla disease, Danon disease (LAMP-2 deficiency), Lysosomal Acid Lipase (LAL) deficiency, neuronal ceroid lipofuscinoses (CLN1-8, INCL, and LINCL), sphingolipidoses, galactosialidosis, amyotrophic lateral sclerosis (ALS), Parkinson's disease, Alzheimer's disease, Huntington's disease, spinocerebellar ataxia, spinal muscular atrophy, Friedreich's ataxia, Duchenne muscular dystrophy (DMD), Becker muscular dystrophies (BMD), dystrophic epidermolysis bullosa (DEB), ectonucleotide pyrophosphatase 1 deficiency, generalized arterial calcification of infancy (GACI), Leber Congenital Amaurosis, Stargardt macular dystrophy (ABCA4), ornithine transcarbamylase (OTC) deficiency, Usher syndrome, alpha-1 antitrypsin deficiency, progressive familial intrahepatic cholestasis (PFIC) type I (ATP8B1 deficiency), type II (ABCB11), type III (ABCB4), or type IV (TJP2) and Cathepsin A deficiency. According to some embodiments of any of the aspects or embodiments herein, the genetic disorder is Leber congenital amaurosis (LCA). According to some embodiments of any of the aspects or embodiments herein, the LCA is LCA10. According to some embodiments of any of the aspects or embodiments herein, the genetic disorder is Niemann-Pick disease. According to some embodiments of any of the aspects or embodiments herein, the genetic disorder is Stargardt macular dystrophy. According to some embodiments of any of the aspects or embodiments herein, the genetic disorder is glucose-6-phosphatase (G6Pase) deficiency (glycogen storage disease type I) or Pompe disease (glycogen storage disease type II). According to some embodiments of any of the aspects or embodiments herein, the genetic disorder is hemophilia A (Factor VIII deficiency). According to some embodiments of any of the aspects or embodiments herein, the genetic disorder is hemophilia B (Factor IX deficiency). According to some embodiments of any of the aspects or embodiments herein, the genetic disorder is hunter syndrome (Mucopolysaccharidosis II). According to some embodiments of any of the aspects or embodiments herein, the genetic disorder is cystic fibrosis. According to some embodiments of any of the aspects or embodiments herein, the genetic disorder is dystrophic epidermolysis bullosa (DEB). According to some embodiments of any of the aspects or embodiments herein, the genetic disorder is phenylketonuria (PKU). According to some embodiments of any of the aspects or embodiments herein, the genetic disorder is progressive familial intrahepatic cholestasis (PFIC). According to some embodiments of any of the aspects or embodiments herein, the genetic disorder is Wilson disease. According to some embodiments of any of the aspects or embodiments herein, the genetic disorder is Gaucher disease Type I, II or III. According to some embodiments of any of the aspects or embodiments herein, the genetic disorder is age related macular degeneration. According to some embodiments of any of the aspects or embodiments herein, the genetic disorder is ornithine transcarbamylase deficiency. According to some embodiments of any of the aspects or embodiments herein, the genetic disorder is retinitis pigmentosa (RP1). According to some embodiments of any of the aspects or embodiments herein, the genetic disorder is Usher syndrome. According to some embodiments of any of the aspects or embodiments herein, the genetic disorder is Lysosomal Acid Lipase (LAL) deficiency.

BRIEF DESCRIPTION OF THE DRAWINGS

Embodiments of the present disclosure, briefly summarized above and discussed in greater detail below, can be understood by reference to the illustrative embodiments of the disclosure depicted in the appended drawings. However, the appended drawings illustrate only typical embodiments of the disclosure and are therefore not to be considered limiting of scope, for the disclosure may admit to other equally effective embodiments.

FIG. 4A shows the improvements in ceDNA-luc expression achieved by employing disclosed lipid nanoparticles (e.g., LNP 24 comprising Lipid 6, LNP 25 comprising Lipid 7, and LNP 26 comprising Lipid 8) compared to SS-OP (i.e., LNP 23), as observed in Study D. FIG. 4B shows the improvements in tolerability (as measured by change in body weight) in mice by employing disclosed lipid nanoparticles (e.g., LNP 24 comprising Lipid 6, LNP 25 comprising Lipid 7, and LNP 26 comprising Lipid 8) compared to Ionizable Lipid A (i.e., LNP 22) being used as control.

FIG. 5A shows the improvements in ceDNA-luc expression achieved by employing disclosed lipid nanoparticles (e.g., LNP 28 comprising Lipid 9 and LNP 29 comprising Lipid 10) compared to SS-OP (i.e., LNP 27). FIG. 5B shows that the improvements in ceDNA-luc expression as depicted in FIG. 5A did not compromise the tolerability of the disclosed lipid nanoparticles in mice.

DETAILED DESCRIPTION

Figure 1:
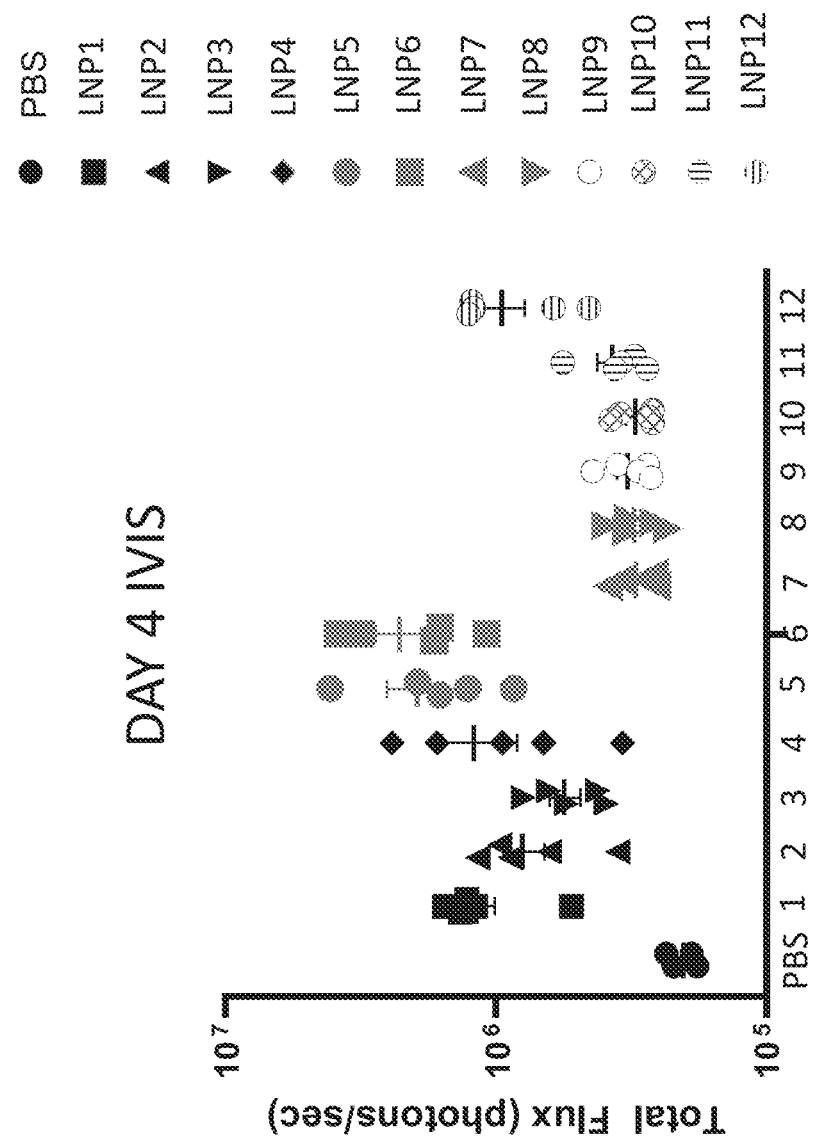
FIG. 1 shows the improvements in ceDNA-luc expression achieved by employing disclosed lipid nanoparticles (e.g., LNP 5 comprising Lipid 1 and LNP 6 comprising Lipid 3) compared to SS-OP (e.g., LNPs 1, 2, and 7-12) as observed in Study A.

The present disclosure provides a lipid-based platform for delivering therapeutic nucleic acid (TNA) such as viral or non-viral vectors (e.g., closed-ended DNA), which can move from the cytoplasm of the cell into the nucleus, and maintain high levels of expression. For example, the immunogenicity associated with viral vector-based gene therapies has limited the number of patients who can be treated due to pre-existing background immunity, as well as prevented the re-dosing of patients either to titrate to effective levels in each patient, or to maintain effects over the longer term. Furthermore, other nucleic acid modalities greatly suffer from immunogenicity due to an innate DNA or RNA sensing mechanism that triggers a cascade of immune responses. Because of the lack of pre-existing immunity, the presently described TNA lipid particles (e.g., lipid nanoparticles) allow for additional doses of TNA, such as mRNA, siRNA or ceDNA as necessary, and further expands patient access, including into pediatric populations who may require a subsequent dose upon tissue growth. Moreover, it is a finding of the present disclosure that the TNA lipid particles (e.g., lipid nanoparticles), comprising in particular lipid compositions comprising one or more tertiary amino groups, and a disulfide bond provide more efficient delivery of the TNA (e.g., ceDNA), better tolerability and an improved safety profile. Because the presently described TNA lipid particles (e.g., lipid nanoparticles) have no packaging constraints imposed by the space within the viral capsid, in theory, the only size limitation of the TNA lipid particles (e.g., lipid nanoparticles) resides in the expression (e.g., DNA replication, or RNA translation) efficiency of the host cell.

One of the biggest hurdles in the development of therapeutics, particularly in rare diseases, is the large number of individual conditions. Around 350 million people on earth are living with rare disorders, defined by the National Institutes of Health as a disorder or condition with fewer than 200,000 people diagnosed. About 80 percent of these rare disorders are genetic in origin, and about 95 percent of them do not have treatment approved by the FDA (rarediseases.info.nih.gov/diseases/pages/31/faqs-about-rare-diseases). Among the advantages of the TNA lipid particles (e.g., lipid nanoparticles) described herein is in providing an approach that can be rapidly adapted to multiple diseases that can be treated with a specific modality of TNA, and particularly to rare monogenic diseases that can meaningfully change the current state of treatments for many of the genetic disorder or diseases.

I. Definitions

The term "alkyl" refers to a monovalent saturated, straight- (i.e., unbranched-) or branched-chain hydrocarbon radical. Exemplary alkyl groups include, but are not limited to, ethyl, propyl, isopropyl, 2-methyl-1-butyl, 3-methyl-2-butyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, nonyl, decanyl, undecanyl, dodecanyl, tridecanyl, tetradecanyl, pentadecanyl, hexadecanyl, heptadecanyl, octadecanyl, nonadecanyl, eicosanyl, etc.

The term "alkenyl" refers to straight or branched aliphatic hydrocarbon radical with one or more (e.g., one or two) carbon-carbon double bonds, wherein the alkenyl radical includes radicals having "cis" and "trans" orientations, or by an alternative nomenclature, "E" and "Z" orientations.

The term "pharmaceutically acceptable salt" as used herein refers to pharmaceutically acceptable organic or inorganic salts of an ionizable lipid of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

As used in this specification and the appended claims, the term "about," when referring to a measurable value such as an amount, a temporal duration, and the like, is meant to encompass variations of ±20% or ±10%, more preferably ±5%, even more preferably ±1%, even more preferably ±0.5%, and still more preferably ±0.1% from the specified value, as such variations are appropriate to perform the disclosed methods.

As used herein, "comprise," "comprising," and "comprises" and "comprised of" are meant to be synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The term "consisting of" refers to compositions, methods, processes, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

As used herein the terms, "administration," "administering" and variants thereof refers to introducing a composition or agent (e.g., nucleic acids, in particular ceDNA) into a subject and includes concurrent and sequential introduction of one or more compositions or agents. "Administration" can refer, e.g., to therapeutic, pharmacokinetic, diagnostic, research, placebo, and experimental methods. "Administration" also encompasses in vitro and ex vivo treatments. The introduction of a composition or agent into a subject is by any suitable route, including orally, pulmonarily, intranasally, parenterally (intravenously, intramuscularly, intraperitoneally, or subcutaneously), rectally, intralymphatically, intratumorally, or topically. Administration includes self-administration and the administration by another. Administration can be carried out by any suitable route. A suitable route of administration allows the composition or the agent to perform its intended function. For example, if a suitable route is intravenous, the composition is administered by introducing the composition or agent into a vein of the subject. In one aspect of any of the aspects or embodiments herein, "administration" refers to therapeutic administration.

As used herein, the phrase "anti-therapeutic nucleic acid immune response", "anti-transfer vector immune response", "immune response against a therapeutic nucleic acid", "immune response against a transfer vector", or the like is meant to refer to any undesired immune response against a therapeutic nucleic acid, viral or non-viral in its origin. In some embodiments of any of the aspects and embodiments herein, the undesired immune response is an antigen-specific immune response against the viral transfer vector itself. In some embodiments of any of the aspects and embodiments herein, the immune response is specific to the transfer vector which can be double stranded DNA, single stranded RNA, or double stranded RNA. In other embodiments, the immune response is specific to a sequence of the transfer vector. In other embodiments, the immune response is specific to the CpG content of the transfer vector.

As used herein, the terms "carrier" and "excipient" are meant to include any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutically active substances is well known in the art. Supplementary active ingredients can also be incorporated into the compositions. The phrase "pharmaceutically-acceptable" refers to molecular entities and compositions that do not produce a toxic, an allergic, or similar untoward reaction when administered to a host.

As used herein, the term "ceDNA" is meant to refer to capsid-free closed-ended linear double stranded (ds) duplex DNA for non-viral gene transfer, synthetic or otherwise. Detailed description of ceDNA is described in International application of PCT/US2017/020828, filed Mar. 3, 2017, the entire contents of which are expressly incorporated herein by reference. Certain methods for the production of ceDNA comprising various inverted terminal repeat (ITR) sequences and configurations using cell-based methods are described in Example 1 of International applications PCT/US18/49996, filed Sep. 7, 2018, and PCT/US2018/064242, filed Dec. 6, 2018 each of which is incorporated herein in its entirety by reference. Certain methods for the production of synthetic ceDNA vectors comprising various ITR sequences and configurations are described, e.g., in International application PCT/US2019/14122, filed Jan. 18, 2019, the entire content of which is incorporated herein by reference. As used herein, the terms "ceDNA vector" and "ceDNA" are used interchangeably. According to some embodiments of any of the aspects or embodiments herein, the ceDNA is a closed-ended linear duplex (CELiD) CELiD DNA. According to some embodiments of any of the aspects or embodiments herein, the ceDNA is a DNA-based minicircle. According to some embodiments of any of the aspects or embodiments herein, the ceDNA is a minimalistic immunological-defined gene expression (MIDGE)-vector. According to some embodiments of any of the aspects or embodiments herein, the ceDNA is a ministering DNA. According to some embodiments of any of the aspects or embodiments herein, the ceDNA is a dumbbell shaped linear duplex closed-ended DNA comprising two hairpin structures of ITRs in the 5' and 3' ends of an expression cassette. According to some embodiments of any of the aspects or embodiments herein, the ceDNA is a Doggybone™ DNA.

As used herein, the term "ceDNA-bacmid" is meant to refer to an infectious baculovirus genome comprising a ceDNA genome as an intermolecular duplex that is capable of propagating in *E. coli* as a plasmid, and so can operate as a shuttle vector for baculovirus.

As used herein, the term "ceDNA-baculovirus" is meant to refer to a baculovirus that comprises a ceDNA genome as an intermolecular duplex within the baculovirus genome.

As used herein, the terms "ceDNA-baculovirus infected insect cell" and "ceDNA-BIIC" are used interchangeably, and are meant to refer to an invertebrate host cell (including, but not limited to an insect cell (e.g., an Sf9 cell)) infected with a ceDNA-baculovirus.

As used herein, the term "ceDNA genome" is meant to refer to an expression cassette that further incorporates at least one inverted terminal repeat region. A ceDNA genome may further comprise one or more spacer regions. In some embodiments of any of the aspects and embodiments herein the ceDNA genome is incorporated as an intermolecular duplex polynucleotide of DNA into a plasmid or viral genome.

As used herein, the terms "DNA regulatory sequences," "control elements," and "regulatory elements," are used interchangeably herein, and are meant to refer to transcriptional and translational control sequences, such as promoters, enhancers, polyadenylation signals, terminators, protein degradation signals, and the like, that provide for and/or regulate transcription of a non-coding sequence (e.g., DNA-targeting RNA) or a coding sequence (e.g., site-directed modifying polypeptide, or Cas9/Csn1 polypeptide) and/or regulate translation of an encoded polypeptide.

As used herein, the term "exogenous" is meant to refer to a substance present in a cell other than its native source. The term "exogenous" when used herein can refer to a nucleic acid (e.g., a nucleic acid encoding a polypeptide) or a polypeptide that has been introduced by a process involving the hand of man into a biological system such as a cell or organism in which it is not normally found and one wishes to introduce the nucleic acid or polypeptide into such a cell or organism. Alternatively, "exogenous" can refer to a nucleic acid or a polypeptide that has been introduced by a process involving the hand of man into a biological system such as a cell or organism in which it is found in relatively low amounts and one wishes to increase the amount of the nucleic acid or polypeptide in the cell or organism, e.g., to create ectopic expression or levels. In contrast, as used herein, the term "endogenous" refers to a substance that is native to the biological system or cell.

As used herein, the term "expression" is meant to refer to the cellular processes involved in producing RNA and proteins and as appropriate, secreting proteins, including where applicable, but not limited to, for example, transcription, transcript processing, translation and protein folding, modification and processing. As used herein, the phrase "expression products" include RNA transcribed from a gene (e.g., transgene), and polypeptides obtained by translation of mRNA transcribed from a gene.

As used herein, the term "expression vector" is meant to refer to a vector that directs expression of an RNA or polypeptide from sequences linked to transcriptional regulatory sequences on the vector. The sequences expressed will often, but not necessarily, be heterologous to the host cell. An expression vector may comprise additional elements, for example, the expression vector may have two replication systems, thus allowing it to be maintained in two organisms, for example in human cells for expression and in a prokaryotic host for cloning and amplification. The expression vector may be a recombinant vector.

As used herein, the terms "expression cassette" and "expression unit" are used interchangeably, and meant to refer to a heterologous DNA sequence that is operably linked to a promoter or other DNA regulatory sequence sufficient to direct transcription of a transgene of a DNA vector, e.g., synthetic AAV vector. Suitable promoters include, for example, tissue specific promoters. Promoters can also be of AAV origin.

As used herein, the term "flanking" is meant to refer to a relative position of one nucleic acid sequence with respect to another nucleic acid sequence. Generally, in the sequence ABC, B is flanked by A and C. The same is true for the arrangement AxBxC. Thus, a flanking sequence precedes or follows a flanked sequence but need not be contiguous with, or immediately adjacent to the flanked sequence. In one embodiment of any of the aspects or embodiments herein, the term flanking refers to terminal repeats at each end of the linear single strand synthetic AAV vector.

As used herein, the term "gene" is used broadly to refer to any segment of nucleic acid associated with expression of a given RNA or protein, in vitro or in vivo. Thus, genes include regions encoding expressed RNAs (which typically include polypeptide coding sequences) and, often, the regulatory sequences required for their expression. Genes can be obtained from a variety of sources, including cloning from a source of interest or synthesizing from known or predicted sequence information, and may include sequences designed to have specifically desired parameters.

As used herein, the phrase "genetic disease" or "genetic disorder" is meant to refer to a disease, partially or completely, directly or indirectly, caused by one or more abnormalities in the genome, including and especially a condition that is present from birth. The abnormality may be a mutation, an insertion or a deletion in a gene. The abnormality may affect the coding sequence of the gene or its regulatory sequence.

As used herein, the term "heterologous," is meant to refer to a nucleotide or polypeptide sequence that is not found in the native nucleic acid or protein, respectively. A heterologous nucleic acid sequence may be linked to a naturally occurring nucleic acid sequence (or a variant thereof) (e.g., by genetic engineering) to generate a chimeric nucleotide sequence encoding a chimeric polypeptide. A heterologous nucleic acid sequence may be linked to a variant polypeptide (e.g., by genetic engineering) to generate a nucleotide sequence encoding a fusion variant polypeptide.

As used herein, the term "host cell" refers to any cell type that is susceptible to transformation, transfection, transduction, and the like with nucleic acid therapeutics of the present disclosure. As non-limiting examples, a host cell can be an isolated primary cell, pluripotent stem cells, CD34$^+$ cells, induced pluripotent stem cells, or any of a number of immortalized cell lines (e.g., HepG2 cells). Alternatively, a host cell can be an in situ or in vivo cell in a tissue, organ or organism. Furthermore, a host cell can be a target cell of, for example, a mammalian subject (e.g., human patient in need of gene therapy).

As used herein, an "inducible promoter" is meant to refer to one that is characterized by initiating or enhancing transcriptional activity when in the presence of, influenced by, or contacted by an inducer or inducing agent. An "inducer" or "inducing agent," as used herein, can be endogenous, or a normally exogenous compound or protein that is administered in such a way as to be active in inducing transcriptional activity from the inducible promoter. In some embodiments of any of the aspects and embodiments herein, the inducer or inducing agent, i.e., a chemical, a compound or a protein, can itself be the result of transcription or expression of a nucleic acid sequence (i.e., an inducer can be an inducer protein expressed by another component or module), which itself can be under the control or an inducible promoter. In some embodiments of any of the aspects and embodiments herein, an inducible promoter is induced in the absence of certain agents, such as a repressor. Examples of inducible promoters include but are not limited to, tetracycline, metallothionine, ecdysone, mammalian viruses (e.g., the adenovirus late promoter; and the mouse mammary tumor virus long terminal repeat (MMTV-LTR)) and other steroid-responsive promoters, rapamycin responsive promoters and the like.

As used herein, the term "in vitro" is meant to refer to assays and methods that do not require the presence of a cell with an intact membrane, such as cellular extracts, and can refer to the introducing of a programmable synthetic biological circuit in a non-cellular system, such as a medium not comprising cells or cellular systems, such as cellular extracts.

As used herein, the term "in vivo" is meant to refer to assays or processes that occur in or within an organism, such as a multicellular animal. In some of the aspects described herein, a method or use can be said to occur "in vivo" when a unicellular organism, such as a bacterium, is used. The term "ex vivo" refers to methods and uses that are performed using a living cell with an intact membrane that is outside of the body of a multicellular animal or plant, e.g., explants, cultured cells, including primary cells and cell lines, transformed cell lines, and extracted tissue or cells, including blood cells, among others.

As used herein, the term "lipid" is meant to refer to a group of organic compounds that include, but are not limited to, esters of fatty acids and are characterized by being insoluble in water, but soluble in many organic solvents. They are usually divided into at least three classes: (1) "simple lipids," which include fats and oils as well as waxes; (2) "compound lipids," which include phospholipids and glycolipids; and (3) "derived lipids" such as steroids.

Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, and dilinoleoylphosphatidylcholine. Other compounds lacking in phosphorus, such as sphingolipid, glycosphingolipid families, diacylglycerols, and β-acyloxyacids, are also within the group designated as amphipathic lipids. Additionally, the amphipathic lipids described above can be mixed with other lipids including triglycerides and sterols.

In one embodiment of any of the aspects or embodiments herein, the lipid compositions comprise one or more tertiary amino groups, one or more phenyl ester bonds, and a disulfide bond.

As used herein, the term "lipid conjugate" is meant to refer to a conjugated lipid that inhibits aggregation of lipid particles (e.g., lipid nanoparticles). Such lipid conjugates include, but are not limited to, PEG-lipid conjugates such as, e.g., PEG coupled to dialkyloxypropyls (e.g., PEG-DAA conjugates), PEG coupled to diacylglycerols (e.g., PEG-DAG conjugates), PEG coupled to cholesterol, PEG coupled to phosphatidylethanolamines, and PEG conjugated to ceramides (see, e.g., U.S. Pat. No. 5,885,613), ionizable PEG lipids, polyoxazoline (POZ)-lipid conjugates (e.g., POZ-DAA conjugates; see, e.g., U.S. Provisional Application No. 61/294,828, filed Jan. 13, 2010, and U.S. Provisional Application No. 61/295,140, filed Jan. 14, 2010), polyamide oligomers (e.g., *ATTA*-lipid conjugates), and mixtures thereof. Additional examples of POZ-lipid conjugates are described in PCT Publication No. WO 2010/006282. PEG or POZ can be conjugated directly to the lipid or may be linked to the lipid via a linker moiety. Any linker moiety suitable for coupling the PEG or the POZ to a lipid can be used including, e.g., non-ester containing linker moieties and ester-containing linker moieties. In certain preferred embodiments, non-ester containing linker moieties, such as amides or carbamates, are used. The disclosures of each of the above patent documents are herein incorporated by reference in their entirety for all purposes. A lipid conjugate described herein (e.g., PEG-lipid or PEGylated lipid can be further covalently linked to a useful tissue targeting moiety known in the art (e.g., N-Acetylgalactosamine (GalNAc; mono-, di-, tri-, or tetra-antennary GalNAc).

As used herein, the term "lipid encapsulated" is meant to refer to a lipid particle that provides an active agent or therapeutic agent, such as a nucleic acid (e.g., an ASO, mRNA, siRNA, ceDNA, viral vector), with full encapsulation, partial encapsulation, or both. In a preferred embodiment, the nucleic acid is fully encapsulated in the lipid particle (e.g., to form a nucleic acid containing lipid particle).

As used herein, the terms "lipid particle" or "lipid nanoparticle" is meant to refer to a lipid formulation that can be used to deliver a therapeutic agent such as nucleic acid therapeutics (TNA) to a target site of interest (e.g., cell, tissue, organ, and the like) (referred to as "TNA lipid particle", "TNA lipid nanoparticle" or "TNA LNP"). In one embodiment of any of the aspects or embodiments herein, the lipid particle of the invention is a therapeutic nucleic acid containing lipid particle, which is typically formed from an ionizable lipid, a non-cationic lipid, and optionally a conjugated lipid that prevents aggregation of the particle. In other preferred embodiments, a therapeutic agent such as a therapeutic nucleic acid may be encapsulated in the lipid portion of the particle, thereby protecting it from enzymatic degradation. In one embodiment of any of the aspects or embodiments herein, the lipid particle comprises a nucleic acid (e.g., ceDNA) and a lipid comprising one or more tertiary amino groups, one or more phenyl ester bonds and a disulfide bond.

The lipid particles of the invention typically have a mean diameter of from about 20 nm to about 120 nm, about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, about 95 nm, about 100 nm, about 105 nm, about 110 nm, about 115 nm, about 120 nm, about 125 nm, about 130 nm, about 135 nm, about 140 nm, about 145 nm, or about 150 nm.

As used herein, the term "hydrophobic lipid" refers to compounds having apolar groups that include, but are not limited to, long-chain saturated and unsaturated aliphatic hydrocarbon groups and such groups optionally substituted by one or more aromatic, cycloaliphatic, or heterocyclic group(s). Suitable examples include, but are not limited to, diacylglycerol, dialkylglycerol, N—N-dialkylamino, 1,2-diacyloxy-3-aminopropane, and 1,2-dialkyl-3-aminopropane.

As used herein, the term "ionizable lipid" is meant to refer to a lipid, e.g., cationic lipid, having at least one protonatable or deprotonatable group, such that the lipid is positively charged at a pH at or below physiological pH (e.g., pH 7.4), and neutral at a second pH, preferably at or above physiological pH. It will be understood by one of ordinary skill in the art that the addition or removal of protons as a function of pH is an equilibrium process, and that the reference to a charged or a neutral lipid refers to the nature of the predominant species and does not require that all lipids be present in the charged or neutral form. Generally, ionizable lipids have a pKa of the protonatable group in the range of about 4 to about 7. In some embodiments of any of the aspects and embodiments herein, an ionizable lipid may include "cleavable lipid" or "SS-cleavable lipid". Accordingly, the term "ionizable lipid" as used herein encompasses both ionized (or charged) and neutral forms of the lipids of the invention.

As used herein, the term "neutral lipid" is meant to refer to any lipid species that exists either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

As used herein, the term "anionic lipid" refers to any lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleyol-phosphatidylglycerol (POPG), and other anionic modifying groups joined to neutral lipids.

As used herein, the term "non-cationic lipid" is meant to refer to any amphipathic lipid as well as any other neutral lipid or anionic lipid.

As used herein, the term "cleavable lipid" or "SS-cleavable lipid" refers to a lipid comprising a disulfide bond cleavable unit. In one embodiment of any of the aspects or embodiments herein, cleavable lipids comprise a tertiary amine, which responds to an acidic compartment, e.g., an endosome or lysosome for membrane destabilization and a disulfide bond that can be cleaved in a reducing environment, such as the cytoplasm. In one embodiment of any of the aspects or embodiments herein, a cleavable lipid is an ionizable lipid. In one embodiment of any of the aspects or embodiments herein, a cleavable lipid is a cationic lipid. In one embodiment of any of the aspects or embodiments herein, a cleavable lipid is an ionizable cationic lipid. Cleavable lipids are described in more detail herein.

As used herein, the term "organic lipid solution" is meant to refer to a composition comprising in whole, or in part, an organic solvent having a lipid.

As used herein, the term "liposome" is meant to refer to lipid molecules assembled in a spherical configuration encapsulating an interior aqueous volume that is segregated from an aqueous exterior. Liposomes are vesicles that possess at least one lipid bilayer. Liposomes are typical used as carriers for drug/therapeutic delivery in the context of pharmaceutical development. They work by fusing with a cellular membrane and repositioning its lipid structure to deliver a drug or active pharmaceutical ingredient. Liposome compositions for such delivery are typically composed of phospholipids, especially compounds having a phosphatidylcholine group, however these compositions may also include other lipids.

As used herein, the term "local delivery" is meant to refer to delivery of an active agent such as an interfering RNA (e.g., siRNA) directly to a target site within an organism. For example, an agent can be locally delivered by direct injection into a disease site such as a tumor or other target site such as a site of inflammation or a target organ such as the liver, heart, pancreas, kidney, and the like.

As used herein, the term "neDNA" or "nicked ceDNA" is meant to refer to a closed-ended DNA having a nick or a gap of 2-100 base pairs in a stem region or spacer region 5' upstream of an open reading frame (e.g., a promoter and transgene to be expressed).

As used herein, the term "nucleic acid," is meant to refer to a polymer containing at least two nucleotides (i.e., deoxyribonucleotides or ribonucleotides) in either single- or double-stranded form and includes DNA, RNA, and hybrids thereof. DNA may be in the form of, e.g., antisense molecules, plasmid DNA, DNA-DNA duplexes, pre-condensed DNA, PCR products, vectors (P1, PAC, BAC, YAC, artificial chromosomes), expression cassettes, chimeric sequences, chromosomal DNA, or derivatives and combinations of these groups. DNA may be in the form of minicircle, plasmid, bacmid, minigene, ministering DNA (linear covalently closed DNA vector), closed-ended linear duplex DNA (CELiD or ceDNA), Doggybone™ DNA, dumbbell shaped DNA, minimalistic immunological-defined gene expression (MIDGE)-vector, viral vector or non-viral vectors. RNA may be in the form of small interfering RNA (siRNA), Dicer-substrate dsRNA, small hairpin RNA (shRNA), asymmetrical interfering RNA (aiRNA), microRNA (miRNA), mRNA, rRNA, tRNA, viral RNA (vRNA), and combinations thereof. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs and/or modified residues include, without limitation, phosphorothioates, phosphorodiamidate morpholino oligomer (morpholino), phosphoramidates, methyl phosphonates, chiral-methyl phosphonates, 2'-O- methyl ribonucleotides, locked nucleic acid (LNA™), and peptide nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated.

As used herein, the phrases "nucleic acid therapeutics", "therapeutic nucleic acid" and "TNA" are used interchangeably and refer to any modality of therapeutic using nucleic acids as an active component of therapeutic agent to treat a disease or disorder. As used herein, these phrases refer to RNA-based therapeutics and DNA-based therapeutics. Non-limiting examples of RNA-based therapeutics include mRNA, antisense RNA and oligonucleotides, ribozymes, aptamers, interfering RNAs (RNAi), dicer-substrate dsRNA, small hairpin RNA (shRNA), asymmetrical interfering RNA (aiRNA), and microRNA (miRNA). Non-limiting examples of DNA-based therapeutics include minicircle DNA, minigene, viral DNA (e.g., Lentiviral or AAV genome) or nonviral DNA vectors, closed-ended linear duplex DNA (ceDNA/CELiD), plasmids, bacmids, Doggybone™ DNA vectors, minimalistic immunological-defined gene expression (MIDGE)-vector, nonviral ministring DNA vector (linear-covalently closed DNA vector), and dumbbell-shaped DNA minimal vector ("dumbbell DNA"). As used herein, the term "TNA LNP" refers to a lipid particle containing at least one of the TNA as described above.

As used herein, "nucleotides" contain a sugar deoxyribose (DNA) or ribose (RNA), a base, and a phosphate group. Nucleotides are linked together through the phosphate groups.

As used herein, "operably linked" is meant to refer to a juxtaposition wherein the components so described are in a relationship permitting them to function in their intended manner. For instance, a promoter is operably linked to a coding sequence if the promoter affects its transcription or expression. A promoter can be said to drive expression or drive transcription of the nucleic acid sequence that it regulates. The phrases "operably linked," "operatively positioned," "operatively linked," "under control," and "under transcriptional control" indicate that a promoter is in a correct functional location and/or orientation in relation to a nucleic acid sequence it regulates to control transcriptional initiation and/or expression of that sequence. An "inverted promoter," as used herein, refers to a promoter in which the nucleic acid sequence is in the reverse orientation, such that what was the coding strand is now the non-coding strand, and vice versa. Inverted promoter sequences can be used in various embodiments to regulate the state of a switch. In addition, in various embodiments, a promoter can be used in conjunction with an enhancer.

As used herein, the term "promoter" is meant to refer to any nucleic acid sequence that regulates the expression of another nucleic acid sequence by driving transcription of the nucleic acid sequence, which can be a heterologous target gene encoding a protein or an RNA. Promoters can be constitutive, inducible, repressible, tissue-specific, or any combination thereof. A promoter is a control region of a nucleic acid sequence at which initiation and rate of transcription of the remainder of a nucleic acid sequence are controlled. A promoter can also contain genetic elements at which regulatory proteins and molecules can bind, such as RNA polymerase and other transcription factors. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the expression of transgenes in the synthetic AAV vectors disclosed herein. A promoter sequence may be bounded at its 3' terminus by the transcription initiation site and extends upstream (5' direction) to include the minimum number of bases or elements necessary to initiate transcription at levels detectable above background.

A promoter can be one naturally associated with a gene or sequence, as can be obtained by isolating the 5' non-coding sequences located upstream of the coding segment and/or exon of a given gene or sequence. Such a promoter can be referred to as "endogenous." Similarly, in some embodiments of any of the aspects and embodiments herein, an enhancer can be one naturally associated with a nucleic acid sequence, located either downstream or upstream of that sequence. In some embodiments of any of the aspects and embodiments herein, a coding nucleic acid segment is positioned under the control of a "recombinant promoter" or "heterologous promoter," both of which refer to a promoter that is not normally associated with the encoded nucleic acid sequence that it is operably linked to in its natural environment. Similarly, a "recombinant or heterologous enhancer" refers to an enhancer not normally associated with a given nucleic acid sequence in its natural environment. Such promoters or enhancers can include promoters or enhancers of other genes; promoters or enhancers isolated from any other prokaryotic, viral, or eukaryotic cell; and synthetic promoters or enhancers that are not "naturally occurring," i.e., comprise different elements of different transcriptional regulatory regions, and/or mutations that alter expression through methods of genetic engineering that are known in the art. In addition to producing nucleic acid sequences of promoters and enhancers synthetically, promoter sequences can be produced using recombinant cloning and/or nucleic acid amplification technology, including PCR, in connection with the synthetic biological circuits and modules disclosed herein (see, e.g., U.S. Pat. Nos. 4,683,202, 5,928,906, each incorporated herein by reference in its entirety). Furthermore, it is contemplated that control sequences that direct transcription and/or expression of sequences within non-nuclear organelles such as mitochondria, chloroplasts, and the like, can be employed as well.

As used herein, the terms "Rep binding site" ("RBS") and "Rep binding element" ("RBE") are used interchangeably and are meant to refer to a binding site for Rep protein (e.g., AAV Rep 78 or AAV Rep 68) which upon binding by a Rep protein permits the Rep protein to perform its site-specific endonuclease activity on the sequence incorporating the RBS. An RBS sequence and its inverse complement together form a single RBS. RBS sequences are well known in the art, and include, for example, 5'-GCGCGCTCGCTCGCTC-3' (SEQ ID NO: 1), an RBS sequence identified in AAV2.

As used herein, the phrase "recombinant vector" is meant to refer to a vector that includes a heterologous nucleic acid sequence, or "transgene" that is capable of expression in vivo. It is to be understood that the vectors described herein can, in some embodiments of any of the aspects and embodiments herein, be combined with other suitable compositions and therapies. In some embodiments of any of the aspects and embodiments herein, the vector is episomal. The use of a suitable episomal vector provides a means of maintaining the nucleotide of interest in the subject in high copy number extra chromosomal DNA thereby eliminating potential effects of chromosomal integration.

As used herein, the term "reporter" is meant to refer to a protein that can be used to provide a detectable read-out. A reporter generally produces a measurable signal such as fluorescence, color, or luminescence. Reporter protein coding sequences encode proteins whose presence in the cell or organism is readily observed.

As used herein, the terms "sense" and "antisense" are meant to refer to the orientation of the structural element on the polynucleotide. The sense and antisense versions of an element are the reverse complement of each other.

As used herein, the term "sequence identity" is meant to refer to the relatedness between two nucleotide sequences. For purposes of the present disclosure, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows: (Identical Deoxyribonucleotides-.times.100)/(Length of Alignment-Total Number of Gaps in Alignment). The length of the alignment is preferably at least 10 nucleotides, preferably at least 25 nucleotides more preferred at least 50 nucleotides and most preferred at least 100 nucleotides.

As used herein, the term "spacer region" is meant to refer to an intervening sequence that separates functional elements in a vector or genome. In some embodiments of any of the aspects and embodiments herein, AAV spacer regions keep two functional elements at a desired distance for optimal functionality. In some embodiments of any of the aspects and embodiments herein, the spacer regions provide or add to the genetic stability of the vector or genome. In some embodiments of any of the aspects and embodiments herein, spacer regions facilitate ready genetic manipulation of the genome by providing a convenient location for cloning sites and a gap of design number of base pair. For example, in certain aspects, an oligonucleotide "polylinker" or "poly cloning site" containing several restriction endonuclease sites, or a non-open reading frame sequence designed to have no known protein (e.g., transcription factor) binding sites can be positioned in the vector or genome to separate the cis-acting factors, e.g., inserting a 6mer, 12mer, 18mer, 24mer, 48mer, 86mer, 176mer, etc.

As used herein, the term "subject" is meant to refer to a human or animal, to whom treatment, including prophylactic treatment, with the therapeutic nucleic acid according to the present invention, is provided. Usually, the animal is a vertebrate such as, but not limited to a primate, rodent, domestic animal or game animal. Primates include but are not limited to, chimpanzees, cynomolgus monkeys, spider monkeys, and macaques, e.g., Rhesus. Rodents include mice, rats, woodchucks, ferrets, rabbits and hamsters. Domestic and game animals include, but are not limited to, cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In certain embodiments of the aspects described herein, the subject is a mammal, e.g., a primate or a human. A subject can be male or female. Additionally, a subject can be an infant or a child. In some embodiments of any of the aspects and embodiments herein, the subject can be a neonate or an unborn subject, e.g., the subject is in utero. Preferably, the subject is a mammal. The mammal can be a human, non-human primate, mouse, rat, dog, cat, horse, or cow, but is not limited to these examples. Mammals other than humans can be advantageously used as subjects that represent animal models of diseases and disorders. In addition, the methods and compositions described herein can be used for domesticated animals and/or pets. A human subject can be of any age, gender, race or ethnic group, e.g., Caucasian (white), Asian, African, black, African American, African European, Hispanic, Mideastern, etc. In some embodiments of any of the aspects and embodiments herein, the subject can be a patient or other subject in a clinical setting. In some embodiments of any of the aspects and embodiments herein, the subject is already undergoing treatment. In some embodiments of any of the aspects and embodiments herein, the subject is an embryo, a fetus, neonate, infant, child, adolescent, or adult. In some embodiments of any of the aspects and embodiments herein, the subject is a human fetus, human neonate, human infant, human child, human adolescent, or human adult. In some embodiments of any of the aspects and embodiments herein, the subject is an animal embryo, or non-human embryo or non-human primate embryo. In some embodiments of any of the aspects and embodiments herein, the subject is a human embryo.

As used herein, the phrase "subject in need" refers to a subject that (i) will be administered a TNA lipid particle (or pharmaceutical composition comprising a TNA lipid particle) according to the described invention, (ii) is receiving a TNA lipid particle (or pharmaceutical composition comprising a TNA lipid particle) according to the described invention; or (iii) has received a TNA lipid particle (or pharmaceutical composition comprising a TNA lipid particle) according to the described invention, unless the context and usage of the phrase indicates otherwise.

As used herein, the term "suppress," "decrease," "interfere," "inhibit" and/or "reduce" (and like terms) generally refers to the act of reducing, either directly or indirectly, a concentration, level, function, activity, or behavior relative to the natural, expected, or average, or relative to a control condition.

As used herein, the terms "synthetic AAV vector" and "synthetic production of AAV vector" are meant to refer to an AAV vector and synthetic production methods thereof in an entirely cell-free environment.

As used herein, the term "systemic delivery" is meant to refer to delivery of lipid particles that leads to a broad biodistribution of an active agent such as an interfering RNA (e.g., siRNA) within an organism. Some techniques of administration can lead to the systemic delivery of certain agents, but not others. Systemic delivery means that a useful, preferably therapeutic, amount of an agent is exposed to most parts of the body. To obtain broad biodistribution generally requires a blood lifetime such that the agent is not rapidly degraded or cleared (such as by first pass organs (liver, lung, etc.) or by rapid, nonspecific cell binding) before reaching a disease site distal to the site of administration. Systemic delivery of lipid particles (e.g., lipid nanoparticles) can be by any means known in the art including, for example, intravenous, subcutaneous, and intraperitoneal. In a preferred embodiment, systemic delivery of lipid particles (e.g., lipid nanoparticles) is by intravenous delivery.

As used herein, the terms "terminal resolution site" and "TRS" are used interchangeably herein and meant to refer to a region at which Rep forms a tyrosine-phosphodiester bond with the 5' thymidine generating a 3'-OH that serves as a substrate for DNA extension via a cellular DNA polymerase, e.g., DNA pol delta or DNA pol epsilon. Alternatively, the Rep-thymidine complex may participate in a coordinated ligation reaction.

As used herein, the terms "therapeutic amount", "therapeutically effective amount", an "amount effective", "effective amount", or "pharmaceutically effective amount" of an active agent (e.g., a TNA lipid particle as described herein) are used interchangeably to refer to an amount that is sufficient to provide the intended benefit of treatment or effect e.g., inhibition of expression of a target sequence in comparison to the expression level detected in the absence of a therapeutic nucleic acid. Suitable assays for measuring expression of a target gene or target sequence include, e.g., examination of protein or RNA levels using techniques known to those of skill in the art such as dot blots, northern blots, in situ hybridization, ELISA, immunoprecipitation, enzyme function, as well as phenotypic assays known to those of skill in the art. Dosage levels are based on a variety of factors, including the type of injury, the age, weight, sex, medical condition of the patient, the severity of the condition, the route of administration, and the particular active agent employed. Thus, the dosage regimen may vary widely, but can be determined routinely by a physician using standard methods. Additionally, the terms "therapeutic amount", "therapeutically effective amounts" and "pharmaceutically effective amounts" include prophylactic or preventative amounts of the compositions of the described invention. In prophylactic or preventative applications of the described invention, pharmaceutical compositions or medicaments are administered to a patient susceptible to, or otherwise at risk of, a disease, disorder or condition in an amount sufficient to eliminate or reduce the risk, lessen the severity, or delay the onset of the disease, disorder or condition, including biochemical, histologic and/or behavioral symptoms of the disease, disorder or condition, its complications, and intermediate pathological phenotypes presenting during development of the disease, disorder or condition. It is generally preferred that a maximum dose be used, that is, the highest safe dose according to some medical judgment. The terms "dose" and "dosage" are used interchangeably herein. In one aspect of any of the aspects or embodiments herein, "therapeutic amount", "therapeutically effective amounts" and "pharmaceutically effective amounts" refer to non-prophylactic or non-preventative applications.

As used herein the term "therapeutic effect" refers to a consequence of treatment, the results of which are judged to be desirable and beneficial. A therapeutic effect can include, directly or indirectly, the arrest, reduction, or elimination of a disease manifestation. A therapeutic effect can also include, directly or indirectly, the arrest reduction or elimination of the progression of a disease manifestation.

For any therapeutic agent described herein therapeutically effective amount may be initially determined from preliminary in vitro studies and/or animal models. A therapeutically effective dose may also be determined from human data. The applied dose may be adjusted based on the relative bioavailability and potency of the administered compound. Adjusting the dose to achieve maximal efficacy based on the methods described above and other well-known methods is within the capabilities of the ordinarily skilled artisan. General principles for determining therapeutic effectiveness, which may be found in Chapter 1 of Goodman and Gilman's The Pharmacological Basis of Therapeutics, 10th Edition, McGraw-Hill (New York) (2001), incorporated herein by reference, are summarized below.

Pharmacokinetic principles provide a basis for modifying a dosage regimen to obtain a desired degree of therapeutic efficacy with a minimum of unacceptable adverse effects. In situations where the drug's plasma concentration can be measured and related to therapeutic window, additional guidance for dosage modification can be obtained.

As used herein, the terms "treat," "treating," and/or "treatment" include abrogating, inhibiting, slowing or reversing the progression of a condition, ameliorating clinical symptoms of a condition, or preventing the appearance of clinical symptoms of a condition, obtaining beneficial or desired clinical results. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously asymptomatic for the disorder(s). In one aspect of any of the aspects or embodiments herein, the terms "treat," "treating," and/or "treatment" include abrogating, inhibiting, slowing or reversing the progression of a condition, or ameliorating clinical symptoms of a condition.

Beneficial or desired clinical results, such as pharmacologic and/or physiologic effects include, but are not limited to, preventing the disease, disorder or condition from occurring in a subject that may be predisposed to the disease, disorder or condition but does not yet experience or exhibit symptoms of the disease (prophylactic treatment), alleviation of symptoms of the disease, disorder or condition, diminishment of extent of the disease, disorder or condition, stabilization (i.e., not worsening) of the disease, disorder or condition, preventing spread of the disease, disorder or condition, delaying or slowing of the disease, disorder or condition progression, amelioration or palliation of the disease, disorder or condition, and combinations thereof, as well as prolonging survival as compared to expected survival if not receiving treatment.

As used herein, the terms "vector" or "expression vector" are meant to refer to a replicon, such as plasmid, bacmid, phage, virus, virion, or cosmid, to which another DNA segment, i.e., an "insert" "transgene" or "expression cassette", may be attached so as to bring about the expression or replication of the attached segment ("expression cassette") in a cell. A vector can be a nucleic acid construct designed for delivery to a host cell or for transfer between different host cells. As used herein, a vector can be viral or non-viral in origin in the final form. However, for the purpose of the present disclosure, a "vector" generally refers to synthetic AAV vector or a nicked ceDNA vector. Accordingly, the term "vector" encompasses any genetic element that is capable of replication when associated with the proper control elements and that can transfer gene sequences to cells. In some embodiments of any of the aspects and embodiments herein, a vector can be a recombinant vector or an expression vector.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting. It should be understood that this invention is not limited in any manner to the particular methodology, protocols, and reagents, etc., described herein and as such can vary. The terminology used herein is for the purpose of describing particular embodiments only and is not intended to limit the scope of the present invention, which is defined solely by the claims.

II. Lipids

In a first chemical embodiment, provided are ionizable lipids of the Formula (I):

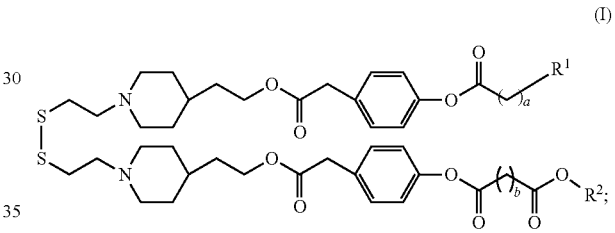

or a pharmaceutically acceptable salt thereof, wherein:
  a is an integer ranging from 1 to 20 (e.g., a is 1, 2, 3, 4, 5, 6, 7, 8, 9, 10, 11, 12, 13, 14, 15, 16, 17, 18, 19, or 20);
  b is an integer ranging from 2 to 10 (e.g., b is 2, 3, 4, 5, 6, 7, 8, 9, or 10);
  $R^1$ is absent or is selected from $(C_2-C_{20})$alkenyl, —C(O)O$(C_2-C_{20})$alkyl, and cyclopropyl substituted with $(C_2-C_{20})$alkyl; and
  $R^2$ is $(C_2-C_{20})$alkyl.

In a second chemical embodiment, the ionizable lipid of the Formula (I) is of the Formula (II):

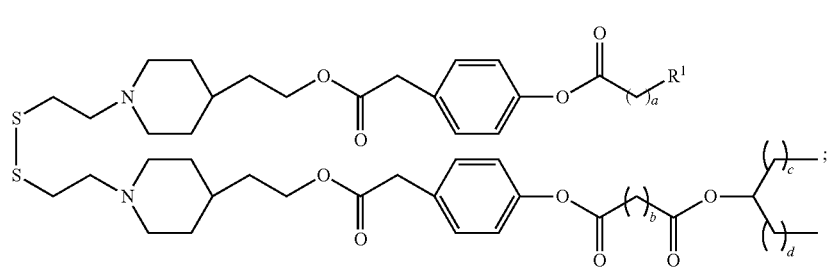

or a pharmaceutically acceptable salt thereof, wherein c and d are each independently integers ranging from 1 to 8 (e.g., 1, 2, 3, 4, 5, 6, 7, or 8), and wherein the remaining variables are as described for Formula (I).

In a third chemical embodiment, c and d in the ionizable lipid of Formula (I) or (II) or a pharmaceutically acceptable salt thereof are each independently integers ranging from 2 to 8, 3 to 8, 3 to 7, 3 to 6, 3 to 5, 4 to 8, 4 to 7, 4 to 6, 5 to 8, 5 to 7, or 6 to 8, wherein the remaining variables are as described for Formula (I) or (II).

In a fourth chemical embodiment, c in the ionizable lipid of Formula (I) or (II) is 2, 3, 4, 5, 6, 7, or 8, wherein the remaining variables are as described for Formula (I) or the second or third chemical embodiment. Alternatively, as part of a fourth chemical embodiment, c and d in the ionizable lipid of Formula (I) or (II) or a pharmaceutically acceptable salt thereof are each independently 1, 3, 5, or 7, wherein the remaining variables are as described for Formula (I) or the second or third chemical embodiment.

In a fifth chemical embodiment, d in the ionizable lipid of Formula (I) or (II) is 2, 3, 4, 5, 6, 7, or 8, wherein the remaining variables are as described for Formula (I) or the second or third or fourth chemical embodiment. Alternatively, as part of a fifth chemical embodiment, at least one of c and d in the ionizable lipid of Formula (I) or (II) or a pharmaceutically acceptable salt thereof is 7, wherein the remaining variables are as described for Formula (I) or the second or third or fourth chemical embodiment.

In a sixth chemical embodiment, the ionizable lipid of Formula (I) is of the Formula (III):

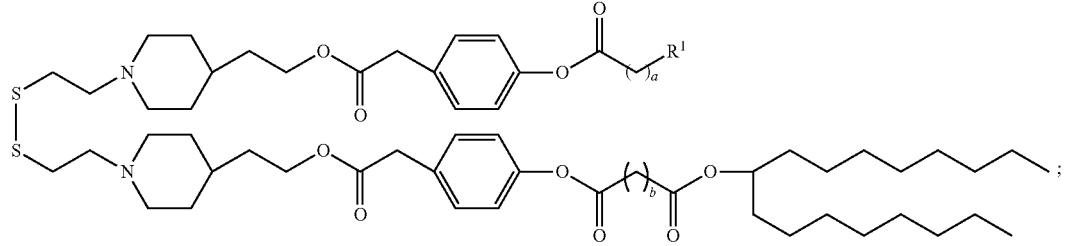

(III)

or a pharmaceutically acceptable salt thereof, wherein the remaining variables are as described for Formula (I).

In a seventh chemical embodiment, b in the ionizable lipid of Formula (I), (II), or (III) or a pharmaceutically acceptable salt thereof is an integer ranging from 3 to 9, wherein the remaining variables are as described for Formula (I), or the second, third, fourth or fifth chemical embodiment. Alternatively, as part of a seventh chemical embodiment, b in the ionizable lipid of Formula (I), (II), or (III) or a pharmaceutically acceptable salt thereof is an integer ranging from 3 to 8, 3 to 7, 3 to 6, 3 to 5, 4 to 9, 4 to 8, 4 to 7, 4 to 6, 5 to 9, 5 to 8, 5 to 7, 6 to 9, 6 to 8, or 7 to 9, wherein the remaining variables are as described for Formula (I), or the second, third, fourth or fifth chemical embodiment. In another alternative, as part of a seventh chemical embodiment, b in the ionizable lipid of Formula (I), (II), or (III) or a pharmaceutically acceptable salt thereof is 3, 4, 5, 6, 7, 8, or 9, wherein the remaining variables are as described for Formula (I), or the second, third, fourth or fifth chemical embodiment.

In an eighth chemical embodiment, a in the ionizable lipid of Formula (I), (II), or (III) or a pharmaceutically acceptable salt thereof is an integer ranging from 2 to 18, wherein the remaining variables are as described for Formula (I), or the second, third, fourth, fifth, or seventh chemical embodiment. Alternatively, as part of an eighth embodiment, a in the ionizable lipid of Formula (I), (II), or (III) or a pharmaceutically acceptable salt thereof is an integer ranging from 2 to 18, 2 to 17, 2 to 16, 2 to 15, 2 to 14, 2 to 13, 2 to 12, 2 to 11, 2 to 10, 2 to 9, 2 to 8, 2 to 7, 2 to 6, 2 to 5, 2 to 4, 3 to 18, 3 to 17, 3 to 16, 3 to 15, 3 to 14, 3 to 13, 3 to 12, 3 to 11, 3 to 10, 3 to 9, 3 to 8, 3 to 7, 3 to 6, 3 to 5, 4 to 18, 4 to 17, 4 to 16, 4 to 15, 4 to 14, 4 to 13, 4 to 12, 4 to 11, 4 to 10, 4 to 9, 4 to 8, 4 to 7, 4 to 6, 5 to 18, 5 to 17, 5 to 16, 5 to 15, 5 to 14, 5 to 13, 5 to 12, 5 to 11, 5 to 10, 5 to 9, 25 to 8, 5 to 7, 6 to 18, 6 to 17, 6 to 16, 6 to 15, 6 to 14, 6 to 13, 6 to 12, 6 to 11, 6 to 10, 6 to 9, 6 to 8, 7 to 18, 7 to 17, 7 to 16, 7 to 15, 7 to 14, 7 to 13, 7 to 12, 7 to 11, 7 to 10, 7 to 9, 8 to 18, 8 to 17, 8 to 16, 8 to 15, 8 to 14, 8 to 13, 8 to 12, 8 to 11, 8 to 10, 9 to 18, 9 to 17, 9 to 16, 9 to 15, 9 to 14, 9 to 13, 9 to 12, 9 to 11, 10 to 18, 10 to 17, 10 to 16, 10 to 15, 10 to 14, 10 to 13, 11 to 18, 11 to 17, 11 to 16, 11 to 15, 11 to 14, 11 to 13, 12 to 18, 12 to 17, 12 to 16, 12 to 15, 12 to 14, 13 to 18, 13 to 17, 13 to 16, 13 to 15, 14 to 18, 14 to 17, 14 to 16, 15 to 18, 15 to 17, or 16 to 18, wherein the remaining variables are as described for Formula (I), or the second, third, fourth, fifth, or seventh chemical embodiment. In another alternative, as part of an eighth embodiment, a in the ionizable lipid of Formula (I), (II), or (III) is 2, 3, 4, 5, 6, 7, 8, 9, 10, 11, 12, 13, 14, 15, 16, 17, or 18, wherein the remaining variables are as described for Formula (I), or the second, third, fourth, fifth, or seventh chemical embodiment.

In a ninth chemical embodiment, $R^1$ in the ionizable lipid of Formula (I), (II), or (III) or a pharmaceutically acceptable salt thereof is absent or is selected from $(C_5-C_{15})$alkenyl, —C(O)O$(C_4-C_{18})$alkyl, and cyclopropyl substituted with $(C_4-C_{16})$alkyl, wherein the remaining variables are as described for Formula (I), or the second, third, fourth, fifth, seventh, or eighth chemical embodiment. Alternatively, as part of a ninth chemical embodiment, $R^1$ in the ionizable lipid of Formula (I), (II), or (III) or a pharmaceutically acceptable salt thereof is absent or is selected from $(C_5-C_{15})$ alkenyl, —C(O)O$(C_4-C_{16})$alkyl, and cyclopropyl substituted with $(C_4-C_{16})$alkyl, wherein the remaining variables are as described for Formula (I), or the second, third, fourth, fifth, seventh, or eighth chemical embodiment. Alternatively, as part of a ninth chemical embodiment, $R^1$ in the ionizable lipid of Formula (I), (II), or (III) or a pharmaceutically acceptable salt thereof is absent or is selected from $(C_5-C_{12})$alkenyl, —C(O)O$(C_4-C_{12})$alkyl, and cyclopropyl substituted with $(C_4-C_{12})$alkyl, wherein the remaining variables are as described for Formula (I), or the second, third, fourth, fifth, seventh, or eighth chemical embodiment. In another alternative, as part of a ninth chemical embodiment, $R^1$ in the ionizable lipid of Formula (I), (II), or (III) or a pharmaceutically acceptable salt thereof is absent or is selected from $(C_5-C_{10})$alkenyl, —C(O)O$(C_4-C_{10})$alkyl, and cyclopropyl substituted with $(C_4-C_{10})$alkyl, wherein the remaining variables are as described for Formula (I), or the second, third, fourth, fifth, seventh, or eighth chemical embodiment.

In a tenth chemical embodiment, $R^1$ is $C_{10}$ alkenyl, wherein the remaining variables are as described in any one of the foregoing embodiments.

In an eleventh chemical embodiment, the alkyl in C(O)O($C_2$-$C_{20}$)alkyl, —C(O)O($C_4$-$C_{18}$)alkyl, —C(O)O($C_4$-$C_{12}$)alkyl, or —C(O)O($C_4$-$C_{10}$)alkyl of $R^1$ in the ionizable lipid of Formula (I), (II), or (III) or a pharmaceutically acceptable salt thereof is an unbranched alkyl, wherein the remaining variables are as described in any one of the foregoing embodiments. In one chemical embodiment, $R^1$ is —C(O)O($C_9$ alkyl). Alternatively, in an eleventh chemical embodiment, the alkyl in —C(O)O($C_4$-$C_{18}$)alkyl, —C(O)O($C_4$-$C_{12}$)alkyl, or —C(O)O($C_4$-$C_{10}$)alkyl of $R^1$ in the ionizable lipid of Formula (I), (II), or (III) or a pharmaceutically acceptable salt thereof is a branched alkyl, wherein the remaining variables are as described in any one of the foregoing chemical embodiments. In one chemical embodiment, $R^1$ is —C(O)O($C_{17}$ alkyl), wherein the remaining variables are as described in any one of the foregoing chemical embodiments.

In a twelfth chemical embodiment, $R^1$ in the ionizable lipid of Formula (I), (II), or (III) or a pharmaceutically acceptable salt thereof is selected from any group listed in Table 1 below, wherein the wavy bond in each of the groups indicates the point of attachment of the group to the rest of the lipid molecule, and wherein the remaining variables are as described for Formula (I), or the second, third, fourth, fifth, seventh, or eighth chemical embodiment. The present disclosure further contemplates the combination of any one of the $R^1$ groups in Table 1 with any one of the $R^2$ groups in Table 2, wherein the remaining variables are as described for Formula (I), or the second, third, fourth, fifth, seventh, or eighth chemical embodiment.

TABLE 1

Exemplary $R^1$ groups

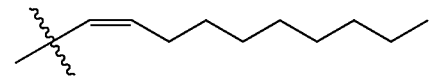 [SMILES: */C=C\CCCCCCCC]

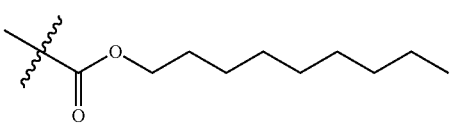 [SMILES: *C(=O)OCCCCCCCCC]

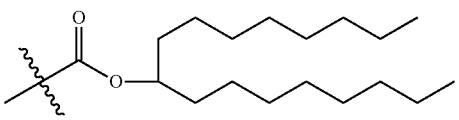 [SMILES: *C(=O)OC(CCCCCCCC)CCCCCCCC]

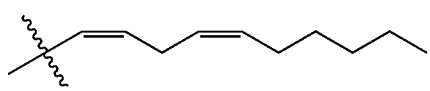

TABLE 1-continued

Exemplary $R^1$ groups

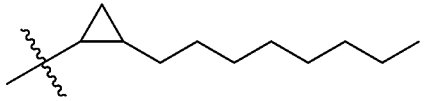 [SMILES: *C1CC1CCCCCCCC]

In a thirteenth chemical embodiment, $R^2$ in the ionizable lipid of Formula (I) or a pharmaceutically acceptable salt thereof is selected from any group listed in Table 2 below, wherein the wavy bond in each of the groups indicates the point of attachment of the group to the rest of the lipid molecule, and wherein the remaining variables are as described for Formula (I), or the seventh, eighth, ninth, tenth, or eleventh chemical embodiment.

TABLE 2

Exemplary $R^2$ groups

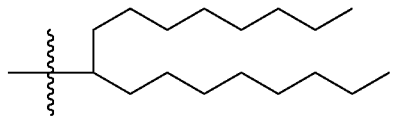 [SMILES: *C(CCCCCCCC)CCCCCCCC]

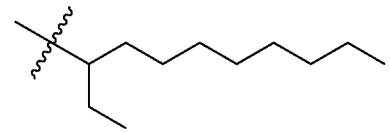 [SMILES: *C(CC)CCCCCCCC]

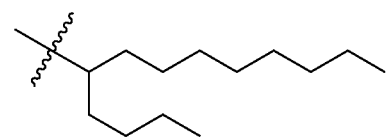 [SMILES: *C(CCCC)CCCCCCCC]

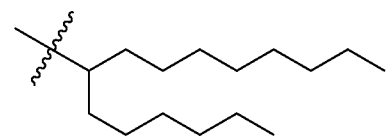 [SMILES: *C(CCCCCC)CCCCCCCC]

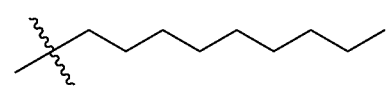 [SMILES: *CCCCCCCCC]

Specific examples are provided in Table 3 the exemplification section below and are included as part of a fourteenth chemical embodiment herein of ionizable lipids of Formula (I). Pharmaceutically acceptable salts as well as ionized and neutral forms are also included.

TABLE 3

Exemplary ionizable lipids of the disclosure

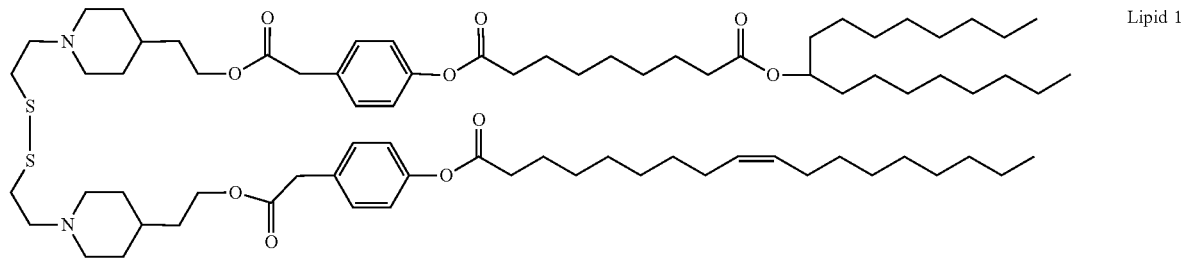

1-(heptadecan-9-yl) 9-(4-(2-(2-(1-(2-((2-(4-(2-(2-(4-
(oleoyloxy)phenyl)acetoxy)ethyl)piperidin-1-yl)ethyl)disulfaneyl)ethyl)piperidin-4-
yl)ethoxy)-2-oxoethyl)phenyl) nonanedioate Lipid 1

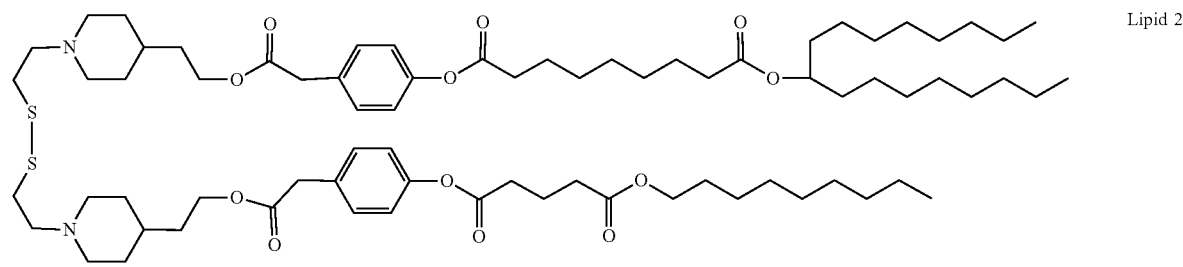

1-(heptadecan-9-yl) 9-(4-(2-(2-(1-(2-((2-(4-(2-(2-(4-((5-(nonyloyx)-5-
oxopentanoyl)oxy)phenyl)acetoxy)ethyl) piperidin-1-yl)ethyl)disulfaneyl)ethyl) piperidin-4-
yl)ethoxy)-2-oxoethyl)phenyl) nonanediote Lipid 2

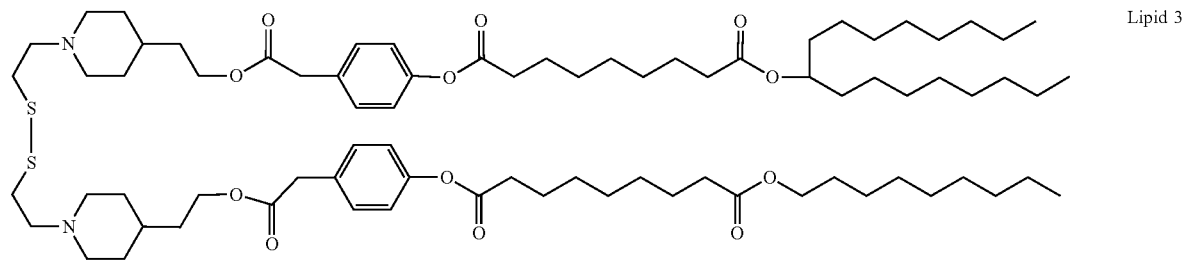

1-(heptadecan-9-yl) 9-(4-(2-(1-(2-((2-(4-(2-(2-(4-((9-(nonyloxy)-9-
oxononanoyl)oxy)phenyl)acetoxy)ethyl)piperidin-1-yl)ethyl)disulfaneyl)ethyl)piperidin-4-
yl)ethoxy)-2-oxoethyl)phenyl) nonanediote Lipid 3

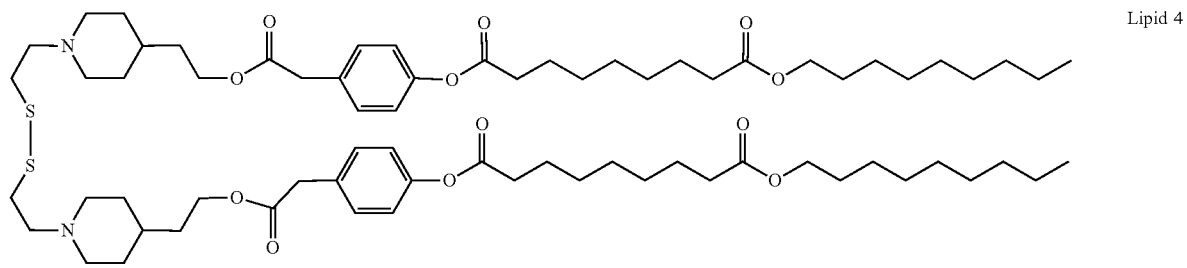

1-(heptadecan-9-yl) 9-(4-(2-(2-(1-(2-((2-(4-(2-(2-(4-((5-(nonyloxy)-5-
oxopentanoyl)oxy)phenyl)acetoxy)ethyl)
piperidin-1-yl)ethyl)disulfaneyl)ethyl)piperidin-4-yl)ethoxy)-2-oxoethyl)phenyl)
nonanediote Lipid 4

TABLE 3-continued

Exemplary ionizable lipids of the disclosure

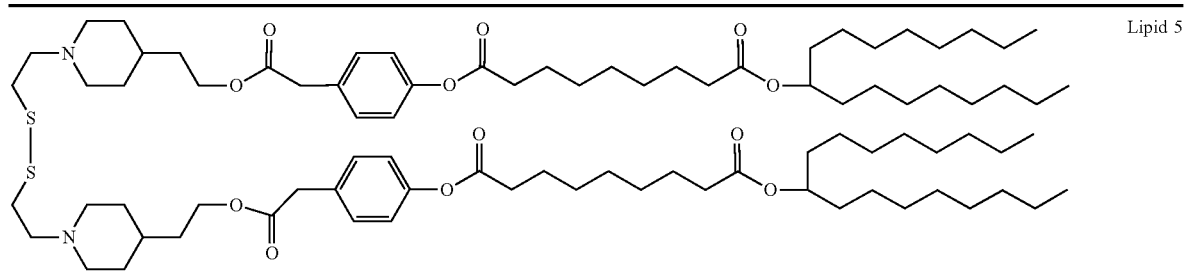

O'1,O1-((((((disulfanediylbis(ethane-2,1-diyl))bis(piperidine-1,4-diyl))bis(ethane-2,1-diyl))bis(oxy))bis(2-oxoethane-2,1-diyl))bis(4,1-phenylene)) 9,9'-di(heptadecan-9-yl) di(nonanediote)

Lipid 5

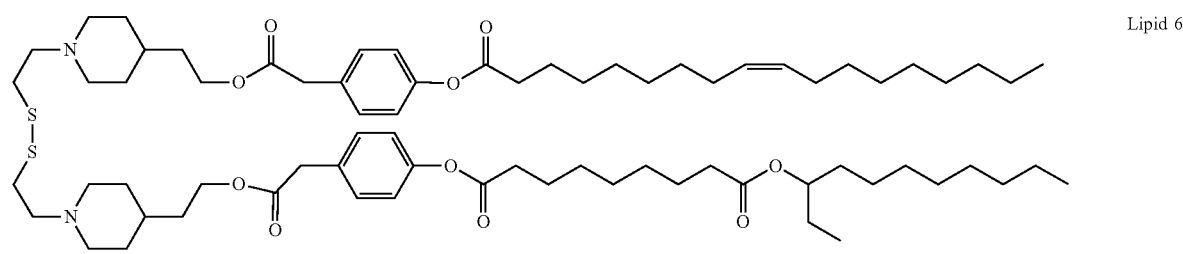

1-(4-(2-(2-(1-(2-((2-(4-(2-(4-(oleoyloxy)phenyl)acetoxy)ethyl)piperidin-1-yl)ethyl)disulfaneyl)ethyl)piperidin-4-yl)ethoxy)-2-oxoethyl)phenyl) 9-(undecan-3-yl) nonanediote Lipid 6

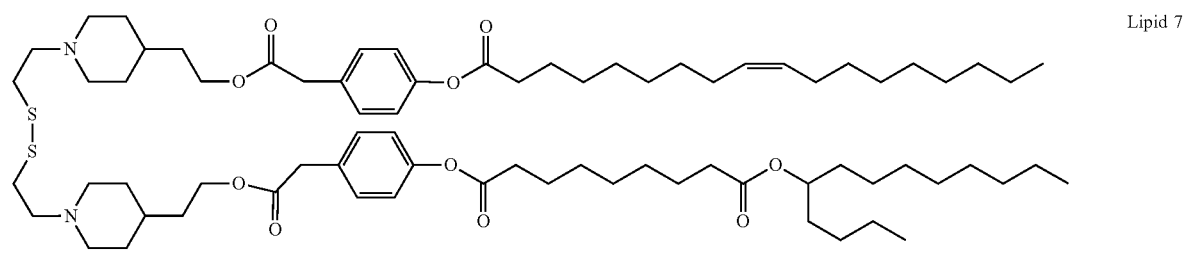

1-(4-(2-(2-(1-(2-((2-(4-(2-(4-(oleoyloxy)phenyl)acetoxy)ethyl)piperidin-1-yl)ethyl)disulfaneyl)ethyl)piperidin-4-yl)ethoxy)-2-oxoethyl)phenyl) 9-(tridecan-5-yl) nonanediote Lipid 7

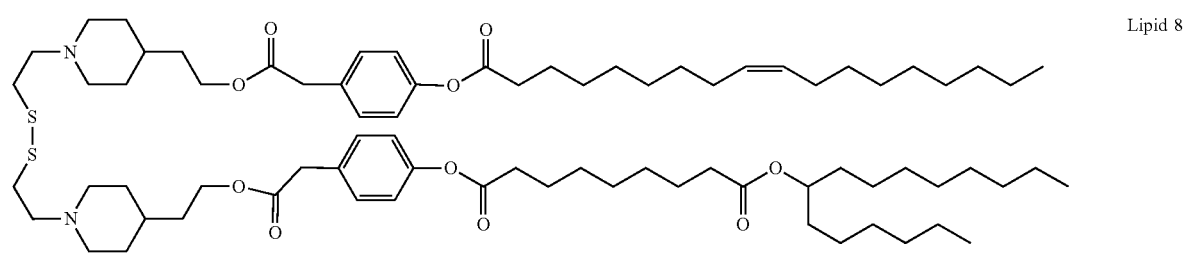

1-(4-(2-(2-(1-(2-((2-(4-(2-(4-(oleoyloxy)phenyl)acetoxy)ethyl)piperidin-1-yl)ethyl)disulfaneyl)ethyl)piperidin-4-yl)ethoxy)-2-oxoethyl)phenyl 9-(pentadecan-7-yl) nonanediote Lipid 8

TABLE 3-continued

Exemplary ionizable lipids of the disclosure

Lipid 9

1-nonyl 9-(4-(2-oxo-2-(2-(1-(2-((2-(4-(2-(2-(4-((9-oxo-9-(undecan-3-yloxy)nonayl)oxy)phenyl)acetoxy)ethyl)piperidin-1-yl)ethyl)disulfaneyl)ethyl)piperidin-4-yl)ethoxy)ethyl)phenyl) nonanediote Lipid 10

1-nonyl 9-(4-(2-oxo-2-(2-(1-(2-((2-(4-(2-(2-(4-((9-oxo-9-(tridecan-5-yloxy)nonanoyl)oxy)phenyl)acetoxy)ethyl)piperidin-1-yl)ethyl)disulfaneyl)ethyl)piperidin-4-yl)ethoxy)ethyl)phenyl) nonanedioate Lipid 11

1-nonyl 9-(4-(2-oxo-2-(2-(1-(2-((2-(4-(2-(2-(4-((9-oxo-9-(pentadecan-7-yloxy)nonanoyl)oxy)phenyl)acetoxy)ethyl)piperidin-1-yl)ethyl)disulfaneyl)ethyl)piperidin-4-yl)ethoxy)ethyl)phenyl) nonanedioate Lipid 12

1-(heptadecan-9-yl) 9-(4-(2-(2-(1-(2-((2-(4-(2-(2-(4-(((9Z,12Z)-octadeca-9,12-dienoyl)oxy)phenyl)acetoxy)ethyl)piperidin-1-yl)ethyl)disulfaneyl)ethyl)piperidin-4-yl)ethoxy)-2-oxoethyl)phenyl) nonanediote Lipid 13

1-(heptadecan-9-yl) 9-(4-(2-(2-(1-(2-((2-(4-(2-(2-(4-((8-(2-octylcyclopropyl)octanoyl)oxy)phenyl)acetoxy)ethyl)piperidin-1-yl)ethyl)disulfaneyl)ethyl)piperidin-4-yl)ethoxy)-2-oxoethyl)phenyl) nonanediote TABLE 3-continued Exemplary ionizable lipids of the disclosure

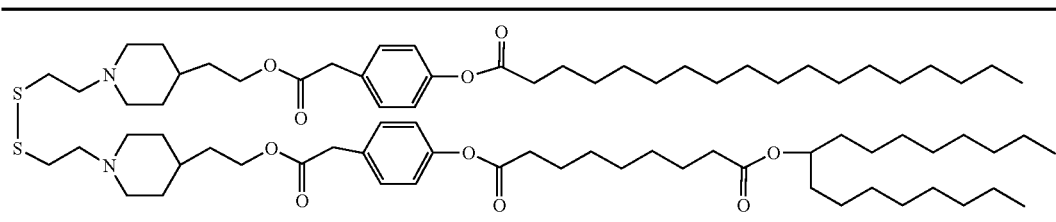

Lipid 14

1-(heptadecan-9-yl) 9-(4-(2-oxo-2-(2-(1-(2-((2-(4-(2-(2-(4-
(stearoyloxy)phenyl)acetoxy)ethyl)piperidin-1-yl)ethyl)disulfaneyl)ethyl)piperidin-4-
yl)ethoxy)ethyl)phenyl) nonanedioate

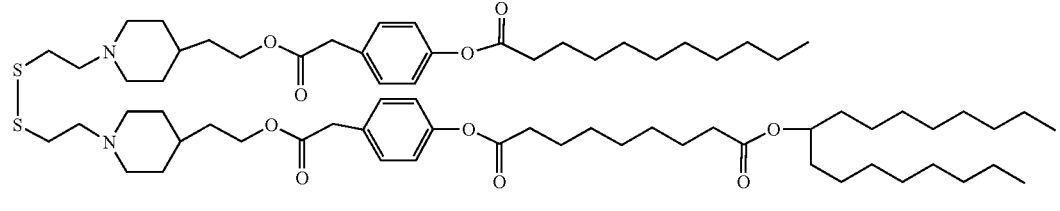 [SMILES: CCCCCCCCCCC(=O)Oc1ccc(CC(=O)OCCC2CCN(CCSSCCN3CCC(CCOC(=O)Cc4ccc(OC(=O)CCCCCCCC(=O)OC(CCCCCCCC)CCCCCCCC)cc4)CC3)CC2)cc1]

Lipid 15

1-(heptadecan-9-yl) 9-(4-(2-oxo-2-(2-(1-(2-((2-(4-(2-(2-(4-
(undecanoyloxy)phenyl)acetoxy)ethyl)piperidin-1-yl)ethyl)disulfaneyl)ethyl)piperidin-4-
yl)ethoxy)ethyl)phenyl) nonanedioate

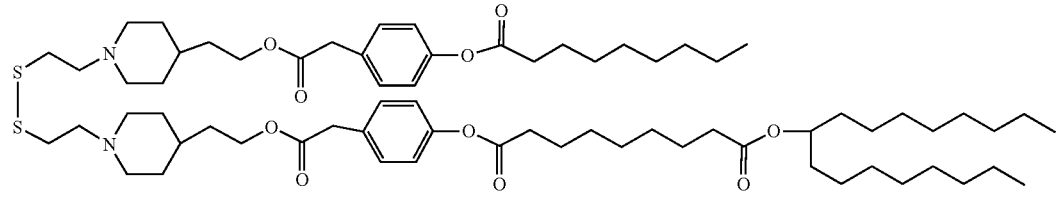 [SMILES: CCCCCCCCC(=O)Oc1ccc(CC(=O)OCCC2CCN(CCSSCCN3CCC(CCOC(=O)Cc4ccc(OC(=O)CCCCCCCC(=O)OC(CCCCCCCC)CCCCCCCC)cc4)CC3)CC2)cc1]

Lipid 16

1-(heptadecan-9-yl) 9-(4-(2-(2-(1-(2-((2-(4-(2-(2-(4-
(nonanoyloxy)phenyl)acetoxy)ethyl)piperidin-1-yl)ethyl)disulfaneyl)ethyl)piperidin-4-
yl)ethoxy)-2-oxoethyl)phenyl) nonanediote

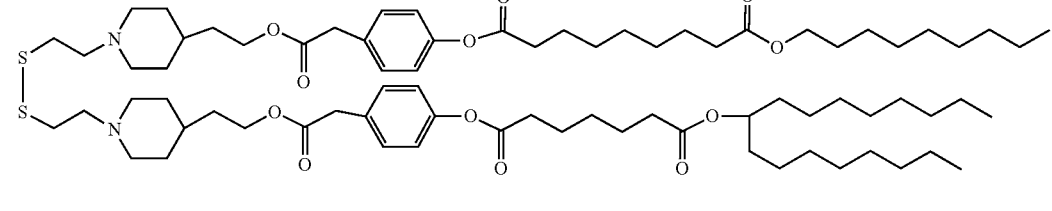

Lipid 17

1-nonyl 9-(4-(2-(2-(1-(2-((2-(4-(2-(2-(4-((9-((3-octylundecyl)oxy)-9-
oxononanoyl)oxy)phenyl)acetoxy)ethyl)piperidin-1-yl)ethyl)disulfaneyl)ethyl)piperidin-4-
yl)ethoxy)-2-oxoethyl)phenyl) nonanedioate

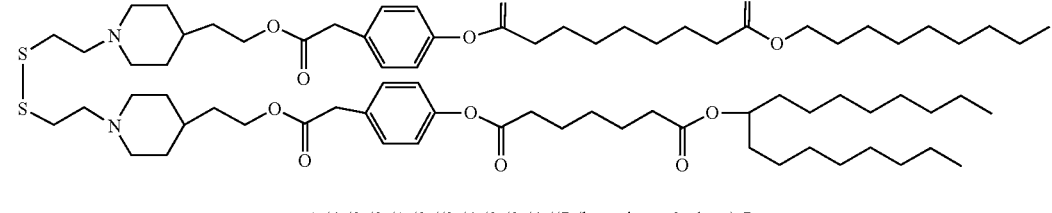

Lipid 18

1-(4-(2-(2-(1-(2-((2-(4-(2-(2-(4-((7-(heptadecan-9-yloxy)-7-
oxoheptanoyl)oxy)phenyl)acetoxy)ethyl)piperidin-1-yl)ethyl)disulfaneyl)ethyl)piperidin-4-
yl)ethoxy)-2-oxoethyl)phenyl) 9-nonyl nonanediote TABLE 3-continued Exemplary ionizable lipids of the disclosure Lipid 19

1-nonyl 9-(4-(2-(2-(1-(2-((2-(4-(2-(2-(4-((9-((3-octylundecyl)oxy)-9-oxononanoyl)oxy)phenyl)acetoxy)ethyl)piperidin-1-yl)ethyl)disulfaneyl)ethyl)piperidin-4-yl)ethoxy)-2-oxoethyl)phenyl) nonanedioate Lipid 20

1-nonyl 9-(4-(2-(2-(1-(2-((2-(4-(2-(2-(4-((7-((3-octylundecyl)oxy)-7-oxoheptanoyl)oxy)phenyl)acetoxy)ethyl)piperidin-1-yl)ethyl)disulfaneyl)ethyl)piperidin-4-yl)ethoxy)-2-oxoethyl)phenyl) nonanedioate In a further aspect, contemplated herein are lipids of Formula (Ia), (Ib), or (Ic):

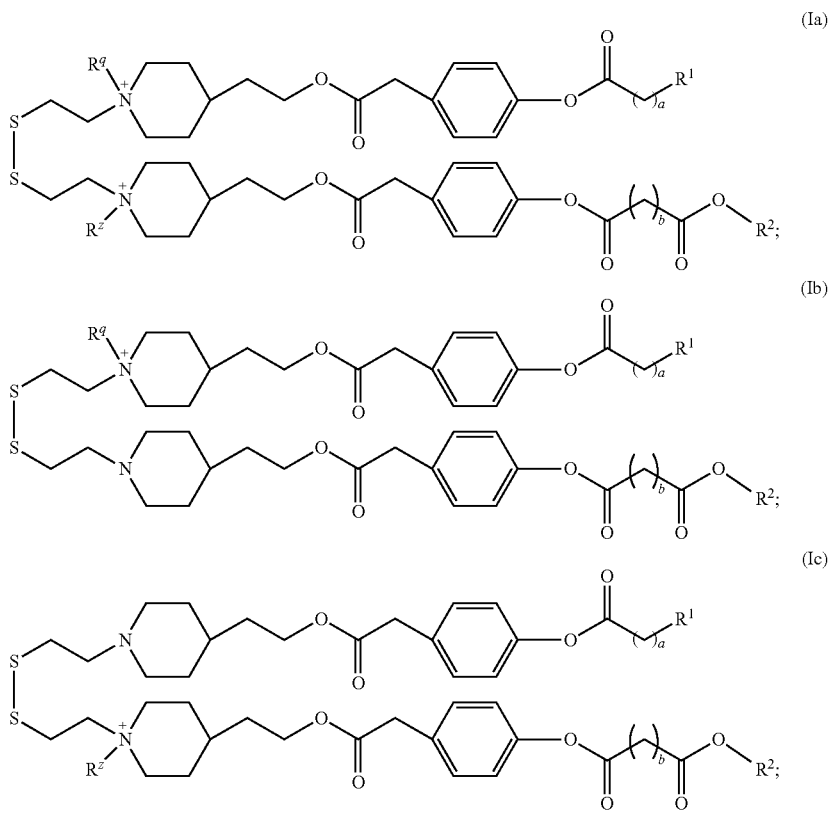

or a pharmaceutically acceptable salt thereof, wherein $R^q$ and $R^z$ are each independently an aliphatic group (including alkyls, alkenyls, alkynyls, cycloalkyls, heterocyclyls) or an aryl group, wherein the remaining variables are as described above in any one of the foregoing chemical embodiments. In one embodiment, $R^q$ and $R^z$ are each independently hydrogen or $C_1$-$C_6$ alkyl, wherein the remaining variables are as described above in any one of the foregoing chemical embodiments. The disclosed LNPs, compositions, methods of use, etc., also apply to lipids of Formula (Ia), (Ib), or (Ic). Lipids of Formula (Ia), (Ib), or (Ic) may be prepared, for example, the lipid of Formula (I) by treatment with chloromethane ($CH_3Cl$) in acetonitrile ($CH_3CN$) and chloroform ($CHCl_3$).

Moreover, a lipid of Formula (II), or (III), or any of the exemplary lipids disclosed herein may be converted to corresponding quaternary lipids (all contemplated in this disclosure), for example, the lipid of Formula (I) by treatment with chloromethane ($CH_3Cl$) in acetonitrile ($CH_3CN$) and chloroform ($CHCl_3$).

Lipid nanoparticles (LNPs), or pharmaceutical compositions thereof, comprising an ionizable lipid described herein and a capsid free, non-viral vector (e.g., ceDNA) can be used to deliver the capsid-free, non-viral DNA vector to a target site of interest (e.g., cell, tissue, organ, and the like).

In one embodiment of any of the aspects or embodiments herein, a lipid particle (e.g., lipid nanoparticle) formulation is made and loaded with TNA. In one embodiment, a lipid particle (e.g., lipid nanoparticle) formulation is made and loaded with ceDNA obtained by the process as disclosed in International Application PCT/US2018/050042, filed on Sep. 7, 2018, which is incorporated by reference in its entirety herein. This can be accomplished by high energy mixing of ethanolic lipids with aqueous TNA such as ceDNA at low pH which protonates the lipid and provides favorable energetics for ceDNA/lipid association and nucleation of particles. The particles can be further stabilized through aqueous dilution and removal of the organic solvent. The particles can be concentrated to the desired level.

Generally, the lipid particles (e.g., lipid nanoparticles) are prepared at a total lipid to nucleic acid (mass or weight) ratio of from about 10:1 to 60:1. In some embodiments of any of the aspects and embodiments herein, the lipid to nucleic acid ratio (mass/mass ratio; w/w ratio) can be in the range of from about 1:1 to about 60:1, from about 1:1 to about 55:1, from about 1:1 to about 50:1, from about 1:1 to about 45:1, from about 1:1 to about 40:1, from about 1:1 to about 35:1, from about 1:1 to about 30:1, from about 1:1 to about 25:1, from about 10:1 to about 14:1, from about 3:1 to about 15:1, from about 4:1 to about 10:1, from about 5:1 to about 9:1, about 6:1 to about 9:1; from about 30:1 to about 60:1. According to some embodiments of any of the aspects or embodiments herein, the lipid particles (e.g., lipid nanoparticles) are prepared at a nucleic acid (mass or weight) to total lipid ratio of about 60:1. According to some embodiments of any of the aspects or embodiments herein, the lipid particles (e.g., lipid nanoparticles) are prepared at a nucleic acid (mass or weight) to total lipid ratio of about 30:1. The amounts of lipids and nucleic acid can be adjusted to provide a desired N/P ratio, for example, N/P ratio of 3, 4, 5, 6, 7, 8, 9, 10, 11, 12, 13, 14 15, 16, 17, 18, 19, 20 or higher. Generally, the lipid particle formulation's overall lipid content can range from about 5 mg/ml to about 30 mg/mL.

In some embodiments of any of the aspects and embodiments herein, the lipid nanoparticle comprises an agent for condensing and/or encapsulating nucleic acid cargo, such as ceDNA. Such an agent is also referred to as a condensing or encapsulating agent herein. Without limitations, any compound known in the art for condensing and/or encapsulating nucleic acids can be used as long as it is non-fusogenic. In other words, an agent capable of condensing and/or encapsulating the nucleic acid cargo, such as ceDNA, but having little or no fusogenic activity. Without wishing to be bound by a theory, a condensing agent may have some fusogenic activity when not condensing/encapsulating a nucleic acid, such as ceDNA, but a nucleic acid encapsulating lipid nanoparticle formed with said condensing agent can be non-fusogenic.

Generally, an ionizable lipid or a cationic lipid is typically employed to condense the nucleic acid cargo, e.g., ceDNA at low pH and to drive membrane association and fusogenicity. Generally, cationic lipids are lipids comprising at least one amino group that is positively charged or becomes protonated under acidic conditions, for example at pH of 6.5 or lower. Cationic lipids may also be ionizable lipids, e.g., ionizable cationic lipids. By a "non-fusogenic ionizable lipid" is meant an ionizable lipid that can condense and/or encapsulate the nucleic acid cargo, such as ceDNA, but does not have, or has very little, fusogenic activity.

In one embodiment of any of the aspects or embodiments herein, the ionizable lipid can comprise 20-90% (mol) of the total lipid present in the lipid particles (e.g., lipid nanoparticles). For example, the ionizable lipid molar content can be 20-70% (mol), 30-60% (mol), 40-60% (mol), 40-55% (mol) or 45-55% (mol) of the total lipid present in the lipid particle (e.g., lipid nanoparticles). In some embodiments of any of the aspects and embodiments herein, the ionizable lipid comprises from about 50 mol % to about 90 mol % of the total lipid present in the lipid particles (e.g., lipid nanoparticles).

In one embodiment of any of the aspects or embodiments herein, the lipid particles (e.g., lipid nanoparticles) can further comprise a non-cationic lipid. The non-cationic lipid may serve to increase fusogenicity and also increase stability of the LNP during formation. Non-cationic lipids include amphipathic lipids, neutral lipids and anionic lipids. Accordingly, the non-cationic lipid can be a neutral uncharged, zwitterionic, or anionic lipid. Non-cationic lipids are typically employed to enhance fusogenicity.

Exemplary non-cationic lipids include, but are not limited to, distearoyl-sn-glycero-phosphoethanolamine, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), monomethyl-phosphatidylethanolamine (such as 16-O-monomethyl PE), dimethyl-phosphatidylethanolamine (such as 16-O-dimethyl PE), 18-1-trans PE, 1-stearoyl-2-oleoyl-phosphatidyethanolamine (SOPE), hydrogenated soy phosphatidylcholine (HSPC), egg phosphatidylcholine (EPC), dioleoylphosphatidylserine (DOPS), sphingomyelin (SM), dimyristoyl phosphatidylcholine (DMPC), dimyristoyl phosphatidylglycerol (DMPG), distearoylphosphatidylglycerol (DSPG), dierucoylphosphatidylcholine (DEPC), palmitoyloleoylphosphatidylglycerol (POPG), dielaidoyl-phosphatidylethanolamine (DEPE), 1,2-dilauroyl-sn-glycero-3-phosphoethanolamine (DLPE); 1,2-diphytanoyl-sn-glycero-3-phosphoethanolamine (DPHyPE); lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidicacid, cerebrosides, dicetylphosphate, lysophosphatidylcholine, dilinoleoylphosphatidylcholine, or mixtures thereof. It is to be understood that other diacylphosphatidylcholine and diacylphosphatidylethanolamine phospholipids can also be used. The acyl groups in these lipids are preferably acyl groups derived from fatty acids having $C_{10}$-$C_{24}$ carbon chains, e.g., lauroyl, myristoyl, palmitoyl, stearoyl, or oleoyl.

Other examples of non-cationic lipids suitable for use in the lipid particles (e.g., lipid nanoparticles) include non-phosphorous lipids such as, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide, ceramide, sphingomyelin, and the like.

In one embodiment of any of the aspects or embodiments herein, the non-cationic lipid is a phospholipid. In one embodiment of any of the aspects or embodiments herein, the non-cationic lipid is selected from the group consisting of DSPC, DPPC, DMPC, DOPC, POPC, DOPE, and SM. In some embodiments of any of the aspects and embodiments herein, the non-cationic lipid is DSPC. In other embodiments, the non-cationic lipid is DOPC. In other embodiments, the non-cationic lipid is DOPE.

In some embodiments of any of the aspects and embodiments herein, the non-cationic lipid can comprise 0 to about 20% (mol) of the total lipid present in the lipid nanoparticle. In some embodiments of any of the aspects and embodiments herein, the non-cationic lipid content is 0.5-15% (mol) of the total lipid present in the lipid particle (e.g., lipid nanoparticle). In some embodiments of any of the aspects and embodiments herein, the non-cationic lipid content is 5-12% (mol) of the total lipid present in the lipid particle (e.g., lipid nanoparticle). In some embodiments of any of the aspects and embodiments herein, the non-cationic lipid content is 5-10% (mol) of the total lipid present in the lipid particle (e.g., lipid nanoparticle). In one embodiment of any of the aspects or embodiments herein, the non-cationic lipid content is about 6% (mol) of the total lipid present in the lipid particle (e.g., lipid nanoparticle). In one embodiment of any of the aspects or embodiments herein, the non-cationic lipid content is about 7.0% (mol) of the total lipid present in the lipid particle (e.g., lipid nanoparticle). In one embodiment of any of the aspects or embodiments herein, the non-cationic lipid content is about 7.5% (mol) of the total lipid present in the lipid particle (e.g., lipid nanoparticle). In one embodiment of any of the aspects or embodiments herein, the non-cationic lipid content is about 8.0% (mol) of the total lipid present in the lipid particle (e.g., lipid nanoparticle). In one embodiment of any of the aspects or embodiments herein, the non-cationic lipid content is about 9.0% (mol) of the total lipid present in the lipid particle (e.g., lipid nanoparticle). In some embodiments of any of the aspects and embodiments herein, the non-cationic lipid content is about 10% (mol) of the total lipid present in the lipid particle (e.g., lipid nanoparticle). In one embodiment of any of the aspects or embodiments herein, the non-cationic lipid content is about 11% (mol) of the total lipid present in the lipid particle (e.g., lipid nanoparticle).

Exemplary non-cationic lipids are described in PCT Publication WO2017/099823 and US patent publication US2018/0028664, the contents of both of which are incorporated herein by reference in their entirety.

In one embodiment of any of the aspects or embodiments herein, the lipid particles (e.g., lipid nanoparticles) can further comprise a component, such as a sterol, to provide membrane integrity and stability of the lipid particle. In one embodiment of any of the aspects or embodiments herein, an exemplary sterol that can be used in the lipid particle is cholesterol, or a derivative thereof. Non-limiting examples of cholesterol derivatives include polar analogues such as 5α-cholestanol, 5β-coprostanol, cholesteryl-(2'-hydroxy)-ethyl ether, cholesteryl-(4'-hydroxy)-butyl ether, and 6-ketocholestanol; non-polar analogues such as 5α-cholestane, cholestenone, 5α-cholestanone, 5β-cholestanone, and cholesteryl decanoate; and mixtures thereof. In some embodiments of any of the aspects and embodiments herein, the cholesterol derivative is a polar analogue such as cholesteryl-(4'-hydroxy)-butyl ether. In some embodiments of any of the aspects and embodiments herein, cholesterol derivative is cholesteryl hemisuccinate (CHEMS).

Exemplary cholesterol derivatives are described in PCT publication WO2009/127060 and US patent publication US2010/0130588, contents of both of which are incorporated herein by reference in their entirety.

In one embodiment of any of the aspects or embodiments herein, the component providing membrane integrity, such as a sterol, can comprise 0-50% (mol) of the total lipid present in the lipid particle (e.g., lipid nanoparticle). In some embodiments of any of the aspects and embodiments herein, such a component is 20-50% (mol) of the total lipid content of the lipid particle (e.g., lipid nanoparticle). In some embodiments of any of the aspects and embodiments herein, such a component is 30-40% (mol) of the total lipid content of the lipid particle (e.g., lipid nanoparticle). In some embodiments of any of the aspects and embodiments herein, such a component is 35-45% (mol) of the total lipid content of the lipid particle (e.g., lipid nanoparticle). In some embodiments of any of the aspects and embodiments herein, such a component is 38-42% (mol) of the total lipid content of the lipid particle (e.g., lipid nanoparticle).

In one embodiment of any of the aspects or embodiments herein, the lipid particle (e.g., lipid nanoparticle) can further comprise a polyethylene glycol (PEG) or a conjugated lipid molecule. Generally, these are used to inhibit aggregation of lipid particle (e.g., lipid nanoparticle) and/or provide steric stabilization. Exemplary conjugated lipids include, but are not limited to, PEG-lipid conjugates, polyoxazoline (POZ)-lipid conjugates, polyamide-lipid conjugates (such as ATTA-lipid conjugates), cationic-polymer lipid (CPL) conjugates, and mixtures thereof. In some embodiments of any of the aspects and embodiments herein, the conjugated lipid molecule is a PEG-lipid conjugate, for example, a (methoxy polyethylene glycol)-conjugated lipid. In some other embodiments, the conjugated lipid molecule is a PEG-lipid conjugate, for example, a $PEG_{2000}$-DMG (dimyristoylglycerol).

Exemplary PEG-lipid conjugates include, but are not limited to, PEG-diacylglycerol (DAG) (such as 1-(monomethoxy-polyethyleneglycol)-2,3-dimyristoylglycerol (PEG-DMG)), PEG-dialkyloxypropyl (DAA), PEG-phospholipid, PEG-ceramide (Cer), a pegylated phosphatidylethanoloamine (PEG-PE), PEG succinate diacylglycerol (PEGS-DAG) (such as 4-0-(2',3'-di(tetradecanoyloxy)propyl-1-0-(w-methoxy(polyethoxy)ethyl) butanedioate (PEG-S-DMG)), PEG dialkoxypropylcarbam, N-(carbonyl-methoxypoly ethylene glycol 2000)-1,2-distearoyl-sn-glycero-3-phosphoethanolamine sodium salt, or a mixture thereof. Additional exemplary PEG-lipid conjugates are described, for example, in U.S. Pat. Nos. 5,885,613, 6,287,591, US2003/0077829, US2003/0077829, US2005/0175682, US2008/0020058, US2011/0117125, US2010/0130588, US2016/0376224, and US2017/0119904, the contents of all of which are incorporated herein by reference in their entirety.

In one embodiment of any of the aspects or embodiments herein, the PEG-DAA conjugate can be, for example, PEG-dilauryloxypropyl, PEG-dimyristyloxypropyl, PEG-dipalmityloxypropyl, or PEG-distearyloxypropyl. The PEG-lipid can be one or more of PEG-DMG, PEG-dilaurylglycerol, PEG-dipalmitoylglycerol, PEG-disterylglycerol, PEG-dilaurylglycamide, PEG-dimyristylglycamide, PEG-dipalmitoylglycamide, PEG-disterylglycamide, PEG-cholesterol (1-[8'-(Cholest-5-en-3[beta]-oxy)carboxamido-3',6'-dioxaoctanyl] carbamoyl-[omega]-methyl-poly(ethylene glycol), PEG-DMB (3,4-Ditetradecoxylbenzyl-[omega]-methyl-poly(ethylene glycol) ether), and 1,2-dimyristoyl-sn-glycero-3-phosphoethanolamine-N-[methoxy(polyethylene glycol)-2000]. In one embodiment of any of the aspects or embodiments herein, the PEG-lipid can be selected from the group consisting of PEG-DMG, 1,2-dimyristoyl-sn-glycero-3-phosphoethanolamine-N-[methoxy(polyethylene glycol)-2000].

In one embodiment of any of the aspects or embodiments herein, lipids conjugated with a molecule other than a PEG can also be used in place of PEG-lipid. For example, polyoxazoline (POZ)-lipid conjugates, polyamide-lipid conjugates (such as ATTA-lipid conjugates), and cationic-polymer lipid (CPL) conjugates can be used in place of or in addition to the PEG-lipid. Exemplary conjugated lipids, i.e., PEG-lipids, (POZ)-lipid conjugates, ATTA-lipid conjugates and cationic polymer-lipids are described in the PCT patent application publications WO1996/010392, WO1998/051278, WO2002/087541, WO2005/026372, WO2008/147438, WO2009/086558, WO2012/000104, WO2017/117528, WO2017/099823, WO2015/199952, WO2017/004143, WO2015/095346, WO2012/000104, WO2012/000104, and WO2010/006282, US patent application publications US2003/0077829, US2005/0175682, US2008/0020058, US2011/0117125, US2013/0303587, US2018/0028664, US2015/0376115, US2016/0376224, US2016/0317458, US2013/0303587, US2013/0303587, and US20110123453, and US patents U.S. Pat. Nos. 5,885,613, 6,287,591, 6,320,017, and 6,586,559, the contents of all of which are incorporated herein by reference in their entireties.

In some embodiments of any of the aspects and embodiments herein, the PEG-lipid conjugate is present at a molar ratio of about 0% to about 20% in the lipid nanoparticle. In some embodiments of any of the aspects and embodiments herein, the PEG-lipid conjugate content is 0.5-10% (mol) in the lipid particle (e.g., lipid nanoparticle). In some embodiments of any of the aspects and embodiments herein, the PEG-lipid conjugate content is 1-5% (mol) in the lipid particle (e.g., lipid nanoparticle). In some embodiments of any of the aspects and embodiments herein, the PEG-lipid conjugate content is 1-3% (mol) in the lipid particle (e.g., lipid nanoparticle). In one embodiment of any of the aspects or embodiments herein, the PEG-lipid conjugate content is about 1.5% (mol) of the total lipid present in the lipid particle (e.g., lipid nanoparticle). In some embodiments of any of the aspects and embodiments herein, the PEG-lipid conjugate content is about 2% (mol) in the lipid particle (e.g., lipid nanoparticle). In some embodiments of any of the aspects and embodiments herein, the PEG-lipid conjugate content is about 2.5% (mol) in the lipid particle (e.g., lipid nanoparticle). In some embodiments of any of the aspects and embodiments herein, the PEG-lipid conjugate content is about 3% (mol) of the total lipid present in the lipid particle (e.g., lipid nanoparticle). In some embodiments of any of the aspects and embodiments herein, the PEG-lipid conjugate content is about 3% (mol) in the lipid particle (e.g., lipid nanoparticle). In some embodiments of any of the aspects and embodiments herein, the PEG-lipid conjugate content is about 3.5% (mol) in the lipid particle (e.g., lipid nanoparticle).

In some embodiments of any of the aspects and embodiments herein, the conjugated lipid, such as PEG-lipid conjugate or PEG-gylated lipid, is present at a molar percentage of greater than about 2.0% of the total lipid in the lipid nanoparticle, for example, about 2.1%, or 2.2%, or 2.3%, or 2.4%, or about 2.5% to about 10%; or about 2.1%, or 2.2%, or 2.3%, or 2.4%, or about 2.5% to about 7.5%; about 2.1%, or 2.2%, or 2.3%, or 2.4%, or about 2.5% to about 5%; about 3% to about 5%; about 3% to about 4.5%; about 3% to about 4%; about 3.5% to about 5%; about 3.5% to about 4.5%, about 2.5% to about 4%; about 2.5% to about 3.5%, or about 2.5% to about 3%.

It is understood that molar ratios of a disclosed ionizable lipid with the non-cationic lipid, sterol, and PEG-conjugated lipid can be varied as needed. For example, the lipid particle (e.g., lipid nanoparticle) can comprise 30-70% lipid by mole or by total weight of the composition, 0-60% cholesterol by mole or by total weight of the composition, 0-30% non-cationic lipid by mole or by total weight of the composition and 1-10% PEG-conjugated lipid by mole or by total weight of the composition. In one embodiment of any of the aspects or embodiments herein, the composition comprises 40-60% ionizable lipid by mole or by total weight of the composition, 30-50% cholesterol by mole or by total weight of the composition, 5-15% non-cationic lipid by mole or by total weight of the composition and 1-5% PEG-conjugated lipid by mole or by total weight of the composition. In one embodiment of any of the aspects or embodiments herein, the composition is 40-60% ionizable lipid by mole or by total weight of the composition, 30-40% cholesterol by mole or by total weight of the composition, and 5-10% non-cationic lipid, by mole or by total weight of the composition and 1-5% PEG-conjugated lipid by mole or by total weight of the composition. The composition may contain 60-70% ionizable lipid by mole or by total weight of the composition, 25-35% cholesterol by mole or by total weight of the composition, 5-10% non-cationic lipid by mole or by total weight of the composition and 0-5% PEG-conjugated lipid by mole or by total weight of the composition. The composition may also contain up to 45-55% ionizable lipid by mole or by total weight of the composition, 35-45% cholesterol by mole or by total weight of the composition, 2 to 15% non-cationic lipid by mole or by total weight of the composition, and 1-5% PEG-conjugated lipid by mole or by total weight of the composition. The formulation may also be a lipid nanoparticle formulation, for example comprising 8-30% ionizable lipid by mole or by total weight of the composition, 5-15% non-cationic lipid by mole or by total weight of the composition, and 0-40% cholesterol by mole or by total weight of the composition; 4-25% ionizable lipid by mole or by total weight of the composition, 4-25% non-cationic lipid by mole or by total weight of the composition, 2 to 25% cholesterol by mole or by total weight of the composition, 10 to 35% conjugate lipid by mole or by total weight of the composition, and 5% cholesterol by mole or by total weight of the composition; or 2-30% ionizable lipid by mole or by total weight of the composition, 2-30% non-cationic lipid by mole or by total weight of the composition, 1 to 15% cholesterol by mole or by total weight of the composition, 2 to 35% PEG-conjugate lipid by mole or by total weight of the composition, and 1-20% cholesterol by mole or by total weight of the composition; or even up to 90% ionizable lipid by mole or by total weight of the composition and 2-10% non-cationic lipids by mole or by total weight of the composition, or even 100% ionizable lipid by mole or by total weight of the composition. In some embodiments of any of the aspects and embodiments herein, the lipid particle formulation comprises ionizable lipid, non-cationic phospholipid, cholesterol and a PEG-ylated lipid (conjugated lipid) in a molar ratio of about 50:10:38.5:1.5. In some embodiments of any of the aspects and embodiments herein, the lipid particle formulation comprises ionizable lipid, non-cationic phospholipid, cholesterol and a PEG-ylated lipid (conjugated lipid) in a molar ratio of about 50:10:38:2. In some embodiments of any of the aspects and embodiments herein, the lipid particle formulation comprises ionizable lipid, non-cationic phospholipid, cholesterol and a PEG-ylated lipid (conjugated lipid) in a molar ratio of about 50:10:37:3. In one embodiment of any of the aspects or embodiments herein, the lipid particle (e.g., lipid nanoparticle) formulation comprises ionizable lipid, non-cationic phospholipid, cholesterol and a PEG-ylated lipid (conjugated lipid) in a molar ratio of about 50:7:40:3. In one embodiment of any of the aspects or embodiments herein, the lipid particle (e.g., lipid nanoparticle) formulation comprises ionizable lipid, non-cationic phospholipid, cholesterol and a PEG-ylated lipid (conjugated lipid) in a molar ratio of about 50:8:40:2. In one embodiment of any of the aspects or embodiments herein, the lipid particle (e.g., lipid nanoparticle) formulation comprises ionizable lipid, non-cationic phospholipid, cholesterol and a PEG-ylated lipid (conjugated lipid) in a molar ratio of about 50:9:39:2. In one embodiment of any of the aspects or embodiments herein, the lipid particle (e.g., lipid nanoparticle) formulation comprises ionizable lipid, non-cationic phospholipid, cholesterol and a PEG-ylated lipid (conjugated lipid) in a molar ratio of about 50:9:38:3.

In one embodiment of any of the aspects or embodiments herein, the lipid particle (e.g., lipid nanoparticle) comprises ionizable lipid, non-cationic lipid (e.g. phospholipid), a sterol (e.g., cholesterol) and a PEG-ylated lipid (conjugated lipid), where the molar ratio of lipids ranges from 20 to 70 mole percent for the ionizable lipid, with a target of 30-60, the mole percent of non-cationic lipid ranges from 0 to 30, with a target of 0 to 15, the mole percent of sterol ranges from 20 to 70, with a target of 30 to 50, and the mole percent of PEG-ylated lipid (conjugated lipid) ranges from 1 to 6, with a target of 2 to 5.

Lipid nanoparticles (LNPs) comprising ceDNA are disclosed in International Application PCT/US2018/050042, filed on Sep. 7, 2018, which is incorporated herein in its entirety and envisioned for use in the methods and compositions as disclosed herein.

Lipid particle (e.g., lipid nanoparticle) size can be determined by quasi-elastic light scattering using a Malvern Zetasizer Nano ZS (Malvern, UK) and is approximately 50-150 nm diameter, approximately 55-95 nm diameter, or approximately 70-90 nm diameter.

The pKa of formulated ionizable lipids can be correlated with the effectiveness of the LNPs for delivery of nucleic acids (see Jayaraman et al., Angewandte Chemie, International Edition (2012), 51(34), 8529-8533; Semple et al., Nature Biotechnology 28, 172-176 (20 1 0), both of which are incorporated by reference in their entireties). In one embodiment of any of the aspects or embodiments herein, the pKa of each ionizable lipid is determined in lipid nanoparticles using an assay based on fluorescence of 2-(p-toluidino)-6-napthalene sulfonic acid (TNS). Lipid nanoparticles comprising of ionizable lipid/DSPC/cholesterol/PEG-lipid (50/10/38.5/1.5 mol %) in PBS at a concentration of 0.4 mM total lipid can be prepared using the in-line process as described herein and elsewhere. TNS can be prepared as a 100 mM stock solution in distilled water. Vesicles can be diluted to 24 mM lipid in 2 mL of buffered solutions containing, 10 mM HEPES, 10 mM MES, 10 mM ammonium acetate, 130 mM NaCl, where the pH ranges from 2.5 to 11. An aliquot of the TNS solution can be added to give a final concentration of 1 mM and following vortex mixing fluorescence intensity is measured at room temperature in a SLM Aminco Series 2 Luminescence Spectrophotometer using excitation and emission wavelengths of 321 nm and 445 nm. A sigmoidal best fit analysis can be applied to the fluorescence data and the pKa is measured as the pH giving rise to half-maximal fluorescence intensity.

In one embodiment of any of the aspects or embodiments herein, relative activity can be determined by measuring luciferase expression in the liver 4 hours following administration via tail vein injection. The activity is compared at a dose of 0.3 and 1.0 mg ceDNA/kg and expressed as ng luciferase/g liver measured 4 hours after administration.

Without limitations, a lipid particle (e.g., lipid nanoparticle) of the disclosure includes a lipid formulation that can be used to deliver a capsid-free, non-viral DNA vector to a target site of interest (e.g., cell, tissue, organ, and the like). Generally, the lipid particle (e.g., lipid nanoparticle) comprises capsid-free, non-viral DNA vector and an ionizable lipid or a salt thereof.

In one embodiment of any of the aspects or embodiments herein, the lipid particle (e.g., lipid nanoparticle) comprises an ionizable lipid/non-cationic lipid/sterol/conjugated lipid at a molar ratio of 50:10:38.5:1.5.

In one embodiment of any of the aspects or embodiments herein, the disclosure provides for a lipid particle (e.g., lipid nanoparticle) formulation comprising phospholipids, lecithin, phosphatidylcholine and phosphatidylethanolamine.

III. Therapeutic Nucleic Acid (TNA)

The present disclosure provides a lipid-based platform for delivering therapeutic nucleic acid (TNA). Non-limiting examples of RNA-based therapeutics include mRNA, antisense RNA and oligonucleotides, ribozymes, aptamers, interfering RNAs (RNAi), dicer-substrate dsRNA, small hairpin RNA (shRNA), asymmetrical interfering RNA (aiRNA), microRNA (miRNA). Non-limiting examples of DNA-based therapeutics include minicircle DNA, minigene, viral DNA (e.g., Lentiviral or AAV genome) or non-viral DNA vectors, closed-ended linear duplex DNA (ceDNA/CELiD), plasmids, bacmids, Doggybone™ DNA vectors, minimalistic immunological-defined gene expression (MIDGE)-vector, nonviral ministering DNA vector (linear-covalently closed DNA vector), or dumbbell-shaped DNA minimal vector ("dumbbell DNA"). As such, aspects of the present disclosure generally provide ionizable lipid particles (e.g., lipid nanoparticles) comprising a TNA.

Therapeutic Nucleic Acids

Illustrative therapeutic nucleic acids of the present disclosure can include, but are not limited to, minigenes, plasmids, minicircles, small interfering RNA (siRNA), microRNA (miRNA), antisense oligonucleotides (ASO), ribozymes, closed ended double stranded DNA (e.g., ceDNA, CELiD, linear covalently closed DNA ("ministering"), Doggybone™ protelomere closed ended DNA, or dumbbell linear DNA), dicer-substrate dsRNA, small hairpin RNA (shRNA), asymmetrical interfering RNA (aiRNA), microRNA (miRNA), mRNA, tRNA, rRNA, and DNA viral vectors, viral RNA vector, and any combination thereof.

siRNA or miRNA that can downregulate the intracellular levels of specific proteins through a process called RNA interference (RNAi) are also contemplated by the present invention to be nucleic acid therapeutics. After siRNA or miRNA is introduced into the cytoplasm of a host cell, these double-stranded RNA constructs can bind to a protein called RISC. The sense strand of the siRNA or miRNA is removed by the RISC complex. The RISC complex, when combined with the complementary mRNA, cleaves the mRNA and release the cut strands. RNAi is by inducing specific destruction of mRNA that results in downregulation of a corresponding protein.

Antisense oligonucleotides (ASO) and ribozymes that inhibit mRNA translation into protein can be nucleic acid therapeutics. For antisense constructs, these single stranded deoxynucleic acids have a complementary sequence to the sequence of the target protein mRNA and are capable of binding to the mRNA by Watson-Crick base pairing. This binding prevents translation of a target mRNA, and/or triggers RNaseH degradation of the mRNA transcript. As a result, the antisense oligonucleotide has increased specificity of action (i.e., down-regulation of a specific disease-related protein).

In any of the methods and compositions provided herein, the therapeutic nucleic acid (TNA) can be a therapeutic RNA. Said therapeutic RNA can be an inhibitor of mRNA translation, agent of RNA interference (RNAi), catalytically active RNA molecule (ribozyme), transfer RNA (tRNA) or an RNA that binds an mRNA transcript (ASO), protein or other molecular ligand (aptamer). In any of the methods provided herein, the agent of RNAi can be a double-stranded RNA, single-stranded RNA, micro RNA, short interfering RNA, short hairpin RNA, or a triplex-forming oligonucleotide.

In any of the methods composition provided herein, the therapeutic nucleic acid (TNA) can be a therapeutic DNA such as closed ended double stranded DNA (e.g., ceDNA, CELiD, linear covalently closed DNA ("ministering"), Doggybone™, protelomere closed ended DNA, dumbbell linear DNA, plasmid, minicircle or the like). Some embodiments of the disclosure are based on methods and compositions comprising closed-ended linear duplexed (ceDNA) that can express a transgene (e.g., a therapeutic nucleic acid). The ceDNA vectors as described herein have no packaging constraints imposed by the limiting space within the viral capsid. ceDNA vectors represent a viable eukaryotically-produced alternative to prokaryote-produced plasmid DNA vectors.

ceDNA vectors preferably have a linear and continuous structure rather than a non-continuous structure. The linear and continuous structure is believed to be more stable from attack by cellular endonucleases, as well as less likely to be recombined and cause mutagenesis. Thus, a ceDNA vector in the linear and continuous structure is a preferred embodiment. The continuous, linear, single strand intramolecular duplex ceDNA vector can have covalently bound terminal ends, without sequences encoding AAV capsid proteins. These ceDNA vectors are structurally distinct from plasmids (including ceDNA plasmids described herein), which are circular duplex nucleic acid molecules of bacterial origin. The complimentary strands of plasmids may be separated following denaturation to produce two nucleic acid molecules, whereas in contrast, ceDNA vectors, while having complimentary strands, are a single DNA molecule and therefore even if denatured, remain a single molecule. In some embodiments of any of the aspects and embodiments herein, ceDNA vectors can be produced without DNA base methylation of prokaryotic type, unlike plasmids. Therefore, the ceDNA vectors and ceDNA-plasmids are different both in term of structure (in particular, linear versus circular) and also in view of the methods used for producing and purifying these different objects, and also in view of their DNA methylation which is of prokaryotic type for ceDNA-plasmids and of eukaryotic type for the ceDNA vector.

Provided herein are non-viral, capsid-free ceDNA molecules with covalently-closed ends (ceDNA). These non-viral capsid free ceDNA molecules can be produced in permissive host cells from an expression construct (e.g., a ceDNA-plasmid, a ceDNA-bacmid, a ceDNA-baculovirus, or an integrated cell-line) containing a heterologous gene (e.g., a transgene, in particular a therapeutic transgene) positioned between two different inverted terminal repeat (ITR) sequences, where the ITRs are different with respect to each other. In some embodiments of any of the aspects and embodiments herein, one of the ITRs is modified by deletion, insertion, and/or substitution as compared to a wild-type ITR sequence (e.g., AAV ITR); and at least one of the ITRs comprises a functional terminal resolution site (TRS) and a Rep binding site. The ceDNA vector is preferably duplex, e.g., self-complementary, over at least a portion of the molecule, such as the expression cassette (e.g., ceDNA is not a double stranded circular molecule). The ceDNA vector has covalently closed ends, and thus is resistant to exonuclease digestion (e.g., exonuclease I or exonuclease III), e.g., for over an hour at 37° C.

In one aspect of any of the aspects or embodiments herein, a ceDNA vector comprises, in the 5' to 3' direction: a first adeno-associated virus (AAV) inverted terminal repeat (ITR), a nucleotide sequence of interest (for example an expression cassette as described herein) and a second AAV ITR. In one embodiment of any of the aspects or embodiments herein, the first ITR (5' ITR) and the second ITR (3' ITR) are asymmetric with respect to each other—that is, they have a different 3D-spatial configuration from one another. As an exemplary embodiment, the first ITR can be a wild-type ITR and the second ITR can be a mutated or modified ITR, or vice versa, where the first ITR can be a mutated or modified ITR and the second ITR a wild-type ITR. In one embodiment of any of the aspects or embodiments herein, the first ITR and the second ITR are both modified but are different sequences, or have different modifications, or are not identical modified ITRs, and have different 3D spatial configurations. Stated differently, a ceDNA vector with asymmetric ITRs have ITRs where any changes in one ITR relative to the WT-ITR are not reflected in the other ITR; or alternatively, where the asymmetric ITRs have a the modified asymmetric ITR pair can have a different sequence and different three-dimensional shape with respect to each other.

In one embodiment of any of the aspects or embodiments herein, a ceDNA vector comprises, in the 5' to 3' direction: a first adeno-associated virus (AAV) inverted terminal repeat (ITR), a nucleotide sequence of interest (for example an expression cassette as described herein) and a second AAV ITR, where the first ITR (5' ITR) and the second ITR (3' ITR) are symmetric, or substantially symmetrical with respect to each other—that is, a ceDNA vector can comprise ITR sequences that have a symmetrical three-dimensional spatial organization such that their structure is the same shape in geometrical space, or have the same A, C-C' and B-B' loops in 3D space. In such an embodiment, a symmetrical ITR pair, or substantially symmetrical ITR pair can be modified ITRs (e.g., mod-ITRs) that are not wild-type ITRs. A mod-ITR pair can have the same sequence which has one or more modifications from wild-type ITR and are reverse complements (inverted) of each other. In one embodiment of any of the aspects or embodiments herein, a modified ITR pair are substantially symmetrical as defined herein, that is, the modified ITR pair can have a different sequence but have corresponding or the same symmetrical three-dimensional shape. In some embodiments of any of the aspects and embodiments herein, the symmetrical ITRs, or substantially symmetrical ITRs can be wild type (WT-ITRs) as described herein. That is, both ITRs have a wild-type sequence, but do not necessarily have to be WT-ITRs from the same AAV serotype. In one embodiment of any of the aspects or embodiments herein, one WT-ITR can be from one AAV serotype, and the other WT-ITR can be from a different AAV serotype. In such an embodiment, a WT-ITR pair are substantially symmetrical as defined herein, that is, they can have one or more conservative nucleotide modification while still retaining the symmetrical three-dimensional spatial organization.

The wild-type or mutated or otherwise modified ITR sequences provided herein represent DNA sequences included in the expression construct (e.g., ceDNA-plasmid, ceDNA Bacmid, ceDNA-baculovirus) for production of the ceDNA vector. Thus, ITR sequences actually contained in the ceDNA vector produced from the ceDNA-plasmid or other expression construct may or may not be identical to the ITR sequences provided herein as a result of naturally occurring changes taking place during the production process (e.g., replication error).

In one embodiment of any of the aspects or embodiments herein, a ceDNA vector described herein comprising the expression cassette with a transgene which is a therapeutic nucleic acid sequence, can be operatively linked to one or more regulatory sequence(s) that allows or controls expression of the transgene. In one embodiment of any of the aspects or embodiments herein, the polynucleotide comprises a first ITR sequence and a second ITR sequence, wherein the nucleotide sequence of interest is flanked by the first and second ITR sequences, and the first and second ITR sequences are asymmetrical relative to each other, or symmetrical relative to each other.

In one embodiment of any of the aspects or embodiments herein, an expression cassette is located between two ITRs comprised in the following order with one or more of: a promoter operably linked to a transgene, a posttranscriptional regulatory element, and a polyadenylation and termination signal. In one embodiment of any of the aspects or embodiments herein, the promoter is regulatable—inducible or repressible. The promoter can be any sequence that facilitates the transcription of the transgene. In one embodiment of any of the aspects or embodiments herein the promoter is a CAG promoter, or variation thereof. The posttranscriptional regulatory element is a sequence that modulates expression of the transgene, as a non-limiting example, any sequence that creates a tertiary structure that enhances expression of the transgene which is a therapeutic nucleic acid sequence.

In one embodiment of any of the aspects or embodiments herein, the posttranscriptional regulatory element comprises WPRE. In one embodiment of any of the aspects or embodiments herein, the polyadenylation and termination signal comprise BGHpolyA. Any cis regulatory element known in the art, or combination thereof, can be additionally used e.g., SV40 late polyA signal upstream enhancer sequence (USE), or other posttranscriptional processing elements including, but not limited to, the thymidine kinase gene of herpes simplex virus, or hepatitis B virus (HBV). In one embodiment of any of the aspects or embodiments herein, the expression cassette length in the 5' to 3' direction is greater than the maximum length known to be encapsidated in an AAV virion. In one embodiment of any of the aspects or embodiments herein, the length is greater than 4.6 kb, or greater than 5 kb, or greater than 6 kb, or greater than 7 kb. Various expression cassettes are exemplified herein.

In one embodiment of any of the aspects or embodiments herein, the expression cassette can comprise more than 4000 nucleotides, 5000 nucleotides, 10,000 nucleotides or 20,000 nucleotides, or 30,000 nucleotides, or 40,000 nucleotides or 50,000 nucleotides, or any range between about 4000-10,000 nucleotides or 10,000-50,000 nucleotides, or more than 50,000 nucleotides.

In one embodiment of any of the aspects or embodiments herein, the expression cassette can also comprise an internal ribosome entry site (IRES) and/or a 2A element. The cis-regulatory elements include, but are not limited to, a promoter, a riboswitch, an insulator, a mir-regulatable element, a post-transcriptional regulatory element, a tissue- and cell type-specific promoter and an enhancer. In some embodiments of any of the aspects and embodiments herein the ITR can act as the promoter for the transgene. In some embodiments of any of the aspects and embodiments herein, the ceDNA vector comprises additional components to regulate expression of the transgene, for example, a regulatory switch, for controlling and regulating the expression of the transgene, and can include if desired, a regulatory switch which is a kill switch to enable controlled cell death of a cell comprising a ceDNA vector.

In one embodiment of any of the aspects or embodiments herein, ceDNA vectors are capsid-free and can be obtained from a plasmid encoding in this order: a first ITR, expressible transgene cassette and a second ITR, where at least one of the first and/or second ITR sequence is mutated with respect to the corresponding wild type AAV2 ITR sequence.

In one embodiment of any of the aspects or embodiments herein, the ceDNA vectors disclosed herein are used for therapeutic purposes (e.g., for medical, diagnostic, or veterinary uses) or immunogenic polypeptides.

The expression cassette can comprise any transgene which is a therapeutic nucleic acid sequence. In certain embodiments, the ceDNA vector comprises any gene of interest in the subject, which includes one or more polypeptides, peptides, ribozymes, peptide nucleic acids, siRNAs, RNAis, antisense oligonucleotides, antisense polynucleotides, antibodies, antigen binding fragments, or any combination thereof.

In one embodiment of any of the aspects or embodiments herein, sequences provided in the expression cassette, expression construct, or donor sequence of a ceDNA vector described herein can be codon optimized for the host cell. As used herein, the term "codon optimized" or "codon optimization" refers to the process of modifying a nucleic acid sequence for enhanced expression in the cells of the vertebrate of interest, e.g., mouse or human, by replacing at least one, more than one, or a significant number of codons of the native sequence (e.g., a prokaryotic sequence) with codons that are more frequently or most frequently used in the genes of that vertebrate. Various species exhibit particular bias for certain codons of a particular amino acid.

Typically, codon optimization does not alter the amino acid sequence of the original translated protein. Optimized codons can be determined using e.g., Aptagen's Gene Forge® codon optimization and custom gene synthesis platform (Aptagen, Inc., 2190 Fox Mill Rd. Suite 300, Herndon, Va. 20171) or another publicly available database.

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, it is possible to calculate the relative frequencies of codon usage (Nakamura, Y., et al. "Codon usage tabulated from the international DNA sequence databases: status for the year 2000" Nucl. Acids Res. 28:292 (2000)).

Inverted Terminal Repeats (ITRs)

As described herein, the ceDNA vectors are capsid-free, linear duplex DNA molecules formed from a continuous strand of complementary DNA with covalently-closed ends (linear, continuous and non-encapsidated structure), which comprise a 5' inverted terminal repeat (ITR) sequence and a 3' ITR sequence that are different, or asymmetrical with respect to each other. At least one of the ITRs comprises a functional terminal resolution site and a replication protein binding site (RPS) (sometimes referred to as a replicative protein binding site), e.g., a Rep binding site. Generally, the ceDNA vector contains at least one modified AAV inverted terminal repeat sequence (ITR), i.e., a deletion, insertion, and/or substitution with respect to the other ITR, and an expressible transgene.

In one embodiment of any of the aspects or embodiments herein, at least one of the ITRs is an AAV ITR, e.g., a wild type AAV ITR. In one embodiment of any of the aspects or embodiments herein, at least one of the ITRs is a modified ITR relative to the other ITR—that is, the ceDNA comprises ITRs that are asymmetric relative to each other. In one embodiment of any of the aspects or embodiments herein, at least one of the ITRs is a non-functional ITR.

In one embodiment of any of the aspects or embodiments herein, the ceDNA vector comprises: (1) an expression cassette comprising a cis-regulatory element, a promoter and at least one transgene; or (2) a promoter operably linked to at least one transgene, and (3) two self-complementary sequences, e.g., ITRs, flanking said expression cassette, wherein the ceDNA vector is not associated with a capsid protein. In some embodiments of any of the aspects and embodiments herein, the ceDNA vector comprises two self-complementary sequences found in an AAV genome, where at least one comprises an operative Rep-binding element (RBE) and a terminal resolution site (TRS) of AAV or a functional variant of the RBE, and one or more cis-regulatory elements operatively linked to a transgene. In some embodiments of any of the aspects and embodiments herein, the ceDNA vector comprises additional components to regulate expression of the transgene, for example, regulatory switches for controlling and regulating the expression of the transgene, and can include a regulatory switch which is a kill switch to enable controlled cell death of a cell comprising a ceDNA vector.

In one embodiment of any of the aspects or embodiments herein, the two self-complementary sequences can be ITR sequences from any known parvovirus, for example a dependovirus such as AAV (e.g., AAV1-AAV12). Any AAV serotype can be used, including but not limited to a modified AAV2 ITR sequence, that retains a Rep-binding site (RBS) such as 5'-GCGCGCTCGCTCGCTC-3'(SEQ ID NO: 1) and a terminal resolution site (TRS) in addition to a variable palindromic sequence allowing for hairpin secondary structure formation. In some embodiments of any of the aspects and embodiments herein, an ITR may be synthetic. In one embodiment of any of the aspects or embodiments herein, a synthetic ITR is based on ITR sequences from more than one AAV serotype. In another embodiment, a synthetic ITR includes no AAV-based sequence. In yet another embodiment, a synthetic ITR preserves the ITR structure described above although having only some or no AAV-sourced sequence. In some aspects a synthetic ITR may interact preferentially with a wildtype Rep or a Rep of a specific serotype, or in some instances will not be recognized by a wild-type Rep and be recognized only by a mutated Rep. In some embodiments of any of the aspects and embodiments herein, the ITR is a synthetic ITR sequence that retains a functional Rep-binding site (RBS) such as 5'-GCGCGCTCGCTCGCTC-3' (SEQ ID NO: 1) and a terminal resolution site (TRS) in addition to a variable palindromic sequence allowing for hairpin secondary structure formation. In some examples, a modified ITR sequence retains the sequence of the RBS, TRS and the structure and position of a Rep binding element forming the terminal loop portion of one of the ITR hairpin secondary structure from the corresponding sequence of the wild-type AAV2 ITR. Exemplary ITR sequences for use in the ceDNA vectors are disclosed in Tables 2-9, 10A and 10B, SEQ ID NO: 2, 52, 101-449 and 545-547, and the partial ITR sequences shown in FIGS. 26A-26B of PCT application No. PCT/US 18/49996, filed Sep. 7, 2018. In some embodiments of any of the aspects and embodiments herein, a ceDNA vector can comprise an ITR with a modification in the ITR corresponding to any of the modifications in ITR sequences or ITR partial sequences shown in any one or more of Tables 2, 3, 4, 5, 6, 7, 8, 9, 10A and 10B PCT application No. PCT/US 18/49996, filed Sep. 7, 2018.

In one embodiment of any of the aspects or embodiments herein, the ceDNA vectors can be produced from expression constructs that further comprise a specific combination of cis-regulatory elements. The cis-regulatory elements include, but are not limited to, a promoter, a riboswitch, an insulator, a mir-regulatable element, a post-transcriptional regulatory element, a tissue- and cell type-specific promoter and an enhancer. In some embodiments of any of the aspects and embodiments herein the ITR can act as the promoter for the transgene. In some embodiments of any of the aspects and embodiments herein, the ceDNA vector comprises additional components to regulate expression of the transgene, for example, regulatory switches as described in PCT application No. PCT/US 18/49996, filed Sep. 7, 2018, to regulate the expression of the transgene or a kill switch, which can kill a cell comprising the ceDNA vector.

In one embodiment of any of the aspects or embodiments herein, the expression cassettes can also include a post-transcriptional element to increase the expression of a transgene. In one embodiment of any of the aspects or embodiments herein, Woodchuck Hepatitis Virus (WHP) posttranscriptional regulatory element (WPRE) is used to increase the expression of a transgene. Other posttranscriptional processing elements such as the post-transcriptional element from the thymidine kinase gene of herpes simplex virus, or hepatitis B virus (HBV) can be used. Secretory sequences can be linked to the transgenes, e.g., VH-02 and VK-A26 sequences. The expression cassettes can include a poly-adenylation sequence known in the art or a variation thereof, such as a naturally occurring sequence isolated from bovine BGHpA or a virus SV40pA, or a synthetic sequence. Some expression cassettes can also include SV40 late polyA signal upstream enhancer (USE) sequence. The USE can be used in combination with SV40pA or heterologous poly-A signal.

FIGS. 1A-1C of International Application No. PCT/US2018/050042, filed on Sep. 7, 2018 and incorporated by reference in its entirety herein, show schematics of nonlimiting, exemplary ceDNA vectors, or the corresponding sequence of ceDNA plasmids. ceDNA vectors are capsid-free and can be obtained from a plasmid encoding in this order: a first ITR, expressible transgene cassette and a second ITR, where at least one of the first and/or second ITR sequence is mutated with respect to the corresponding wild type AAV2 ITR sequence. The expressible transgene cassette preferably includes one or more of, in this order: an enhancer/promoter, an ORF reporter (transgene), a post-transcription regulatory element (e.g., WPRE), and a poly-adenylation and termination signal (e.g., BGH polyA).

Promoters

Suitable promoters, including those described above, can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVTE), a rous sarcoma virus (RSV) promoter, a human U6 small nuclear promoter (U6, e.g., (Miyagishi el al., Nature Biotechnology 20, 497-500 (2002)), an enhanced U6 promoter (e.g., Xia et al., Nucleic Acids Res. 2003 Sep. 1; 31(17)), a human H1 promoter (H1), a CAG promoter, a human alpha 1-antitrypsin (HAAT) promoter (e.g., and the like). In one embodiment of any of the aspects or embodiments herein, these promoters are altered at their downstream intron containing end to include one or more nuclease cleavage sites. In one embodiment of any of the aspects or embodiments herein, the DNA containing the nuclease cleavage site(s) is foreign to the promoter DNA.

In one embodiment of any of the aspects or embodiments herein, a promoter may comprise one or more specific transcriptional regulatory sequences to further enhance expression and/or to alter the spatial expression and/or temporal expression of same. A promoter may also comprise distal enhancer or repressor elements, which may be located as much as several thousand base pairs from the start site of transcription. A promoter may be derived from sources including viral, bacterial, fungal, plants, insects, and animals. A promoter may regulate the expression of a gene component constitutively, or differentially with respect to the cell, tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter, as well as the promoters listed below.

Such promoters and/or enhancers can be used for expression of any gene of interest, e.g., therapeutic proteins). For example, the vector may comprise a promoter that is operably linked to the nucleic acid sequence encoding a therapeutic protein. In one embodiment of any of the aspects or embodiments herein, the promoter operably linked to the therapeutic protein coding sequence may be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. In one embodiment of any of the aspects or embodiments herein, the promoter may also be a promoter from a human gene such as human ubiquitin C (hUbC), human actin, human myosin, human hemoglobin, human muscle creatine, or human metallothionein. The promoter may also be a tissue specific promoter, such as a liver specific promoter, such as human alpha 1-antitrypsin (HAAT) or transthyretin (TTR), natural or synthetic. In one embodiment of any of the aspects or embodiments herein, delivery to the liver can be achieved using endogenous ApoE specific targeting of the composition comprising a ceDNA vector to hepatocytes via the low-density lipoprotein (LDL) receptor present on the surface of the hepatocyte.

In one embodiment of any of the aspects or embodiments herein, the promoter used is the native promoter of the gene encoding the therapeutic protein. The promoters and other regulatory sequences for the respective genes encoding the therapeutic proteins are known and have been characterized. The promoter region used may further include one or more additional regulatory sequences (e.g., native) such as enhancers (e.g., Serpin Enhancer) known in the art.

Non-limiting examples of suitable promoters for use in accordance with the present invention include the CAG promoter of, for example, the HAAT promoter, the human EF1-α promoter or a fragment of the EF1-α promoter and the rat EF1-α promoter.

Polyadenylation Sequences

A sequence encoding a polyadenylation sequence can be included in the ceDNA vector to stabilize the mRNA expressed from the ceDNA vector, and to aid in nuclear export and translation. In one embodiment of any of the aspects or embodiments herein, the ceDNA vector does not include a polyadenylation sequence. In other embodiments, the vector includes at least 1, at least 2, at least 3, at least 4, at least 5, at least 10, at least 15, at least 20, at least 25, at least 30, at least 40, at least 45, at least 50 or more adenine dinucleotides. In some embodiments of any of the aspects and embodiments herein, the polyadenylation sequence comprises about 43 nucleotides, about 40-50 nucleotides, about 40-55 nucleotides, about 45-50 nucleotides, about 35-50 nucleotides, or any range there between.

In one embodiment of any of the aspects or embodiments herein, the ceDNA can be obtained from a vector polynucleotide that encodes a heterologous nucleic acid operatively positioned between two different inverted terminal repeat sequences (ITRs) (e.g. AAV ITRs), wherein at least one of the ITRs comprises a terminal resolution site and a replicative protein binding site (RPS), e.g. a Rep binding site (e.g. wt AAV ITR), and one of the ITRs comprises a deletion, insertion, and/or substitution with respect to the other ITR, e.g., functional ITR.

In one embodiment of any of the aspects or embodiments herein, the host cells do not express viral capsid proteins and the polynucleotide vector template is devoid of any viral capsid coding sequences. In one embodiment of any of the aspects or embodiments herein, the polynucleotide vector template is devoid of AAV capsid genes but also of capsid genes of other viruses). In one embodiment of any of the aspects or embodiments herein, the nucleic acid molecule is also devoid of AAV Rep protein coding sequences. Accordingly, in some embodiments of any of the aspects and embodiments herein, the nucleic acid molecule of the invention is devoid of both functional AAV cap and AAV rep genes.

In one embodiment of any of the aspects or embodiments herein, the ceDNA vector does not have a modified ITRs.

In one embodiment of any of the aspects or embodiments herein, the ceDNA vector comprises a regulatory switch as disclosed herein (or in PCT application No. PCT/US 18/49996, filed Sep. 7, 2018).

IV. Production of a ceDNA Vector

Methods for the production of a ceDNA vector as described herein comprising an asymmetrical ITR pair or symmetrical ITR pair as defined herein is described in section IV of PCT/US 18/49996 filed Sep. 7, 2018, which is incorporated herein in its entirety by reference. As described herein, the ceDNA vector can be obtained, for example, by the process comprising the steps of: a) incubating a population of host cells (e.g. insect cells) harboring the polynucleotide expression construct template (e.g., a ceDNA-plasmid, a ceDNA-Bacmid, and/or a ceDNA-baculovirus), which is devoid of viral capsid coding sequences, in the presence of a Rep protein under conditions effective and for a time sufficient to induce production of the ceDNA vector within the host cells, and wherein the host cells do not comprise viral capsid coding sequences; and b) harvesting and isolating the ceDNA vector from the host cells. The presence of Rep protein induces replication of the vector polynucleotide with a modified ITR to produce the ceDNA vector in a host cell.

However, no viral particles (e.g. AAV virions) are expressed. Thus, there is no size limitation such as that naturally imposed in AAV or other viral-based vectors.

The presence of the ceDNA vector isolated from the host cells can be confirmed by digesting DNA isolated from the host cell with a restriction enzyme having a single recognition site on the ceDNA vector and analyzing the digested DNA material on a non-denaturing gel to confirm the presence of characteristic bands of linear and continuous DNA as compared to linear and non-continuous DNA.

In one embodiment of any of the aspects or embodiments herein, the invention provides for use of host cell lines that have stably integrated the DNA vector polynucleotide expression template (ceDNA template) into their own genome in production of the non-viral DNA vector, e.g. as described in Lee, L. et al. (2013) Plos One 8(8): e69879. Preferably, Rep is added to host cells at an MOI of about 3. When the host cell line is a mammalian cell line, e.g., HEK293 cells, the cell lines can have polynucleotide vector template stably integrated, and a second vector such as herpes virus can be used to introduce Rep protein into cells, allowing for the excision and amplification of ceDNA in the presence of Rep and helper virus.

In one embodiment of any of the aspects or embodiments herein, the host cells used to make the ceDNA vectors described herein are insect cells, and baculovirus is used to deliver both the polynucleotide that encodes Rep protein and the non-viral DNA vector polynucleotide expression construct template for ceDNA. In some embodiments of any of the aspects and embodiments herein, the host cell is engineered to express Rep protein.

The ceDNA vector is then harvested and isolated from the host cells. The time for harvesting and collecting ceDNA vectors described herein from the cells can be selected and optimized to achieve a high-yield production of the ceDNA vectors. For example, the harvest time can be selected in view of cell viability, cell morphology, cell growth, etc. In one embodiment of any of the aspects or embodiments herein, cells are grown under sufficient conditions and harvested a sufficient time after baculoviral infection to produce ceDNA vectors but before most cells start to die due to the baculoviral toxicity. The DNA vectors can be isolated using plasmid purification kits such as Qiagen Endo-Free Plasmid kits. Other methods developed for plasmid isolation can be also adapted for DNA vectors. Generally, any nucleic acid purification methods can be adopted.

The DNA vectors can be purified by any means known to those of skill in the art for purification of DNA. In one embodiment of any of the aspects or embodiments herein, ceDNA vectors are purified as DNA molecules. In one embodiment of any of the aspects or embodiments herein, the ceDNA vectors are purified as exosomes or microparticles. The presence of the ceDNA vector can be confirmed by digesting the vector DNA isolated from the cells with a restriction enzyme having a single recognition site on the DNA vector and analyzing both digested and undigested DNA material using gel electrophoresis to confirm the presence of characteristic bands of linear and continuous DNA as compared to linear and non-continuous DNA.

V. Preparation of Lipid Particles

Lipid particles (e.g., lipid nanoparticles) can form spontaneously upon mixing of TNA (e.g., ceDNA) and the lipid(s). Depending on the desired particle size distribution, the resultant nanoparticle mixture can be extruded through a membrane (e.g., 100 nm cut-off) using, for example, a thermobarrel extruder, such as Lipex Extruder (Northern Lipids, Inc). In some cases, the extrusion step can be omitted. Ethanol removal and simultaneous buffer exchange can be accomplished by, for example, dialysis or tangential flow filtration.

Generally, lipid particles (e.g., lipid nanoparticles) can be formed by any method known in the art. For example, the lipid particles (e.g., lipid nanoparticles) can be prepared by the methods described, for example, in US2013/0037977, US2010/0015218, US2013/0156845, US2013/0164400, US2012/0225129, and US2010/0130588, content of each of which is incorporated herein by reference in its entirety. In some embodiments of any of the aspects and embodiments herein, lipid particles (e.g., lipid nanoparticles) can be prepared using a continuous mixing method, a direct dilution process, or an in-line dilution process. The processes and apparatuses for apparatuses for preparing lipid nanoparticles using direct dilution and in-line dilution processes are described in US2007/0042031, the content of which is incorporated herein by reference in its entirety. The processes and apparatuses for preparing lipid nanoparticles using step-wise dilution processes are described in US2004/0142025, the content of which is incorporated herein by reference in its entirety.

In one embodiment of any of the aspects or embodiments herein, the lipid particles (e.g., lipid nanoparticles) can be prepared by an impinging jet process. Generally, the particles are formed by mixing lipids dissolved in alcohol (e.g., ethanol) with ceDNA dissolved in a buffer, e.g, a citrate buffer, a sodium acetate buffer, a sodium acetate and magnesium chloride buffer, a malic acid buffer, a malic acid and sodium chloride buffer, or a sodium citrate and sodium chloride buffer. The mixing ratio of lipids to ceDNA can be about 45-55% lipid and about 65-45% ceDNA.

The lipid solution can contain a disclosed ionizable lipid, a non-cationic lipid (e.g., a phospholipid, such as DSPC, DOPE, and DOPC), PEG-lipid conjugated molecule (e.g., PEG-lipid), and a sterol (e.g., cholesterol) at a total lipid concentration of 5-30 mg/mL, more likely 5-15 mg/mL, most likely 9-12 mg/mL in an alcohol, e.g., in ethanol. In the lipid solution, mol ratio of the lipids can range from about 25-98% for the cationic lipid, preferably about 35-65%; about 0-15% for the non-ionic lipid, preferably about 0-12%; about 0-15% for the PEG-lipid conjugated lipid molecule, preferably about 1-6%; and about 0-75% for the sterol, preferably about 30-50%.

The ceDNA solution can comprise the ceDNA at a concentration range from 0.3 to 1.0 mg/mL, preferably 0.3-0.9 mg/mL in buffered solution, with pH in the range of 3.5-5.

For forming the LNPs, in one exemplary but nonlimiting embodiment, the two liquids are heated to a temperature in the range of about 15-40° C., preferably about 30-40° C., and then mixed, for example, in an impinging jet mixer, instantly forming the LNP. The mixing flow rate can range from 10-600 mL/min. The tube ID can have a range from 0.25 to 1.0 mm and a total flow rate from 10-600 mL/min. The combination of flow rate and tubing ID can have the effect of controlling the particle size of the LNPs between 30 and 200 nm. The solution can then be mixed with a buffered solution at a higher pH with a mixing ratio in the range of 1:1 to 1:3 vol:vol, preferably about 1:2 vol:vol. If needed this buffered solution can be at a temperature in the range of 15-40° C. or 30-40° C. The mixed LNPs can then undergo an anion exchange filtration step. Prior to the anion exchange, the mixed LNPs can be incubated for a period of time, for example 30 mins to 2 hours. The temperature during incubating can be in the range of 15-40° C. or 30-40° C. After incubating the solution is filtered through a filter, such as a 0.8 µm filter, containing an anion exchange separation step. This process can use tubing IDs ranging from 1 mm ID to 5 mm ID and a flow rate from 10 to 2000 mL/min.

After formation, the LNPs can be concentrated and diafiltered via an ultrafiltration process where the alcohol is removed and the buffer is exchanged for the final buffer solution, for example, phosphate buffered saline (PBS) at about pH 7, e.g., about pH 6.9, about pH 7.0, about pH 7.1, about pH 7.2, about pH 7.3, or about pH 7.4.

The ultrafiltration process can use a tangential flow filtration format (TFF) using a membrane nominal molecular weight cutoff range from 30-500 kD. The membrane format is hollow fiber or flat sheet cassette. The TFF processes with the proper molecular weight cutoff can retain the LNP in the retentate and the filtrate or permeate contains the alcohol; citrate buffer and final buffer wastes. The TFF process is a multiple step process with an initial concentration to a ceDNA concentration of 1-3 mg/mL. Following concentration, the LNPs solution is diafiltered against the final buffer for 10-20 volumes to remove the alcohol and perform buffer exchange. The material can then be concentrated an additional 1-3-fold. The concentrated LNP solution can be sterile filtered.

VI. Pharmaceutical Compositions and Formulations

Also provided herein is a pharmaceutical composition comprising the TNA lipid particle and a pharmaceutically acceptable carrier or excipient.

In one embodiment of any of the aspects or embodiments herein, the TNA lipid particles (e.g., lipid nanoparticles) are provided with full encapsulation, partial encapsulation of the therapeutic nucleic acid. In one embodiment of any of the aspects or embodiments herein, the nucleic acid therapeutics is fully encapsulated in the lipid particles (e.g., lipid nanoparticles) to form a nucleic acid containing lipid particle. In one embodiment of any of the aspects or embodiments herein, the nucleic acid may be encapsulated within the lipid portion of the particle, thereby protecting it from enzymatic degradation.

In one embodiment of any of the aspects or embodiments herein, the lipid particle has a mean diameter from about 20 nm to about 100 nm, 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm to ensure effective delivery. Nucleic acid containing lipid particles (e.g., lipid nanoparticles) and their method of preparation are disclosed in, e.g., PCT/US18/50042, U.S. Patent Publication Nos. 20040142025 and 20070042031, the disclosures of which are herein incorporated by reference in their entirety for all purposes. In one embodiment of any of the aspects or embodiments herein, lipid particle (e.g., lipid nanoparticle) size can be determined by quasi-elastic light scattering using, for example, a Malvern Zetasizer Nano ZS (Malvern, UK) system.

Generally, the lipid particles (e.g., lipid nanoparticles) of the invention have a mean diameter selected to provide an intended therapeutic effect.

Depending on the intended use of the lipid particles (e.g., lipid nanoparticles), the proportions of the components can be varied and the delivery efficiency of a particular formulation can be measured using, for example, an endosomal release parameter (ERP) assay.

In one embodiment of any of the aspects or embodiments herein, the lipid particles (e.g., lipid nanoparticles) may be conjugated with other moieties to prevent aggregation. Such lipid conjugates include, but are not limited to, PEG-lipid conjugates such as, e.g., PEG coupled to dialkyloxypropyls (e.g., PEG-DAA conjugates), PEG coupled to diacylglycerols (e.g., PEG-DAG conjugates), PEG coupled to cholesterol, PEG coupled to phosphatidylethanolamines, and PEG conjugated to ceramides (see, e.g., U.S. Pat. No. 5,885,613), cationic PEG lipids, polyoxazoline (POZ)-lipid conjugates (e.g., POZ-DAA conjugates; see, e.g., U.S. Provisional Application No. 61/294,828, filed Jan. 13, 2010, and U.S. Provisional Application No. 61/295,140, filed Jan. 14, 2010), polyamide oligomers (e.g., ATTA-lipid conjugates), and mixtures thereof. Additional examples of POZ-lipid conjugates are described in PCT Publication No. WO 2010/006282. PEG or POZ can be conjugated directly to the lipid or may be linked to the lipid via a linker moiety. Any linker moiety suitable for coupling the PEG or the POZ to a lipid can be used including, e.g., non-ester containing linker moieties and ester-containing linker moieties. In certain preferred embodiments, non-ester containing linker moieties, such as amides or carbamates, are used. The disclosures of each of the above patent documents are herein incorporated by reference in their entirety for all purposes.

In one embodiment of any of the aspects or embodiments herein, the ceDNA can be complexed with the lipid portion of the particle or encapsulated in the lipid position of the lipid particle (e.g., lipid nanoparticle). In one embodiment of any of the aspects or embodiments herein, the ceDNA can be fully encapsulated in the lipid position of the lipid particle (e.g., lipid nanoparticle), thereby protecting it from degradation by a nuclease, e.g., in an aqueous solution. In one embodiment of any of the aspects or embodiments herein, the ceDNA in the lipid particle (e.g., lipid nanoparticle) is not substantially degraded after exposure of the lipid particle (e.g., lipid nanoparticle) to a nuclease at 37° C. for at least about 20, 30, 45, or 60 minutes. In some embodiments of any of the aspects and embodiments herein, the ceDNA in the lipid particle (e.g., lipid nanoparticle) is not substantially degraded after incubation of the particle in serum at 37° C. for at least about 30, 45, or 60 minutes or at least about 2, 3, 4, 5, 6, 7, 8, 9, 10, 12, 14, 16, 18, 20, 22, 24, 26, 28, 30, 32, 34, or 36 hours.

In one embodiment of any of the aspects or embodiments herein, the lipid particles (e.g., lipid nanoparticles) are substantially non-toxic to a subject, e.g., to a mammal such as a human.

In one embodiment of any of the aspects or embodiments herein, a pharmaceutical composition comprising a therapeutic nucleic acid of the present disclosure may be formulated in lipid particles (e.g., lipid nanoparticles). In some embodiments of any of the aspects and embodiments herein, the lipid particle comprising a therapeutic nucleic acid can be formed from a disclosed ionizable lipid. In some other embodiments, the lipid particle comprising a therapeutic nucleic acid can be formed from non-cationic lipid. In a preferred embodiment, the lipid particle of the invention is a nucleic acid containing lipid particle, which is formed from a disclosed ionizable lipid comprising a therapeutic nucleic acid selected from the group consisting of mRNA, antisense RNA and oligonucleotide, ribozymes, aptamer, interfering RNAs (RNAi), Dicer-substrate dsRNA, small hairpin RNA (shRNA), asymmetrical interfering RNA (aiRNA), microRNA (miRNA), minicircle DNA, minigene, viral DNA (e.g., Lentiviral or AAV genome) or non-viral synthetic DNA vectors, closed-ended linear duplex DNA (ceDNA/CELiD), plasmids, bacmids, Doggybone™ DNA vectors, minimalistic immunological-defined gene expression (MIDGE)-vector, nonviral ministring DNA vector (linear-covalently closed DNA vector), or dumbbell-shaped DNA minimal vector ("dumbbell DNA").

In another preferred embodiment, the lipid particle of the invention is a nucleic acid containing lipid particle, which is formed from a non-cationic lipid, and optionally a conjugated lipid that prevents aggregation of the particle.

In one embodiment of any of the aspects or embodiments herein, the lipid particle formulation is an aqueous solution. In one embodiment of any of the aspects or embodiments herein, the lipid particle (e.g., lipid nanoparticle) formulation is a lyophilized powder.

According to some aspects, the disclosure provides for a lipid particle formulation further comprising one or more pharmaceutical excipients. In one embodiment of any of the aspects or embodiments herein, the lipid particle (e.g., lipid nanoparticle) formulation further comprises sucrose, tris, trehalose and/or glycine.

In one embodiment of any of the aspects or embodiments herein, the lipid particles (e.g., lipid nanoparticles) disclosed herein can be incorporated into pharmaceutical compositions suitable for administration to a subject for in vivo delivery to cells, tissues, or organs of the subject. Typically, the pharmaceutical composition comprises the TNA lipid particles (e.g., lipid nanoparticles) disclosed herein and a pharmaceutically acceptable carrier. In one embodiment of any of the aspects or embodiments herein, the TNA lipid particles (e.g., lipid nanoparticles) of the disclosure can be incorporated into a pharmaceutical composition suitable for a desired route of therapeutic administration (e.g., parenteral administration). Passive tissue transduction via high pressure intravenous or intraarterial infusion, as well as intracellular injection, such as intranuclear microinjection or intracytoplasmic injection, are also contemplated. Pharmaceutical compositions for therapeutic purposes can be formulated as a solution, microemulsion, dispersion, liposomes, or other ordered structure suitable for high ceDNA vector concentration. Sterile injectable solutions can be prepared by incorporating the ceDNA vector compound in the required amount in an appropriate buffer with one or a combination of ingredients enumerated above, as required, followed by filtered sterilization.

A lipid particle as disclosed herein can be incorporated into a pharmaceutical composition suitable for topical, systemic, intra-amniotic, intrathecal, intracranial, intraarterial, intravenous, intralymphatic, intraperitoneal, subcutaneous, tracheal, intra-tissue (e.g., intramuscular, intracardiac, intrahepatic, intrarenal, intracerebral), intrathecal, intravesical, conjunctival (e.g., extra-orbital, intraorbital, retroorbital, intraretinal, subretinal, choroidal, sub-choroidal, intrastromal, intracameral and intravitreal), intracochlear, and mucosal (e.g., oral, rectal, nasal) administration. Passive tissue transduction via high pressure intravenous or intraarterial infusion, as well as intracellular injection, such as intranuclear microinjection or intracytoplasmic injection, are also contemplated.

Pharmaceutically active compositions comprising TNA lipid particles (e.g., lipid nanoparticles) can be formulated to deliver a transgene in the nucleic acid to the cells of a recipient, resulting in the therapeutic expression of the transgene therein. The composition can also include a pharmaceutically acceptable carrier.

Pharmaceutical compositions for therapeutic purposes are typically sterile and stable under the conditions of manufacture and storage. The composition can be formulated as a solution, microemulsion, dispersion, liposomes, or other ordered structure suitable to high ceDNA vector concentration. Sterile injectable solutions can be prepared by incorporating the ceDNA vector compound in the required amount in an appropriate buffer with one or a combination of ingredients enumerated above, as required, followed by filtered sterilization.

In one embodiment of any of the aspects or embodiments herein, lipid particles (e.g., lipid nanoparticles) are solid core particles that possess at least one lipid bilayer. In one embodiment of any of the aspects or embodiments herein, the lipid particles (e.g., lipid nanoparticles) have a non-bilayer structure, i.e., a non-lamellar (i.e., non-bilayer) morphology. Without limitations, the non-bilayer morphology can include, for example, three dimensional tubes, rods, cubic symmetries, etc. The non-lamellar morphology (i.e., non-bilayer structure) of the lipid particles (e.g., lipid nanoparticles) can be determined using analytical techniques known to and used by those of skill in the art. Such techniques include, but are not limited to, Cryo-Transmission Electron Microscopy ("Cryo-TEM"), Differential Scanning calorimetry ("DSC"), X-Ray Diffraction, and the like. For example, the morphology of the lipid particles (lamellar vs. non-lamellar) can readily be assessed and characterized using, e.g., Cryo-TEM analysis as described in US2010/0130588, the content of which is incorporated herein by reference in its entirety.

In one embodiment of any of the aspects or embodiments herein, the lipid particles (e.g., lipid nanoparticles) having a non-lamellar morphology are electron dense.

In one embodiment of any of the aspects or embodiments herein, the disclosure provides for a lipid particle (e.g., lipid nanoparticle) that is either unilamellar or multilamellar in structure. In some aspects, the disclosure provides for a lipid particle (e.g., lipid nanoparticle) formulation that comprises multi-vesicular particles and/or foam-based particles. By controlling the composition and concentration of the lipid components, one can control the rate at which the lipid conjugate exchanges out of the lipid particle and, in turn, the rate at which the lipid particle (e.g., lipid nanoparticle) becomes fusogenic. In addition, other variables including, for example, pH, temperature, or ionic strength, can be used to vary and/or control the rate at which the lipid particle (e.g., lipid nanoparticle) becomes fusogenic. Other methods which can be used to control the rate at which the lipid particle (e.g., lipid nanoparticle) becomes fusogenic will be apparent to those of ordinary skill in the art based on this disclosure. It will also be apparent that by controlling the composition and concentration of the lipid conjugate, one can control the lipid particle size.

In one embodiment of any of the aspects or embodiments herein, the pKa of formulated ionizable lipids can be correlated with the effectiveness of the LNPs for delivery of nucleic acids (see Jayaraman et al., Angewandte Chemie, International Edition (2012), 51(34), 8529-8533; Semple et al., Nature Biotechnology 28, 172-176 (2010), both of which are incorporated by reference in their entireties). In one embodiment of any of the aspects or embodiments herein, the preferred range of pKa is about 5 to about 8. In one embodiment of any of the aspects or embodiments herein, the preferred range of pKa is about 6 to about 7. In one embodiment of any of the aspects or embodiments herein, the preferred pKa is about 6.5. In one embodiment of any of the aspects or embodiments herein, the pKa of the ionizable lipid can be determined in lipid particles (e.g., lipid nanoparticles) using an assay based on fluorescence of 2-(p-toluidino)-6-napthalene sulfonic acid (TNS).

In one embodiment of any of the aspects or embodiments herein, encapsulation of ceDNA in lipid particles (e.g., lipid nanoparticles) can be determined by performing a membrane-impermeable fluorescent dye exclusion assay, which uses a dye that has enhanced fluorescence when associated with nucleic acid, for example, an Oligreen® assay or PicoGreen® assay. Generally, encapsulation is determined by adding the dye to the lipid particle formulation, measuring the resulting fluorescence, and comparing it to the fluorescence observed upon addition of a small amount of nonionic detergent. Detergent-mediated disruption of the lipid bilayer releases the encapsulated ceDNA, allowing it to interact with the membrane-impermeable dye. Encapsulation of ceDNA can be calculated as $E=(Io-I)/Io$, where I and Io refers to the fluorescence intensities before and after the addition of detergent.

Unit Dosage

In one embodiment of any of the aspects or embodiments herein, the pharmaceutical compositions can be presented in unit dosage form. A unit dosage form will typically be adapted to one or more specific routes of administration of the pharmaceutical composition. In some embodiments of any of the aspects and embodiments herein, the unit dosage form is adapted for administration by inhalation. In some embodiments of any of the aspects and embodiments herein, the unit dosage form is adapted for administration by a vaporizer. In some embodiments of any of the aspects and embodiments herein, the unit dosage form is adapted for administration by a nebulizer. In some embodiments of any of the aspects and embodiments herein, the unit dosage form is adapted for administration by an aerosolizer. In some embodiments of any of the aspects and embodiments herein, the unit dosage form is adapted for oral administration, for buccal administration, or for sublingual administration. In some embodiments of any of the aspects and embodiments herein, the unit dosage form is adapted for intravenous, intramuscular, or subcutaneous administration. In some embodiments of any of the aspects and embodiments herein, the unit dosage form is adapted for intrathecal or intracerebroventricular administration. In some embodiments of any of the aspects and embodiments herein, the pharmaceutical composition is formulated for topical administration. The amount of active ingredient which can be combined with a carrier material to produce a single dosage form will generally be that amount of the compound which produces a therapeutic effect.

VII. Methods of Treatment

The ionizable lipid composition and methods (e.g., TNA lipid particles (e.g., lipid nanoparticles) as described herein) described herein can be used to introduce a nucleic acid sequence (e.g., a therapeutic nucleic acid sequence) in a host cell. In one embodiment of any of the aspects or embodiments herein, introduction of a nucleic acid sequence in a host cell using the TNA LNP (e.g., ceDNA vector lipid particles (e.g., lipid nanoparticles) as described herein) can be monitored with appropriate biomarkers from treated patients to assess gene expression.

The LNP compositions provided herein can be used to deliver a transgene (a nucleic acid sequence) for various purposes. In one embodiment of any of the aspects or embodiments herein, the ceDNA vectors (e.g., ceDNA vector lipid particles (e.g., lipid nanoparticles) as described herein) can be used in a variety of ways, including, for example, ex situ, in vitro and in vivo applications, methodologies, diagnostic procedures, and/or gene therapy regimens.

Provided herein are methods of treating a disease or disorder in a subject comprising introducing into a target cell in need thereof (for example, a liver cell, a muscle cell, a kidney cell, a neuronal cell, or other affected cell type) of the subject a therapeutically effective amount of TNA LNP (e.g., ceDNA vector lipid particles (e.g., lipid nanoparticles) as described herein), optionally with a pharmaceutically acceptable carrier. The TNA LNP (e.g., ceDNA vector lipid particles (e.g., lipid nanoparticles) as described herein) implemented comprises a nucleotide sequence of interest useful for treating the disease. In particular, the TNA may comprise a desired exogenous DNA sequence operably linked to control elements capable of directing transcription of the desired polypeptide, protein, or oligonucleotide encoded by the exogenous DNA sequence when introduced into the subject. The TNA LNP (e.g., ceDNA vector lipid particles (e.g., lipid nanoparticles) as described herein) can be administered via any suitable route as described herein and known in the art. In one embodiment of any of the aspects or embodiments herein, the target cells are in a human subject.

Provided herein are methods for providing a subject in need thereof with a diagnostically- or therapeutically-effective amount of TNA LNP (e.g., ceDNA vector lipid particles (e.g., lipid nanoparticles) as described herein), the method comprising providing to a cell, tissue or organ of a subject in need thereof, an amount of the TNA LNP (e.g., ceDNA vector lipid particles (e.g., lipid nanoparticles) as described herein); and for a time effective to enable expression of the transgene from the TNA LNP thereby providing the subject with a diagnostically- or a therapeutically-effective amount of the protein, peptide, nucleic acid expressed by the TNA LNP (e.g., ceDNA vector lipid particles (e.g., lipid nanoparticles) as described herein). In one embodiment of any of the aspects or embodiments herein, the subject is human.

Provided herein are methods for diagnosing, preventing, treating, or ameliorating at least one or more symptoms of a disease, a disorder, a dysfunction, an injury, an abnormal condition, or trauma in a subject. Generally, the method includes at least the step of administering to a subject in need thereof TNA LNP (e.g., ceDNA vector lipid particles (e.g., lipid nanoparticles) as described herein), in an amount and for a time sufficient to diagnose, prevent, treat or ameliorate the one or more symptoms of the disease, disorder, dysfunction, injury, abnormal condition, or trauma in the subject. In one embodiment of any of the aspects or embodiments herein, the subject is human.

Provided herein are methods for using the TNA LNP as a tool for treating one or more symptoms of a disease or disease states. There are a number of inherited diseases in which defective genes are known, and typically fall into two classes: deficiency states, usually of enzymes, which are generally inherited in a recessive manner, and unbalanced states, which may involve regulatory or structural proteins, and which are typically but not always inherited in a dominant manner. For deficiency state diseases, TNA LNP (e.g., ceDNA vector lipid particles (e.g., lipid nanoparticles) as described herein) can be used to deliver transgenes to bring a normal gene into affected tissues for replacement therapy, as well, in some embodiments of any of the aspects and embodiments herein, to create animal models for the disease using antisense mutations. For unbalanced disease states, TNA LNP (e.g., ceDNA vector lipid particles) can be used to create a disease state in a model system, which could then be used in efforts to counteract the disease state. Thus, the TNA LNP (e.g., ceDNA vector lipid particles (e.g., lipid nanoparticles)) and methods disclosed herein permit the treatment of genetic diseases. As used herein, a disease state is treated by partially or wholly remedying the deficiency or imbalance that causes the disease or makes it more severe.

In general, the TNA LNP (e.g., ceDNA vector lipid particles (e.g., lipid nanoparticles)) can be used to deliver any transgene in accordance with the description above to treat, prevent, or ameliorate the symptoms associated with any disorder related to gene expression. Illustrative disease states include, but are not-limited to: cystic fibrosis (and other diseases of the lung), hemophilia A, hemophilia B, thalassemia, anemia and other blood disorders, AIDS, Alzheimer's disease, Parkinson's disease, Huntington's disease, amyotrophic lateral sclerosis, epilepsy, and other neurological disorders, cancer, diabetes mellitus, muscular dystrophies (e.g., Duchenne, Becker), Hurler's disease, adenosine deaminase deficiency, metabolic defects, retinal degenerative diseases (and other diseases of the eye), mitochondriopathies (e.g., Leber's hereditary optic neuropathy (LHON), Leigh syndrome, and subacute sclerosing encephalopathy), myopathies (e.g., facioscapulohumeral myopathy (FSHD) and cardiomyopathies), diseases of solid organs (e.g., brain, liver, kidney, heart), and the like. In some embodiments of any of the aspects and embodiments herein, the ceDNA vectors as disclosed herein can be advantageously used in the treatment of individuals with metabolic disorders (e.g., ornithine transcarbamylase deficiency).

In one embodiment of any of the aspects or embodiments herein, the TNA LNPs described herein can be used to treat, ameliorate, and/or prevent a disease or disorder caused by mutation in a gene or gene product. Exemplary diseases or disorders that can be treated with the TNA LNPs (e.g., ceDNA vector lipid particles (e.g., lipid nanoparticles) as described herein)s include, but are not limited to, metabolic diseases or disorders (e.g., Fabry disease, Gaucher disease, phenylketonuria (PKU), glycogen storage disease); urea cycle diseases or disorders (e.g., ornithine transcarbamylase (OTC) deficiency); lysosomal storage diseases or disorders (e.g., metachromatic leukodystrophy (MLD), mucopolysaccharidosis Type II (MPSII; Hunter syndrome)); liver diseases or disorders (e.g., progressive familial intrahepatic cholestasis (PFIC); blood diseases or disorders (e.g., hemophilia A and B, thalassemia, and anemia); cancers and tumors, and genetic diseases or disorders (e.g., cystic fibrosis).

In one embodiment of any of the aspects or embodiments herein, the TNA LNPs (e.g., ceDNA vector lipid particles) may be employed to deliver a heterologous nucleotide sequence in situations in which it is desirable to regulate the level of transgene expression (e.g., transgenes encoding hormones or growth factors).

In one embodiment of any of the aspects or embodiments herein, the TNA LNPs (e.g., ceDNA vector lipid particles (e.g., lipid nanoparticles)) can be used to correct an abnormal level and/or function of a gene product (e.g., an absence of, or a defect in, a protein) that results in the disease or disorder. The TNA LNPs (e.g., ceDNA vector lipid particles (e.g., lipid nanoparticles)) can produce a functional protein and/or modify levels of the protein to alleviate or reduce symptoms resulting from, or confer benefit to, a particular disease or disorder caused by the absence or a defect in the protein. For example, treatment of OTC deficiency can be achieved by producing functional OTC enzyme; treatment of hemophilia A and B can be achieved by modifying levels of Factor VIII, Factor IX, and Factor X; treatment of PKU can be achieved by modifying levels of phenylalanine hydroxylase enzyme; treatment of Fabry or Gaucher disease can be achieved by producing functional alpha galactosidase or beta glucocerebrosidase, respectively; treatment of MFD or MPSII can be achieved by producing functional arylsulfatase A or iduronate-2-sulfatase, respectively; treatment of cystic fibrosis can be achieved by producing functional cystic fibrosis transmembrane conductance regulator; treatment of glycogen storage disease can be achieved by restoring functional G6Pase enzyme function; and treatment of PFIC can be achieved by producing functional ATP8B1, ABCB11, ABCB4, or TJP2 genes.

In one embodiment of any of the aspects or embodiments herein, the TNA LNP (e.g., ceDNA vector lipid particles (e.g., lipid nanoparticles)) can be used to provide an RNA-based therapeutic to a cell in vitro or in vivo. Examples of RNA-based therapeutics include, but are not limited to, mRNA, antisense RNA and oligonucleotides, ribozymes, aptamers, interfering RNAs (RNAi), Dicer-substrate dsRNA, small hairpin RNA (shRNA), asymmetrical interfering RNA (aiRNA), microRNA (miRNA). For example, the TNA LNP (e.g., ceDNA vector lipid particles (e.g., lipid nanoparticles)) can be used to provide an antisense nucleic acid to a cell in vitro or in vivo. For example, where the transgene is a RNAi molecule, expression of the antisense nucleic acid or RNAi in the target cell diminishes expression of a particular protein by the cell. Accordingly, transgenes which are RNAi molecules or antisense nucleic acids may be administered to decrease expression of a particular protein in a subject in need thereof. Antisense nucleic acids may also be administered to cells in vitro to regulate cell physiology, e.g., to optimize cell or tissue culture systems.

In one embodiment of any of the aspects or embodiments herein, the TNA LNP (e.g., ceDNA vector lipid particles (e.g., lipid nanoparticles)) can be used to provide a DNA-based therapeutic to a cell in vitro or in vivo. Examples of DNA-based therapeutics include, but are not limited to, minicircle DNA, minigene, viral DNA (e.g., Lentiviral or AAV genome) or non-viral synthetic DNA vectors, closed-ended linear duplex DNA (ceDNA/CELiD), plasmids, bacmids, Doggybone™ DNA vectors, minimalistic immunological-defined gene expression (MIDGE)-vector, nonviral ministring DNA vector (linear-covalently closed DNA vector), or dumbbell-shaped DNA minimal vector ("dumbbell DNA"). For example, In one embodiment of any of the aspects or embodiments herein, the ceDNA vectors (e.g., ceDNA vector lipid particles (e.g., lipid nanoparticles)) can be used to provide minicircle to a cell in vitro or in vivo. For example, where the transgene is a minicircle DNA, expression of the minicircle DNA in the target cell diminishes expression of a particular protein by the cell. Accordingly, transgenes which are minicircle DNAs may be administered to decrease expression of a particular protein in a subject in need thereof. Minicircle DNAs may also be administered to cells in vitro to regulate cell physiology, e.g., to optimize cell or tissue culture systems.

In one embodiment of any of the aspects or embodiments herein, exemplary transgenes encoded by a TNA vector comprising an expression cassette include, but are not limited to: X, lysosomal enzymes (e.g., hexosaminidase A, associated with Tay-Sachs disease, or iduronate sulfatase, associated, with Hunter Syndrome/MPS II), erythropoietin, angiostatin, endostatin, superoxide dismutase, globin, leptin, catalase, tyrosine hydroxylase, as well as cytokines (e.g., a interferon, β-interferon, interferon-7, interleukin-2, interleukin-4, interleukin 12, granulocyte-macrophage colony stimulating factor, lymphotoxin, and the like), peptide growth factors and hormones (e.g., somatotropin, insulin, insulin-like growth factors 1 and 2, platelet derived growth factor (PDGF), epidermal growth factor (EGF), fibroblast growth factor (FGF), nerve growth factor (NGF), neurotrophic factor-3 and 4, brain-derived neurotrophic factor (BDNF), glial derived growth factor (GDNF), transforming growth factor-a and -b, and the like), receptors (e.g., tumor necrosis factor receptor). In some exemplary embodiments, the transgene encodes a monoclonal antibody specific for one or more desired targets. In some exemplary embodiments, more than one transgene is encoded by the ceDNA vector. In some exemplary embodiments, the transgene encodes a fusion protein comprising two different polypeptides of interest. In some embodiments of any of the aspects and embodiments herein, the transgene encodes an antibody, including a full-length antibody or antibody fragment, as defined herein. In some embodiments of any of the aspects and embodiments herein, the antibody is an antigen-binding domain or an immunoglobulin variable domain sequence, as that is defined herein. Other illustrative transgene sequences encode suicide gene products (thymidine kinase, cytosine deaminase, diphtheria toxin, cytochrome P450, deoxycytidine kinase, and tumor necrosis factor), proteins conferring resistance to a drug used in cancer therapy, and tumor suppressor gene products.

Administration

In one embodiment of any of the aspects or embodiments herein, a TNA LNP (e.g., a ceDNA vector lipid particle as described herein) can be administered to an organism for transduction of cells in vivo. In one embodiment of any of the aspects or embodiments herein, TNA LNP (e.g., ceDNA vector lipid particles) can be administered to an organism for transduction of cells ex vivo.

Generally, administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route. Exemplary modes of administration of the TNA LNP (e.g., ceDNA vector lipid particles) includes oral, rectal, transmucosal, intranasal, inhalation (e.g., via an aerosol), buccal (e.g., sublingual), vaginal, intrathecal, intraocular, transdermal, intraendothelial, in utero (or in ovo), parenteral (e.g., intravenous, subcutaneous, intradermal, intracranial, intramuscular [including administration to skeletal, diaphragm and/or cardiac muscle], intrapleural, intracerebral, and intraarticular), topical (e.g., to both skin and mucosal surfaces, including airway surfaces, and trans-dermal administration), intralymphatic, and the like, as well as direct tissue or organ injection (e.g., to liver, eye, skeletal muscle, cardiac muscle, diaphragm muscle or brain).

Administration of the TNA LNP like ceDNA vector (e.g., a ceDNA LNP) can be to any site in a subject, including, without limitation, a site selected from the group consisting of the brain, a skeletal muscle, a smooth muscle, the heart, the diaphragm, the airway epithelium, the liver, the kidney, the spleen, the pancreas, the skin, and the eye. In one embodiment of any of the aspects or embodiments herein, administration of the ceDNA LNP can also be to a tumor (e.g., in or near a tumor or a lymph node). The most suitable route in any given case will depend on the nature and severity of the condition being treated, ameliorated, and/or prevented and on the nature of the particular ceDNA LNP that is being used. Additionally, ceDNA permits one to administer more than one transgene in a single vector, or multiple ceDNA vectors (e.g. a ceDNA cocktail).

In one embodiment of any of the aspects or embodiments herein, administration of the ceDNA LNP to skeletal muscle includes but is not limited to administration to skeletal muscle in the limbs (e.g., upper arm, lower arm, upper leg, and/or lower leg), back, neck, head (e.g., tongue), thorax, abdomen, pelvis/perineum, and/or digits. The ceDNA vectors (e.g., ceDNA vector lipid particles (e.g., lipid nanoparticles)) can be delivered to skeletal muscle by intravenous administration, intra-arterial administration, intraperitoneal administration, limb perfusion, (optionally, isolated limb perfusion of a leg and/or arm; see, e.g., Arruda et al., (2005) Blood 105: 3458-3464), and/or direct intramuscular injection. In particular embodiments, the ceDNA LNP is administered to a limb (arm and/or leg) of a subject (e.g., a subject with muscular dystrophy such as DMD) by limb perfusion, optionally isolated limb perfusion (e.g., by intravenous or intra-articular administration. In one embodiment of any of the aspects or embodiments herein, the ceDNA LNP can be administered without employing "hydrodynamic" techniques.

Administration of the TNA LNPs (e.g., ceDNA LNP) to cardiac muscle includes administration to the left atrium, right atrium, left ventricle, right ventricle and/or septum. The TNA LNP (e.g., ceDNA LNP) can be delivered to cardiac muscle by intravenous administration, intra-arterial administration such as intra-aortic administration, direct cardiac injection (e.g., into left atrium, right atrium, left ventricle, right ventricle), and/or coronary artery perfusion. Administration to diaphragm muscle can be by any suitable method including intravenous administration, intra-arterial administration, and/or intra-peritoneal administration. Administration to smooth muscle can be by any suitable method including intravenous administration, intra-arterial administration, and/or intra-peritoneal administration. In one embodiment of any of the aspects or embodiments herein, administration can be to endothelial cells present in, near, and/or on smooth muscle.

In one embodiment of any of the aspects or embodiments herein, TNA LNPs (e.g., ceDNA LNP) are administered to skeletal muscle, diaphragm muscle and/or cardiac muscle (e.g., to treat, ameliorate, and/or prevent muscular dystrophy or heart disease (e.g., PAD or congestive heart failure).

TNA LNPs (e.g., ceDNA LNP) can be administered to the CNS (e.g., to the brain or to the eye). The TNA LNP (e.g., ceDNA LNP) may be introduced into the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes, cortex, basal ganglia, hippocampus and portaamygdala), limbic system, neocortex, corpus striatum, cerebrum, and inferior colliculus. The TNA LNPs (e.g., ceDNA LNP) may also be administered to different regions of the eye such as the retina, cornea and/or optic nerve. The TNA LNPs (e.g., ceDNA LNP) may be delivered into the cerebrospinal fluid (e.g., by lumbar puncture). The TNA LNPs (e.g., ceDNA vector lipid particles) may further be administered intravascularly to the CNS in situations in which the blood-brain barrier has been perturbed (e.g., brain tumor or cerebral infarct).

In one embodiment of any of the aspects or embodiments herein, the TNA LNPs (e.g., ceDNA LNP) can be administered to the desired region(s) of the CNS by any route known in the art, including but not limited to, intrathecal, intra-ocular, intracerebral, intraventricular, intravenous (e.g., in the presence of a sugar such as mannitol), intranasal, intra-aural, intra-ocular (e.g., intra-vitreous, sub-retinal, anterior chamber) and peri-ocular (e.g., sub-Tenon's region) delivery as well as intramuscular delivery with retrograde delivery to motor neurons.

According to some embodiments of any of the aspects or embodiments herein, the TNA LNPs (e.g., ceDNA LNP) are administered in a liquid formulation by direct injection (e.g., stereotactic injection) to the desired region or compartment in the CNS. According to other embodiments, the TNA LNPs (e.g., ceDNA LNP) can be provided by topical application to the desired region or by intra-nasal administration of an aerosol formulation. Administration to the eye may be by topical application of liquid droplets. As a further alternative, the ceDNA vector can be administered as a solid, slow-release formulation (see, e.g., U.S. Pat. No. 7,201,898, incorporated by reference in its entirety herein). In one embodiment of any of the aspects or embodiments herein, the TNA LNPs (e.g., ceDNA LNP) can used for retrograde transport to treat, ameliorate, and/or prevent diseases and disorders involving motor neurons (e.g., amyotrophic lateral sclerosis (ALS); spinal muscular atrophy (SMA), etc.). For example, the TNA LNPs (e.g., ceDNA LNP) can be delivered to muscle tissue from which it can migrate into neurons.

In one embodiment of any of the aspects or embodiments herein, repeat administrations of the therapeutic product can be made until the appropriate level of expression has been achieved. Thus, in one embodiment of any of the aspects or embodiments herein, a therapeutic nucleic acid can be administered and re-dosed multiple times. For example, the therapeutic nucleic acid can be administered on day 0. Following the initial treatment at day 0, a second dosing (re-dose) can be performed in about 1 week, about 2 weeks, about 3 weeks, about 4 weeks, about 5 weeks, about 6 weeks, about 7 weeks, about 8 weeks, or about 3 months, about 4 months, about 5 months, about 6 months, about 7 months, about 8 months, about 9 months, about 10 months, about 11 months, or about 1 year, about 2 years, about 3 years, about 4 years, about 5 years, about 6 years, about 7 years, about 8 years, about 9 years, about 10 years, about 11 years, about 12 years, about 13 years, about 14 years, about 15 years, about 16 years, about 17 years, about 18 years, about 19 years, about 20 years, about 21 years, about 22 years, about 23 years, about 24 years, about 25 years, about 26 years, about 27 years, about 28 years, about 29 years, about 30 years, about 31 years, about 32 years, about 33 years, about 34 years, about 35 years, about 36 years, about 37 years, about 38 years, about 39 years, about 40 years, about 41 years, about 42 years, about 43 years, about 44 years, about 45 years, about 46 years, about 47 years, about 48 years, about 49 years or about 50 years after the initial treatment with the therapeutic nucleic acid.

In one embodiment of any of the aspects or embodiments herein, one or more additional compounds can also be included. Those compounds can be administered separately, or the additional compounds can be included in the lipid particles (e.g., lipid nanoparticles) of the invention. In other words, the lipid particles (e.g., lipid nanoparticles) can contain other compounds in addition to the TNA or at least a second TNA, different than the first. Without limitations, other additional compounds can be selected from the group consisting of small or large organic or inorganic molecules, monosaccharides, disaccharides, trisaccharides, oligosaccharides, polysaccharides, peptides, proteins, peptide analogs and derivatives thereof, peptidomimetics, nucleic acids, nucleic acid analogs and derivatives, an extract made from biological materials, or any combinations thereof.

In one embodiment of any of the aspects or embodiments herein, the one or more additional compound can be a therapeutic agent. The therapeutic agent can be selected from any class suitable for the therapeutic objective. Accordingly, the therapeutic agent can be selected from any class suitable for the therapeutic objective. The therapeutic agent can be selected according to the treatment objective and biological action desired. For example, In one embodiment of any of the aspects or embodiments herein, if the TNA within the LNP is useful for treating cancer, the additional compound can be an anti-cancer agent (e.g., a chemotherapeutic agent, a targeted cancer therapy (including, but not limited to, a small molecule, an antibody, or an antibody-drug conjugate). In one embodiment of any of the aspects or embodiments herein, if the LNP containing the TNA is useful for treating an infection, the additional compound can be an antimicrobial agent (e.g., an antibiotic or antiviral compound). In one embodiment of any of the aspects or embodiments herein, if the LNP containing the TNA is useful for treating an immune disease or disorder, the additional compound can be a compound that modulates an immune response (e.g., an immunosuppressant, immunostimulatory compound, or compound modulating one or more specific immune pathways). In one embodiment of any of the aspects or embodiments herein, different cocktails of different lipid particles containing different compounds, such as a TNA encoding a different protein or a different compound, such as a therapeutic may be used in the compositions and methods of the invention. In one embodiment of any of the aspects or embodiments herein, the additional compound is an immune modulating agent. For example, the additional compound is an immunosuppressant. In some embodiments of any of the aspects and embodiments herein, the additional compound is immunostimulatory.

EXAMPLES

The following examples are provided by way of illustration not limitation. It will be appreciated by one of ordinary skill in the art that ionizable lipids can be designed and synthesized using general synthesis methods described below.

General Synthesis

Ionizable lipids of Formula I were designed and synthesized using similar synthesis methods depicted in Scheme 1 below.

Example 1

Synthesis of 1-(heptadecan-9-yl) 9-(4-(2-(2-(1-(2-((2-(4-(2-(2-(4-(oleoyloxy)phenyl)acetoxy)ethyl)piperidin-1-yl)ethyl)disulfaneyl)ethyl)piperidin-4-yl)ethoxy)-2-oxoethyl)phenyl) nonanedioate (Lipid 1)

Synthesis of cleavable, ionizable head group ((disulfanediylbis(ethane-2,1-diyl))bis(piperidine-1,4-diyl))bis(ethane-2,1-diyl) bis(2-(4-hydroxyphenyl)acetate) (7)

Step-1

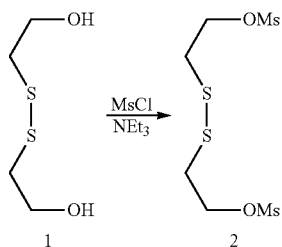 [SMILES: "MsCl" ; OCCSSCCO ; CS(=O)(=O)OCCSSCCOS(C)(=O)=O ; "NEt3"]

Synthesis of disulfanediylbis(ethane-2,1-diyl) dimethanesulfonate (2). Commercially available 2,2'-disulfanediylbis

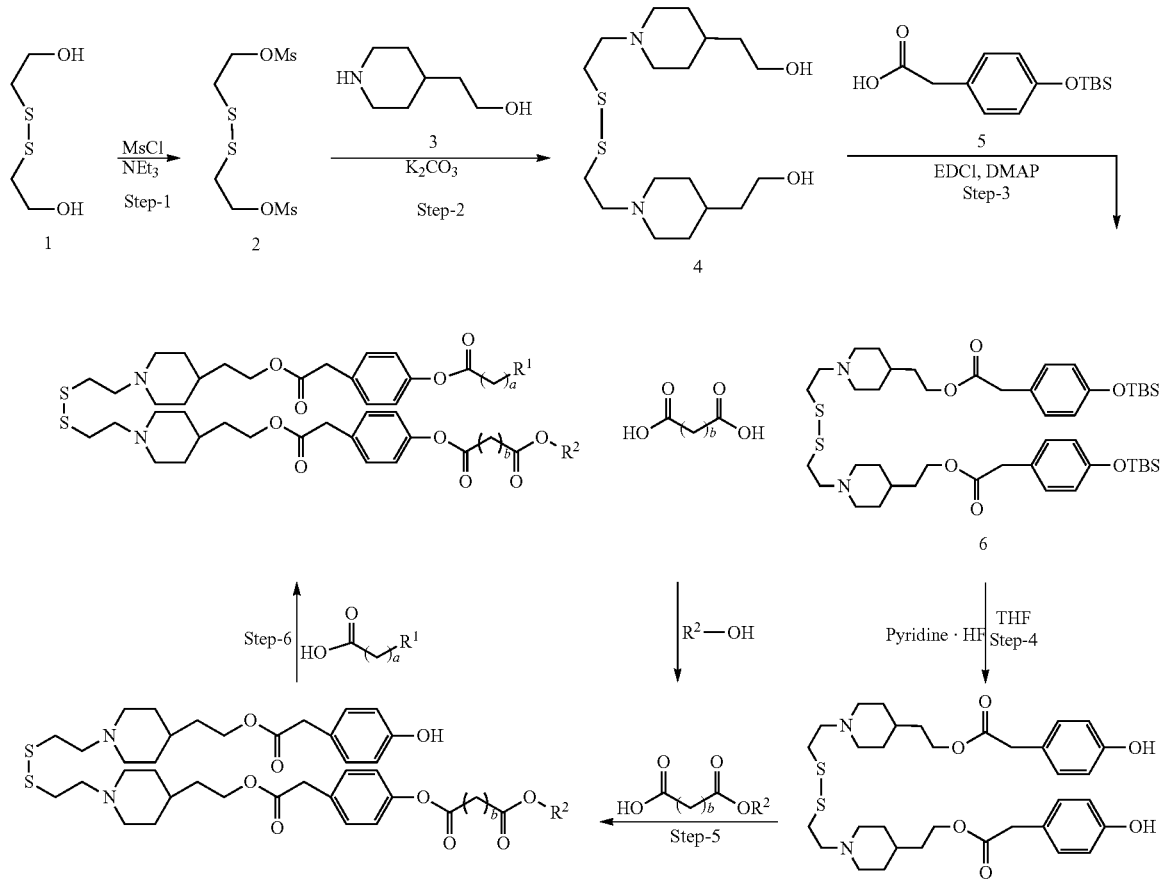

(ethan-1-ol) (1) (15 g, 97.2 mmol) was dissolved in acetonitrile (143 ml) followed by the addition of triethylamine (NEt₃) (33.3 g, 328 mmol). To the reaction mixture was added methanesulfonyl chloride (MsCl) (34.5 g, 300 mmol) dropwise at 0° C. The resulting reaction mixture was stirred at room temperature for 3 h. To the reaction mixture was added ethanol (EtOH) (39 ml) to quench the reaction and the insoluble materials were removed through filtration. The filtrate was partitioned between dichloromethane (DCM) (150 ml) and 10% sodium bicarbonate/water (150 ml). The organic layer was washed with 100 ml water four times, dried over magnesium sulfate (MgSO₄), and evaporated to give 2 as a brown oil (25 g, 81%), which solidified upon standing. ¹H-NMR (300 MHz, d-chloroform): δ 4.43-4.48 (t, 4H), 3.00-3.10 (m, 10H).

Step-2

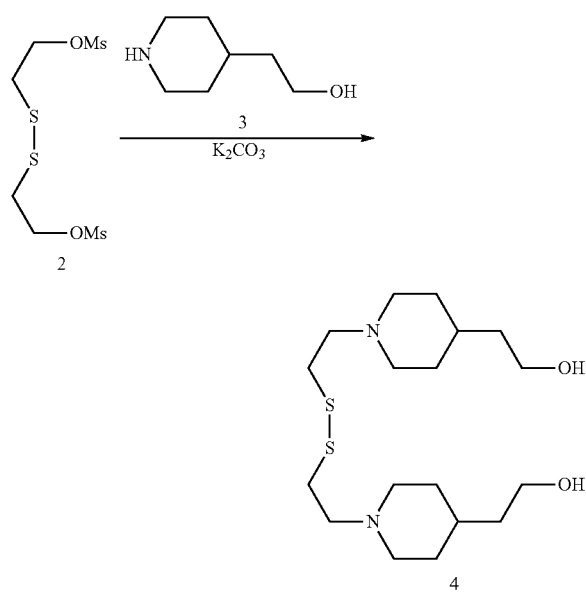

Synthesis of 2,2'-((disulfanediylbis(ethane-2,1-diyl))bis (piperidine-1,4-diyl))bis(ethan-1-ol) (4). To a solution of 2 (12 g, 38.7 mmol) in acetonitrile (310 ml) was added potassium carbonate (K₂CO₃) (13.4 g, 96.6 mmol) followed by 2-(piperidin-4-yl)ethan-1-ol (3) (20 g, 155 mmol). The resulting mixture was stirred at room temperature overnight before the insoluble material was removed through filtration. The filtrate was evaporated to dryness to afford the crude product, which was dissolved in DCM (100 ml), washed with water twice (50 ml), dried over MgSO₄, and evaporated give 4 as a yellow oil (11.8 g, 79%). ¹H-NMR (300 MHz, d-chloroform): δ 3.63-3.68 (t, 4H), 2.78-2.90 (m, 8H), 2.62-2.65 (t, 4H), 1.94-2.02 (t, 4H), 1.70 (s, 2H), 1.65-1.70 (d, 4H), 1.27-1.48 (t, 4H), 1.40-1.50 (m, 2H), 1.23-1.27 (m, 4H).

Step-3

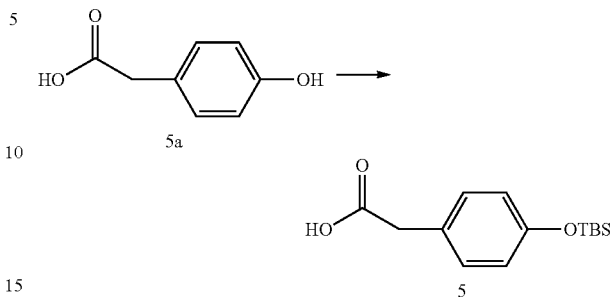

Synthesis of 2-(4-((tert-butyldimethylsilyl)oxy)phenyl) acetic acid (5). To a stirred solution of 4-hydroxyphenylacetic acid (5a) (10 g, 65 mmol) in dimethylformamide (DMF) (40 ml) at 0° C. was added NEt₃ (10 g, 100 mmol) followed by tert-butyldimethylsilylchloride (TBSCl) (15 g, 100 mmol). The resulting reaction mixture was stirred at room temperature overnight, then treated with water (200 ml) and DCM (150 ml). The organic phase was separated. The aqueous phase was extracted with DCM (100 ml). The combined organic phase was washed with a saturated solution of sodium bicarbonate, brine and dried over sodium sulfate (Na₂SO₄). Solvent was removed under reduced pressure and the residue was purified by silica gel column chromatography using 0-10% methanol (MeOH) in DCM as eluent. The fractions containing the desired compound were pooled and evaporated to afford 5 (4.8 g, 27%) and the di-tert-butyldimethylsilyl ether (di-TBS) by-product (10.5 g, 42%). ¹H-NMR of 5 (300 MHz, d-chloroform): δ 7.12 (d, 2H), 6.78 (d, 2H), 3.56 (s, 2H), 0.97 (s, 9H), 0.18 (s, 6H).

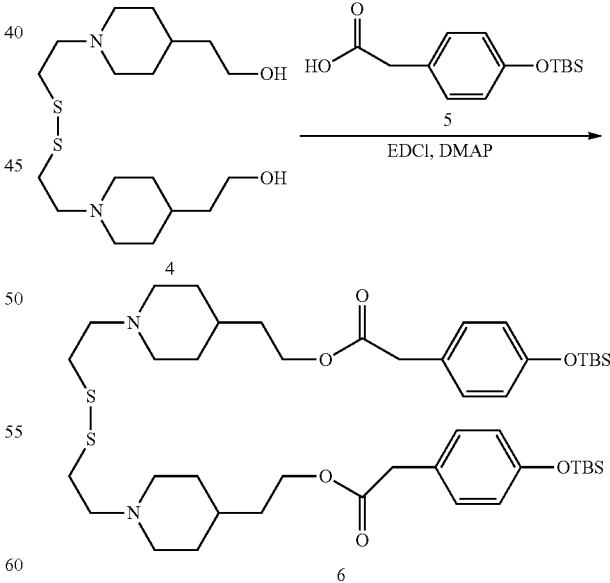

Synthesis of ((disulfanediylbis(ethane-2,1-diyl))bis(piperidine-1,4-diyl))bis(ethane-2,1-diyl) bis(2-(4-((tert-butyldimethylsilyl)oxy)phenyl)acetate) (6). To a stirred solution of the disulfide 4 yielded from Step-2 (1.92 g, 5 mmol) and phenylacetic acid 5 (3.4 g, 12.8 mmol) in DCM (100 ml) was added 4-dimethylaminopyridine (DMAP) (1.5 g, 12.5 mmol) followed by 1-ethyl-3-(3-dimethylaminopropyl)carbodiimide (EDCI) (2.4 g, 12.5 mmol). The resulting mixture was stirred at room temperature overnight, then washed with a saturated solution of sodium bicarbonate (200 ml), brine (150 ml) and dried over $Na_2SO_4$. Solvent was removed under reduced pressure and the residue was purified by silica gel column chromatography using 0-10% MeOH in DCM as eluent. The fractions containing the desired compound were evaporated to afford 6 (4.1 g, 92%). $^1$H-NMR of 6 (300 MHz, d-chloroform): δ 7.12 (d, 4H), 6.75 (d, 4H), 4.1 (t, 4H), 3.5 (s, 4H), 2.82 (m, 8H), 2.62 (m, 4H), 1.93 (t, 4H), 1.61-1.45 (m, 8H), 1.26 (m, 6H), 0.97 (s, 18H), 0.17 (s, 4H).

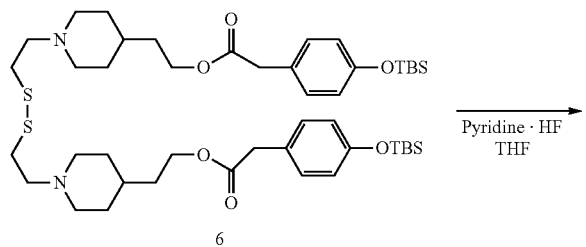

6

Synthesis of ((disulfanediylbis(ethane-2,1-diyl))bis(piperidine-1,4-diyl))bis(ethane-2,1-diyl) bis(2-(4-hydroxyphenyl)acetate) (7). To a stirred solution of disulfide 6 (3.1 g, 3.6 mmol) in tetrahydrofuran (THF) (40 ml) was added hydrogen fluoride pyridine (1 ml, 3.8 mmol) at 0° C. The resulting mixture was stirred at 0° C. for 2 h, then room temperature for another 2 h. The reaction mixture was treated with a saturated solution of sodium bicarbonate (200 ml) and extracted with ethyl acetate (2×150 ml). The combined organic phase was washed with brine (100 ml), dried over $Na_2SO_4$ and concentrated. The residue was purified by silica gel column chromatography using 0-10% MeOH in DCM as eluent providing the desired product 7 (1.92 g, 82%). $^1$H-NMR (300 MHz, d-chloroform): δ 7.13 (d, 4H), 6.70 (d, 4H), 4.1 (t, 4H), 3.5 (s, 4H), 2.89 (m, 8H), 2.70 (m, 4H), 1.95 (t, 4H), 1.48 (m, 8H), 1.17 (m, 6H).

Synthesis of 9-(heptadecan-9-yloxy)-9-oxononanoic acid (10)

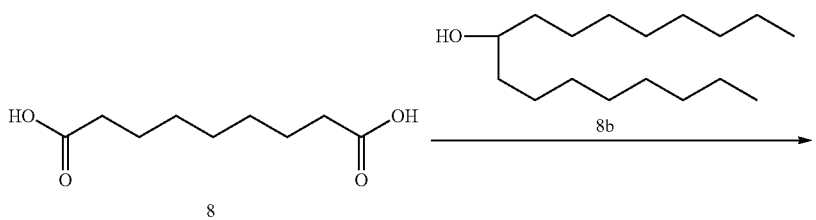

8

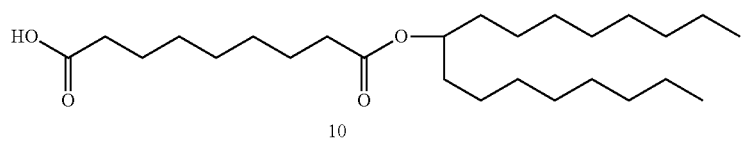

10

Synthesis of 9-(heptadecan-9-yloxy)-9-oxononanoic acid (10). To a stirred solution of nonanedioic acid (8) (7.34 g, 39 mmol) and heptadecan-9-ol (8b) (5 g, 19 mmol) in dichloromethane (1000 ml) was added DMAP (2.37 g, 19 mmol) followed by EDCI (3 g, 19 mmol). The resulting mixture was stirred at room temperature overnight, then washed with 250 ml 1 N HCl and 250 ml water. The organic layer was dried over MgSO$_4$, evaporated to dryness and purified by silica gel column chromatography using 0-10% MeOH in DCM as eluent. The fractions containing the desired compound were pooled and evaporated to afford 10 (6.2 g, 75%) as a white solid. $^1$H-NMR (300 MHz, d-chloroform): δ 4.80-4.90 (m, 1H), 2.25-2.34 (m, 4H), 1.55-1.70 (m, 4H), 1.40-1.50 (m, 4H), 1.20-1.40 (m, 30H), 0.84-0.90 (t, 3H).

Synthesis of 1-(heptadecan-9-yl) 9-(4-(2-(2-(1-(2-((2-(4-(2-(2-(4-hydroxyphenyl)acetoxy)ethyl)piperidin-1-yl)ethyl)disulfaneyl)ethyl)piperidin-4-yl)ethoxy)-2-oxoethyl)phenyl) nonanedioate Synthesis of 1-(heptadecan-9-yl) 9-(4-(2-(2-(1-(2-((2-(4-(2-(2-(4-hydroxyphenyl)acetoxy)ethyl)piperidin-1-yl)ethyl)disulfaneyl)ethyl)piperidin-4-yl)ethoxy)-2-oxoethyl)phenyl) nonanedioate (11). To a stirred solution of the disulfide 7 produced in Step-4 (580 mg, 0.9 mmol) and acid 10 (422 mg, 0.99 mmol) in DMF (20 ml) was added DMAP (165 mg, 1.35 mmol) followed by EDCI (258 mg, 1.35 mmol). The resulting mixture was stirred at room temperature overnight, then a saturated sodium bicarbonate solution (50 ml) was added. The reaction mixture was extracted with dichloromethane (2×50 ml). The combined organic phase was washed with brine (30 ml), dried over Na$_2$SO$_4$ and concentrated. The residue was purified by silica gel column chromatography using 0-10% MeOH in DCM as eluent to give the desired product 11 (427 mg, 45%). $^1$H-NMR (300 MHz, d-chloroform): δ 7.27 (d, 2H), 7.11 (d, 2H), 7.03 (d, 2H), 6.69 (d, 2H), 4.85 (m, 1H), 4.1 (m, 4H), 3.56 (s, 2H), 3.48 (s, 2H), 2.92 (d, 2H), 2.85-2.69 (m, 12H), 2.71 (t, 2H), 2.28 (t, 2H), 1.95 (t, 2H), 1.52-1.01 (m, 53H), 0.85 (m, 6H).

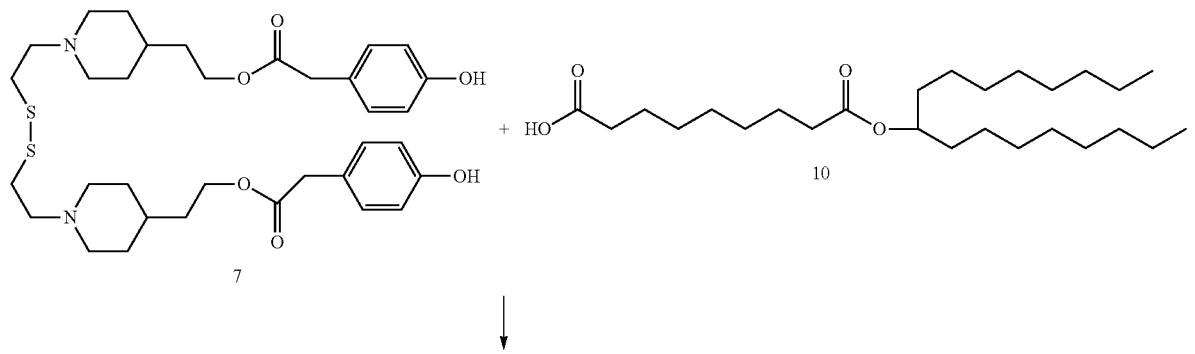

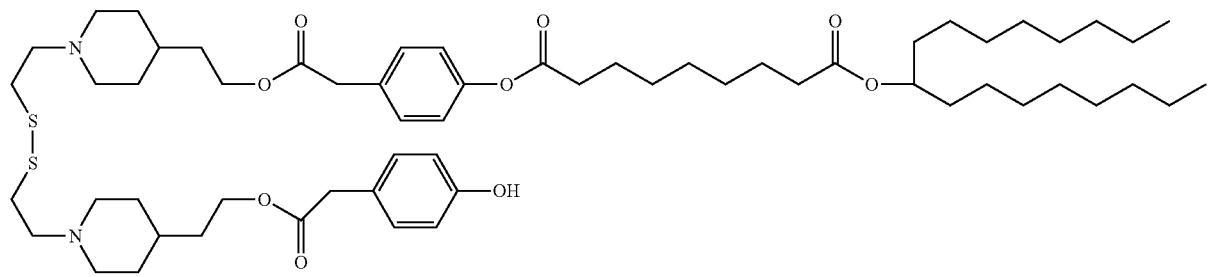

Synthesis of Lipid 1

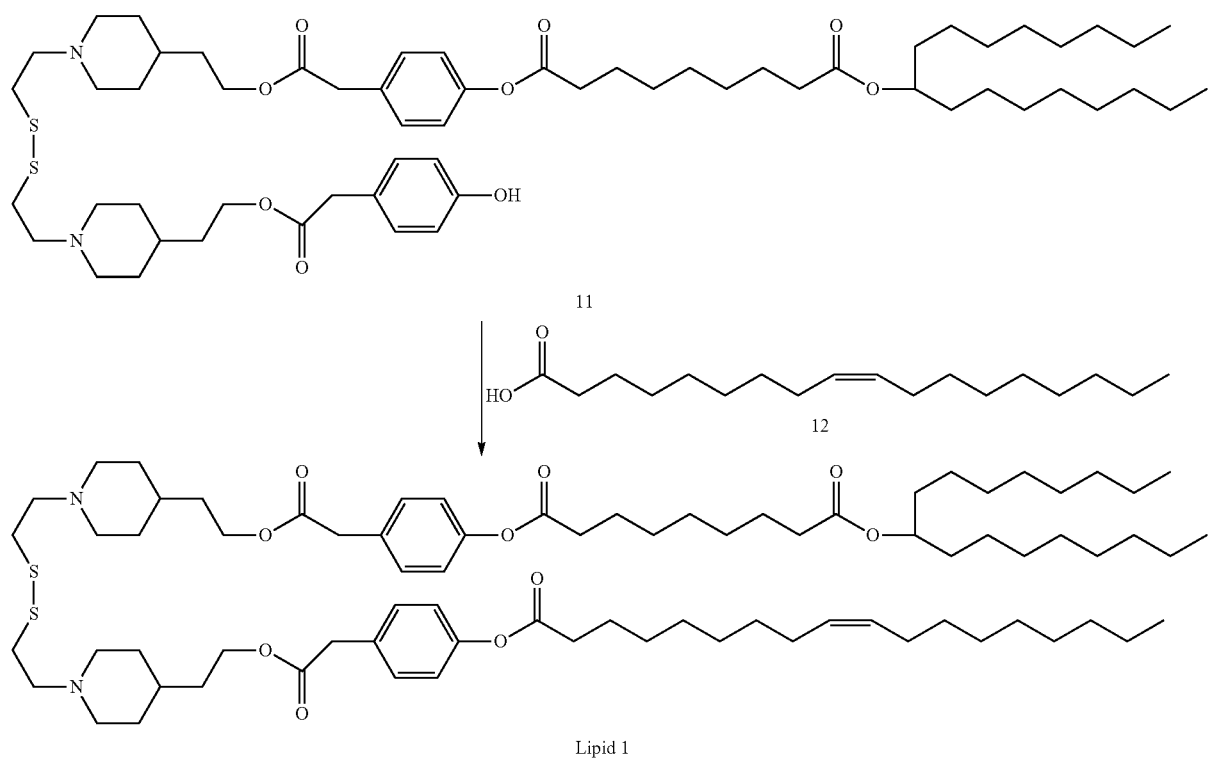

Lipid 1

Synthesis of 1-(heptadecan-9-yl) 9-(4-(2-(2-(1-(2-((2-(4-(2-(2-(4-(oleoyloxy)phenyl)acetoxy)ethyl)piperidin-1-yl)ethyl)disulfaneyl)ethyl)piperidin-4-yl)ethoxy)-2-oxoethyl)phenyl) nonanedioate (Lipid 1). To a stirred solution of disulfide 11 (151 mg, 0.14 mmol) and oleic acid 12 (61 mg, 0.22 mmol) in dichloromethane (10 ml) was added DMAP (28 mg, 0.22 mmol) followed by EDCI (42 mg, 0.22 mmol). The resulting mixture was stirred at room temperature overnight, then washed with saturated sodium bicarbonate solution (20 ml), brine (20 ml) and dried over $Na_2SO_4$. Solvent was removed under reduced pressure and the residue was purified by silica gel column chromatography using 0-10% MeOH in DCM as eluent. The fractions containing the desired compound was evaporated to afford Lipid 1 (126 mg, 68%). $^1$H-NMR of Lipid 1 (300 MHz, d-chloroform): δ 7.25 (d, 4H), 7.01 (d, 4H), 5.34 (m, 2H), 4.86 (m, 1H), 4.11 (t, 4H), 3.58 (s, 4H), 2.91-2.70 (m, 8H), 2.62 (m, 4H), 2.53 (t, 4H), 2.28 (t, 2H), 2.05-1.87 (m, 8H), 1.78-1.46 (m, 22H), 1.48-1.23 (m, 54H), 0.86 (t, 9H). MS [M+H]$^+$ 1318.

Example 2: Synthesis of 1-(heptadecan-9-yl) 9-(4-(2-(2-(1-(2-((2-(4-(2-(2-(4-((9-(nonyloxy)-9-oxononanoyl)oxy)phenyl)acetoxy)ethyl)piperidin-1-yl)ethyl)disulfaneyl)ethyl)piperidin-4-yl)ethoxy)-2-oxoethyl)phenyl) nonanedioate (Lipid 3)

Synthesis of 9-(nonyloxy)-9-oxononanoic acid (9)

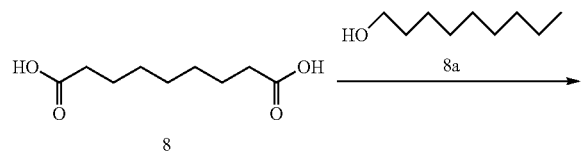

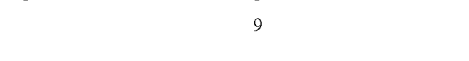

Synthesis of 9-(nonyloxy)-9-oxononanoic acid (9). To a stirred solution of nonanedioic acid (8) (13.2 g, 0.1 mol) and nonan-1-ol (8a) (7.2 g, 0.05 mol) in DCM (1000 ml) was added DMAP (6.1 g, 0.05 mol) followed by EDCI (7.7 g, 0.05 mol). The resulting mixture was stirred at room temperature overnight, then washed with 1 N hydrochloric acid (HCl) solution (500 ml) and water (500 ml). The organic layer was dried over $MgSO_4$, evaporated to dryness and purified by silica gel column chromatography using 0-10% MeOH in DCM as eluent. The fractions containing the desired compound were pooled and evaporated to afford 9 (12.6 g, 81%) as a white solid. $^1$H-NMR (300 MHz, d-chloroform): δ 4.03-4.07 (t, 2H), 2.28-2.34 (m, 4H), 1.58-1.63 (m, 6H), 1.26-1.32 (m, 18H), 0.85-0.87 (t, 3H).

Synthesis of Lipid 3

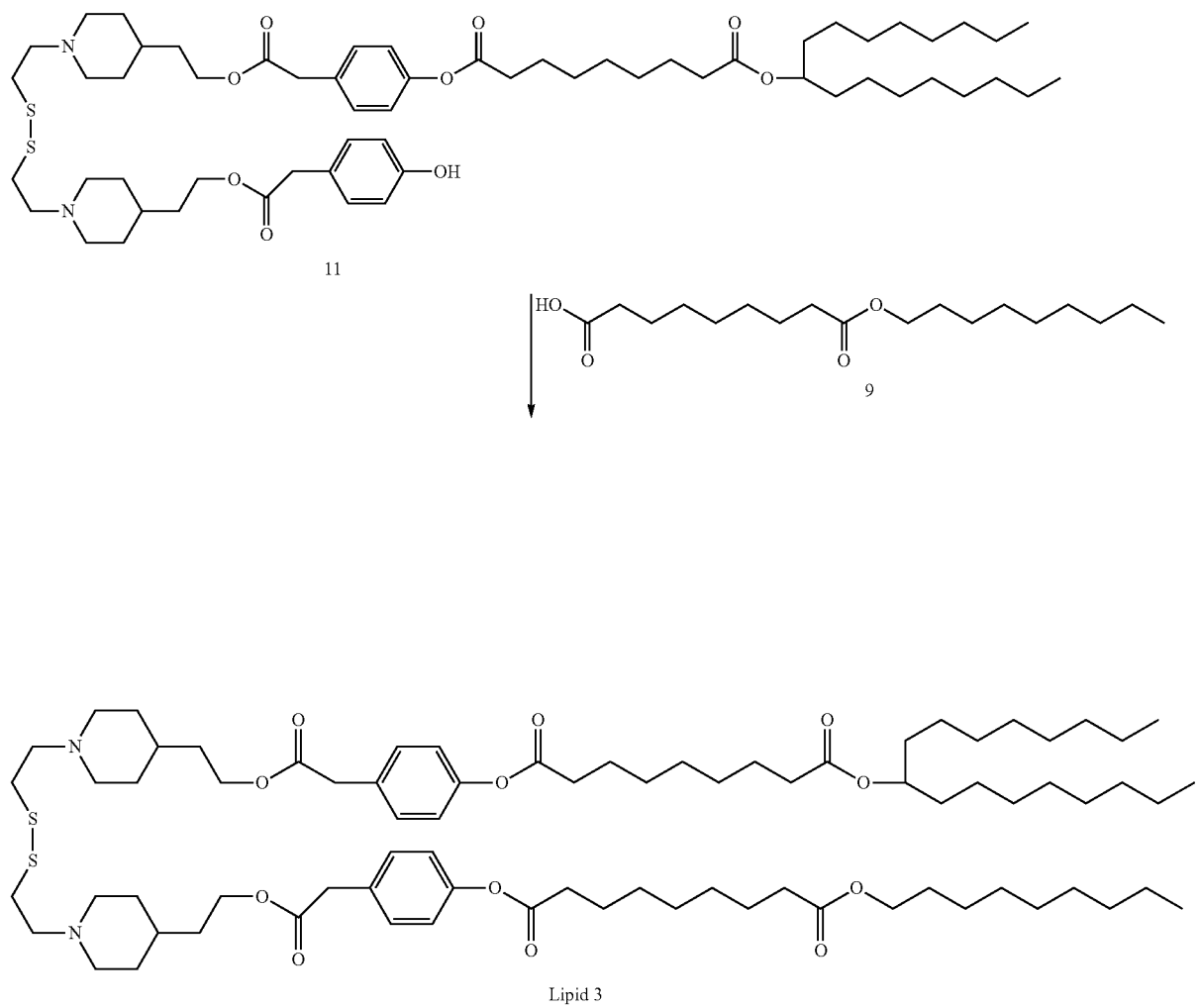

Synthesis of 1-(heptadecan-9-yl) 9-(4-(2-(2-(1-(2-((2-(4-(2-(2-(4-((9-(nonyloxy)-9-oxononanoyl)oxy)phenyl)acetoxy)ethyl)piperidin-1-yl)ethyl)disulfaneyl)ethyl)piperidin-4-yl)ethoxy)-2-oxoethyl)phenyl) nonanedioate (Lipid 3). To a stirred solution of disulfide 11 (step-by-step synthesis described in Example 1) (150 mg, 0.14 mmol) and acid 9 (62 mg, 0.22 mmol) in dichloromethane (10 ml) was added DMAP (28 mg, 0.22 mmol) followed by EDCI (42 mg, 0.22 mmol). The resulting mixture was stirred at room temperature overnight, then washed with saturated sodium bicarbonate solution (20 ml), brine (20 ml) and dried over Na$_2$SO$_4$. Solvent was removed under reduced pressure and the residue was purified by silica gel column chromatography using 0-10% MeOH in DCM as eluent. The fraction containing the desired compound was evaporated to afford Lipid 3 (114 mg, 60%). $^1$H-NMR of Lipid 3 (300 MHz, d-chloroform): δ 7.28 (d, 4H), 7.02 (d, 4H), 4.86 (m, 1H), 4.11 (t, 4H), 4.04 (t, 2H), 3.58 (s, 4H), 2.93-2.77 (m, 8H), 2.63 (m, 4H), 2.53 (t, 4H), 2.28 (m, 4H), 1.95 (t, 4H), 1.85-1.47 (m, 24H), 1.45-1.16 (m, 54H), 0.86 (t, 9H). MS [M+H]$^+$ 1350.

Example 3: Synthesis of 1-(heptadecan-9-yl) 9-(4-(2-(2-(1-(2-((2-(4-(2-(2-(4-((5-(nonyloxy)-5-oxopentanoyl)oxy)phenyl)acetoxy)ethyl) piperidin-1-yl) ethyl)disulfaneyl)ethyl) piperidin-4-yl)ethoxy)-2-oxoethyl)phenyl) nonanedioate (Lipid 2)

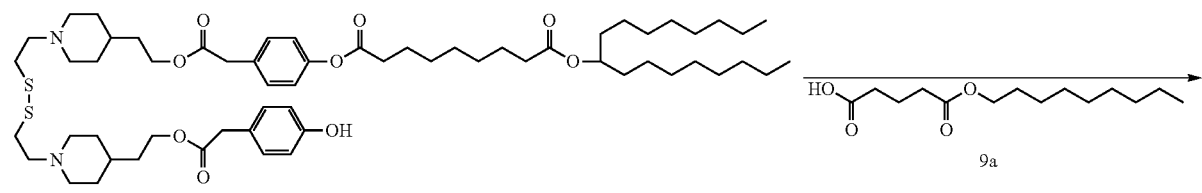

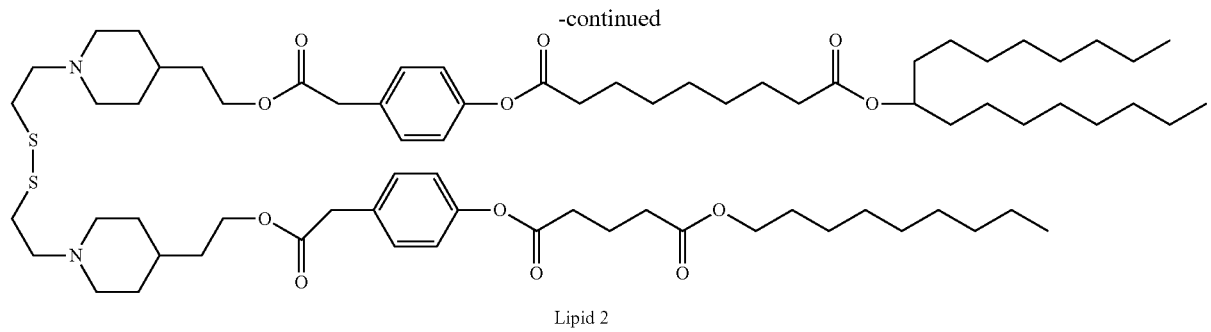

Lipid 2

To a stirred solution of disulfide 11 (step-by-step synthesis described in Example 1) (150 mg, 0.14 mmol) and acid 9a (see synthesis described in Example 1 for acid 9, where nonanedioic acid (8) was replaced with commercially available glutaric acid as starting material to react with nonan-1-ol (8a) to produce 9a) (57 mg, 0.22 mmol) in DCM (10 ml) was added DMAP (28 mg, 0.22 mmol) followed by EDCI (42 mg, 0.22 mmol). The resulting mixture was stirred at room temperature overnight, then washed with saturated sodium bicarbonate solution (20 ml), brine (20 ml) and dried over $Na_2SO_4$. Solvent was removed under reduced pressure and the residue was purified by silica gel column chromatography using 0-10% MeOH in DCM as eluent. The fraction containing the desired compound was evaporated to afford Lipid 2 (151 mg, 81%). $^1$H-NMR of Lipid 2 (300 MHz, d-chloroform): δ 7.26 (d, 4H), 7.01 (d, 4H), 4.86 (m, 1H), 4.10-4.02 (t, 6H), 3.57 (s, 4H), 3.01 (d, 4H), 2.83-2.72 (m, 4H), 2.34-2.21 (m, 14H), 2.15-1.91 (m, 6H), 1.74-1.41 (m, 12H), 1.39-1.16 (m, 52H), 0.86 (t, 9H). MS [M+H]$^+$ 1293.

Example 4: Synthesis of 1-(heptadecan-9-yl) 9-(4-(2-(2-(1-(2-((2-(4-(2-(2-(4-((5-(nonyloxy)-5-oxopentanoyl)oxy)phenyl)acetoxy)ethyl) piperidin-1-yl)ethyl)disulfaneyl)ethyl)piperidin-4-yl)ethoxy)-2-oxoethyl)phenyl) nonanedioate (Lipid 4)

To a stirred solution of disulfide 7 (step-by-step synthesis described in Example 1) (150 mg, 0.23 mmol) and compound 9 (synthesis described in Example 2) (146 mg, 0.46 mmol) in a mixture of dichloromethane (5 ml) and DMF (3 ml) was added DMAP (70 mg, 0.57 mmol) followed by EDCI (109 mg, 0.57 mmol) at 0° C. The resulting mixture was stirred at 0° C. for 15 minutes, then at RT overnight. DCM (20 ml) was added and the reaction mixture was washed with saturated sodium bicarbonate solution (20 ml), brine (20 ml), dried over $Na_2SO_4$. Solvent was removed under reduced pressure and the residue was purified by silica gel column chromatography using 0-10% MeOH in DCM as eluent. The fraction containing the desired compound was evaporated to afford Lipid 4 (180 mg, 63%). $^1$H-NMR of Lipid 4 (300 MHz, d-chloroform): δ 7.28 (d, 4H), 7.02 (d, 4H), 4.11 (t, 4H), 4.04 (t, 4H), 3.58 (s, 4H), 2.93-2.67 (m, 8H), 2.63-2.55 (m, 4H), 2.53 (t, 4H), 2.29 (t, 4H), 1.94 (t, 4H), 1.85-1.47 (m, 20H), 1.45-1.16 (m, 42H), 0.87 (t, 6H). MS [M+H]$^+$ 1237.

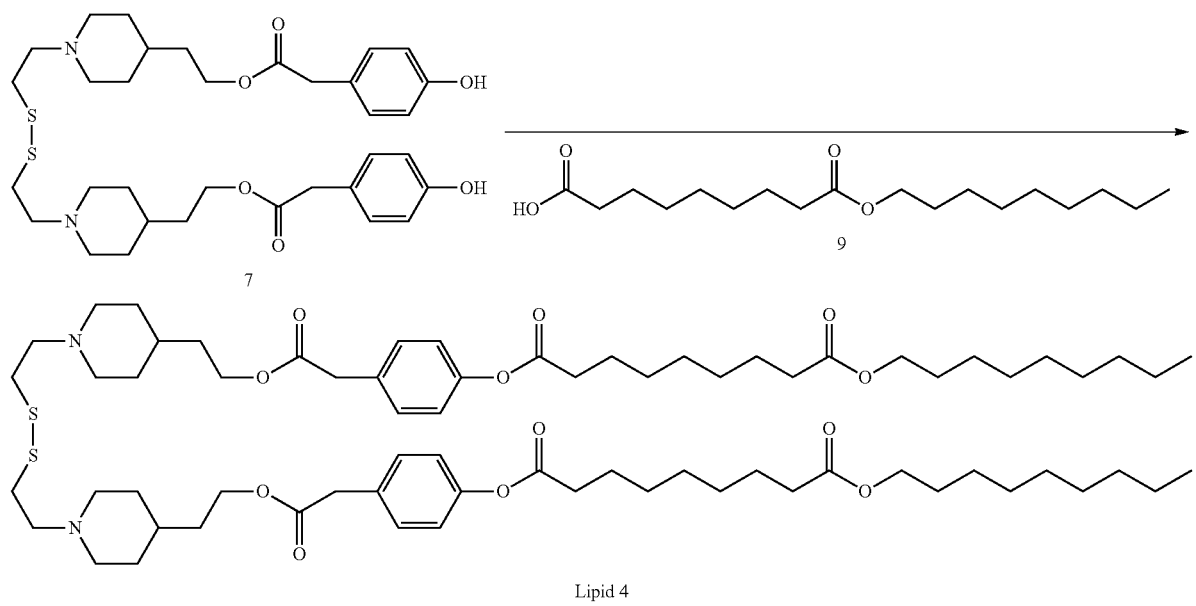

Lipid 4

Example 5: Synthesis of O'1,O1-((((((disulfanediyl-bis(ethane-2,1-diyl))bis(piperidine-1,4-diyl))bis(ethane-2,1-diyl))bis(oxy))bis(2-oxoethane-2,1-diyl))bis(4,1-phenylene)) 9,9'-di(heptadecan-9-yl) di(nonanedioate) (Lipid 5)

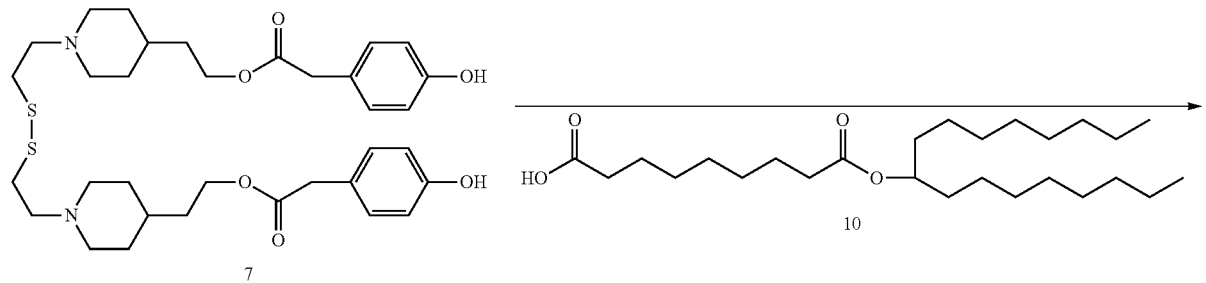

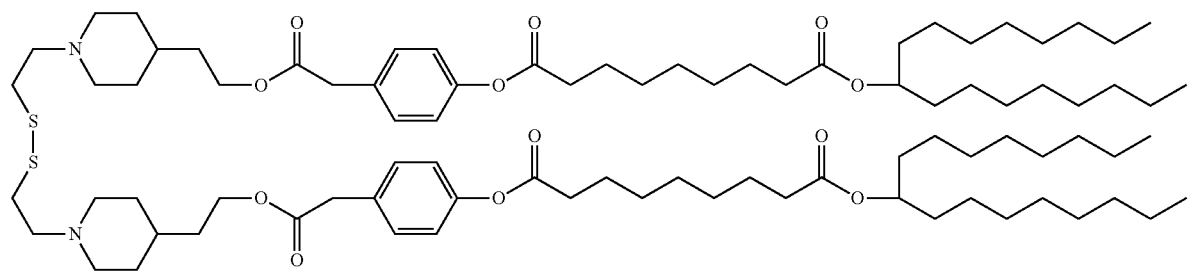

Lipid 5

To a stirred solution of disulfide 7 (step-by-step synthesis as described in Example 1) (580 mg, 0.9 mmol) and acid 10 (synthesis described in Example 1) (422 mg, 0.99 mmol) in DMF (20 ml) was added DMAP (164 mg, 1.35 mmol) followed by EDCI (257 mg, 1.35 mmol) at 0° C. The resulting mixture was stirred at 0° C. for 15 minutes, then at RT overnight. DCM (60 ml) was added and the reaction mixture was washed with saturated sodium bicarbonate solution (20 ml), brine (20 ml), dried over $Na_2SO_4$. Solvent was removed under reduced pressure and the residue was purified by silica gel column chromatography using 0-10% MeOH in DCM as eluent. The fraction containing the desired compound was evaporated to afford Lipid 5 (280 mg, 38%). $^1$H-NMR of Lipid 5 (300 MHz, d-chloroform): δ 7.26 (d, 4H), 7.02 (d, 4H), 4.85 (m, 2H), 4.11 (t, 4H), 3.58 (s, 4H), 2.86-2.77 (m, 8H), 2.63 (m, 4H), 2.53 (t, 4H), 2.27 (t, 4H), 1.92 (t, 4H), 1.75-1.47 (m, 26H), 1.45-1.16 (m, 64H), 0.86 (t, 12H). MS $[M+H]^+$ 1462.

Example 6: Synthesis of 1-(4-(2-(2-(1-(2-((2-(4-(2-(2-(4-(oleoyloxy)phenyl)acetoxy)ethyl)piperidin-1-yl)ethyl)disulfaneyl)ethyl)piperidin-4-yl)ethoxy)-2-oxoethyl)phenyl) 9-(undecan-3-yl) nonanedioate (Lipid 6)

Synthesis of 9-oxo-9-(undecan-3-yloxy)nonanoic acid (9b)

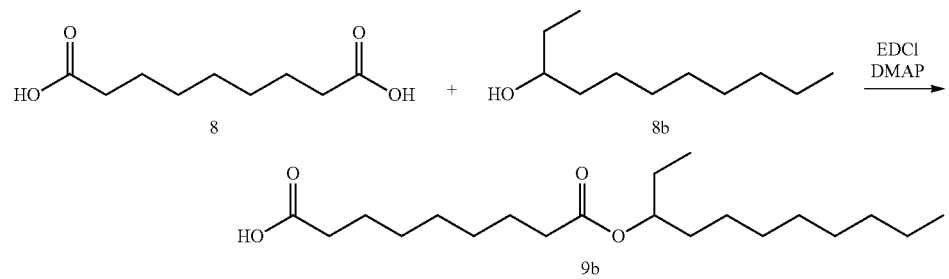

Synthesis of 9-oxo-9-(undecan-3-yloxy)nonanoic acid (9b). To a stirred solution of nonanedioic acid (8) (10.9 g, 0.058 mol) and undecan-3-ol (8b) (5 g, 0.029 mol) in DCM (500 ml) was added DMAP (3.5 g, 0.03 mol) followed by EDCI (4.5 g, 0.03 mol). The resulting mixture was stirred at RT overnight, then washed with 1 N HCl solution (500 ml) and water (500 ml). The organic layer was dried over MgSO$_4$, evaporated to dryness and purified by silica gel column chromatography using 0-10% MeOH in DCM as eluent. The fractions containing the desired compound were pooled and evaporated to afford 9b (6.5 g, 66%) as a white solid. $^1$H-NMR (300 MHz, d-chloroform): δ 4.79-4.83 (t, 1H), 2.28-2.34 (m, 4H), 1.25-1.33 (m, 8H), 1.26-1.32 (m, 18H), 0.85-0.87 (t, 6H).

Synthesis of 4-(2-(2-(1-(2-((2-(4-(2-(2-(4-hydroxyphenyl)acetoxy)ethyl)piperidin-1-yl)ethyl)disulfaneyl)ethyl)piperidin-4-yl)ethoxy)-2-oxoethyl)phenyl oleate (13)

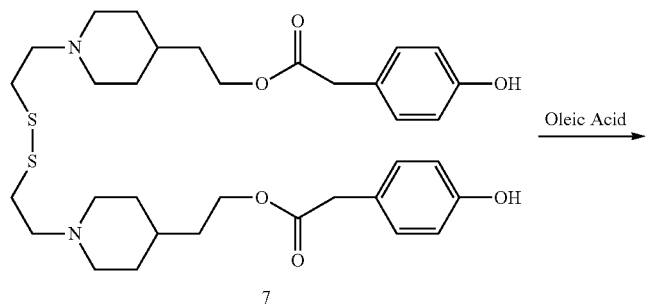

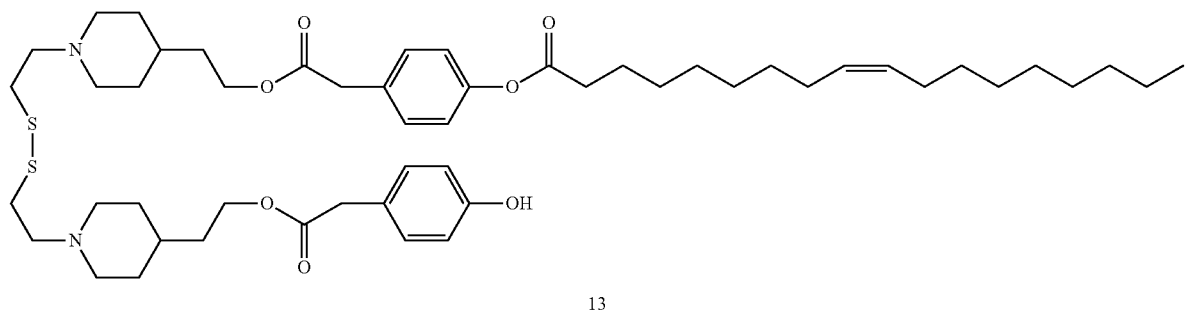

Synthesis of 4-(2-(2-(1-(2-((2-(4-(2-(2-(4-hydroxyphenyl)acetoxy)ethyl)piperidin-1-yl)ethyl)disulfaneyl)ethyl)piperidin-4-yl)ethoxy)-2-oxoethyl)phenyl oleate (13). To a stirred solution of disulfide 7 (step-by-step synthesis described in Example 1) (2.0 g, 3 mmol) and oleic acid (or acid 12 as described in Example 1) (0.79 g, 2.8 mmol) in DCM (200 ml) was added DMAP (340 mg, 2.8 mmol) followed by EDCI (440 mg, 2.8 mmol). The resulting mixture was stirred at room temperature overnight, then a saturated sodium bicarbonate solution (20 ml) was added. The reaction mixture was extracted with dichloromethane (2×50 ml). The combined organic phase was washed with brine (30 ml), dried over Na$_2$SO$_4$ and concentrated. The residue was purified by silica gel column chromatography using 0-5% methanol in dichloromethane as eluent to afford 13 (1.6 g, 57%) as white solid. The product was used directly in the next step without further characterization.

Synthesis of Lipid 6

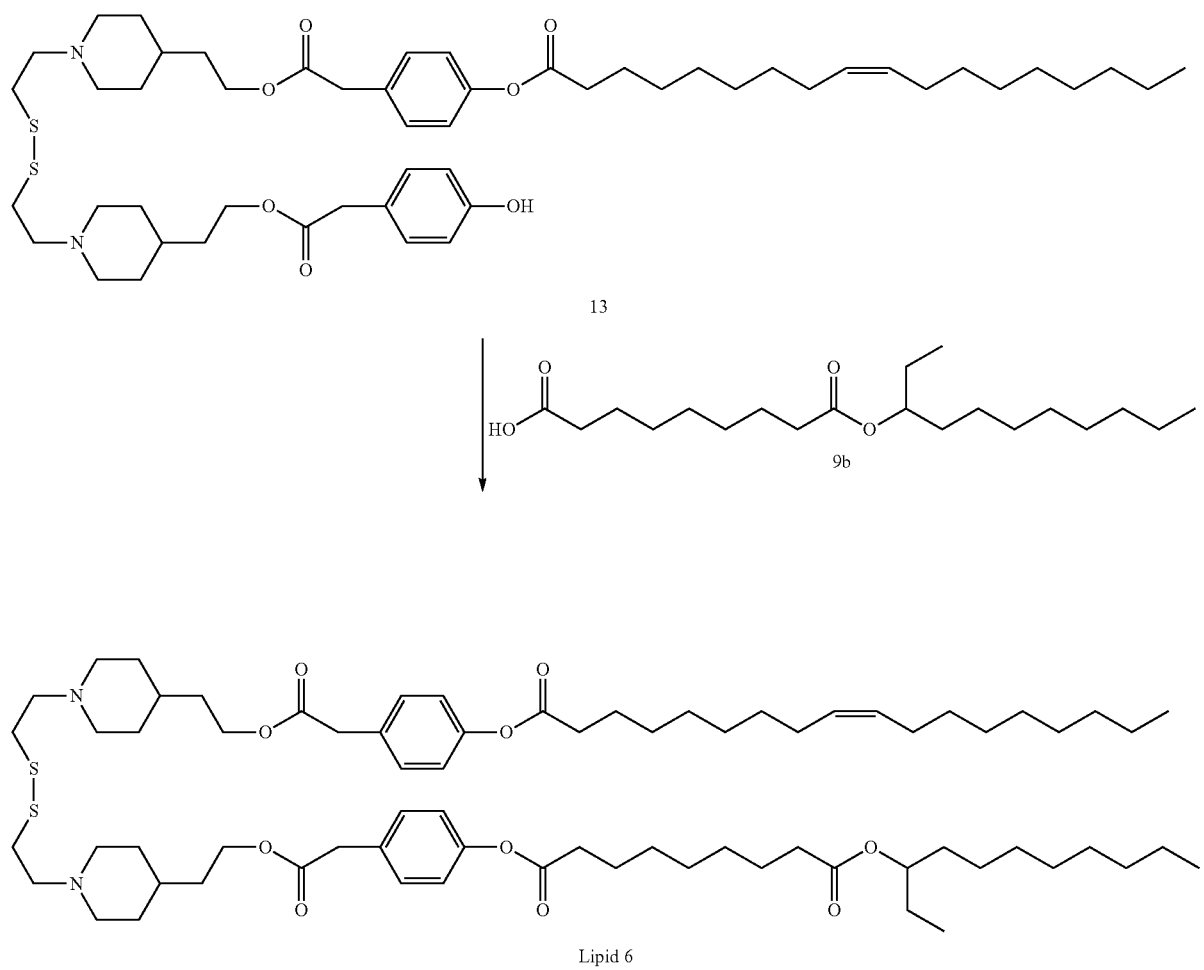

Synthesis of 1-(4-(2-(2-(1-(2-((2-(4-(2-(2-(4-(oleoyloxy)phenyl)acetoxy)ethyl)piperidin-1-yl)ethyl)disulfaneyl)ethyl)piperidin-4-yl)ethoxy)-2-oxoethyl)phenyl) 9-(undecan-3-yl) nonanedioate (Lipid 6). To a stirred solution of disulfide 13 (250 mg, 0.27 mmol) and acid 9b (113 mg, 0.33 mmol) in DCM (20 ml) was added DMAP (40 mg, 0.33 mmol) followed by EDCI (51 mg, 0.33 mmol). The resulting mixture was stirred at room temperature overnight, then washed with saturated sodium bicarbonate solution (20 ml), brine (20 ml) and dried over $Na_2SO_4$. Solvent was removed under reduced pressure and the residue was purified by silica gel column chromatography using 0-5% MeOH in DCM as eluent. The fraction containing the desired compound was evaporated to afford Lipid 6 (120 mg, 36%). $^1$H-NMR (300 MHz, d-chloroform): δ 7.31 (d, 4H), 7.05 (d, 4H), 5.36-5.40 (m, 2H), 4.86 (m, 1H), 4.11 (t, 4H), 3.62 (t, 4H), 2.77-2.90 (m, 8H), 2.55-2.71 (m, 8H), 2.30-2.34 (m, 2H), 1.96-2.05 (m, 8H), 1.77 (m, 4H), 1.58-1.67 (m, 18H), 1.30-1.58 (m, 40H), 0.89 (t, 9H).

Example 7: Synthesis of 1-(4-(2-(2-(1-(2-((2-(4-(2-(2-(4-(oleoyloxy)phenyl)acetoxy)ethyl)piperidin-1-yl)ethyl)disulfaneyl)ethyl)piperidin-4-yl)ethoxy)-2-oxoethyl)phenyl) 9-(tridecan-5-yl) nonanedioate (Lipid 7)

Synthesis of tridecanol-5-ol (8c)

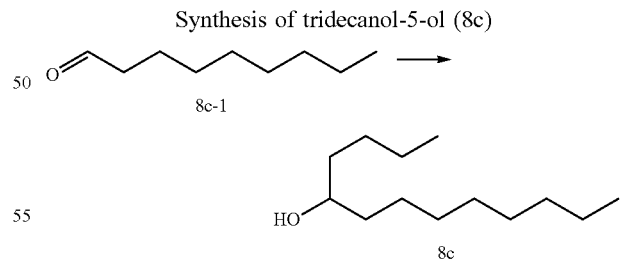

Synthesis of tridecan-5-ol (8c). To a solution of aldehyde 8c-1 (7.1 g, 0.05 mol) in 100 ml anhydrous THF was added dropwise at −78° C. a solution of 2 M butyllithium (BuLi) (27 ml) in THF. The resulted mixture was stirred at −78° C. for 2 hrs and then at room temperature for 2 hrs. The reaction was quenched by adding water and partitioned between 1 N HCl and ether. The organic layer was collected, dried over $MgSO_4$, and evaporated to give crude 8c (10 g, 100%) as a yellow oil, which was used directly for next step without further purification.

Synthesis of 9-oxo-9-(tridecan-5-yloxy)nonanoic acid (9c)

Synthesis of 1-(4-(2-(2-(1-(2-((2-(4-(2-(2-(4-(oleoyloxy) phenyl)acetoxy)ethyl)piperidin-1-yl)ethyl)disulfaneyl)

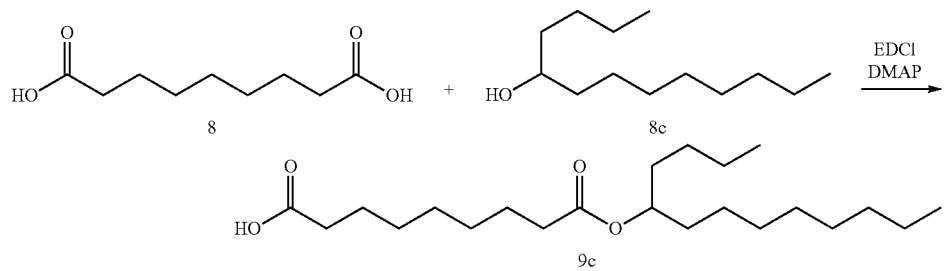

Synthesis of 9-oxo-9-(tridecan-5-yloxy)nonanoic acid (9c). To a stirred solution of nonanedioic acid (8) (9.4 g, 0.05 mol) and 8c (5 g, 0.025 mol) in DCM (500 ml) was added DMAP (3.05 g, 0.025 mol) followed by EDCI (3.88 g, 0.025 mol). The resulting mixture was stirred at room temperature overnight, then washed with 1 N HCl solution (500 ml) and water (500 ml). The organic layer was dried over $MgSO_4$, evaporated to dryness and purified by silica gel column chromatography using 0-10% MeOH in DCM as eluent. The fractions containing the desired compound were pooled and evaporated to afford 9c (2.5 g, 27%) as a white solid. $^1$H-NMR (300 MHz, d-chloroform): δ 4.84-4.87 (t, 1H), 2.28-2.34 (m, 4H), 1.58-1.63 (m, 7H), 1.26-1.32 (m, 23H), 0.85-0.87 (t, 6H).

Synthesis of Lipid 7 ethyl)piperidin-4-yl)ethoxy)-2-oxoethyl)phenyl) 9-(tridecan-5-yl) nonanedioate (Lipid 7). To a stirred solution of disulfide 13 (synthesis described in Example 6) (250 mg, 0.27 mmol) and acid 9c (116 mg, 0.33 mmol) in DCM (20 ml) was added DMAP (40 mg, 0.33 mmol) followed by EDCI (51 mg, 0.33 mmol). The resulting mixture was stirred at room temperature overnight, then washed with saturated sodium bicarbonate solution (20 ml), brine (20 ml) and dried over $Na_2SO_4$. Solvent was removed under reduced pressure and the residue was purified by silica gel column chromatography using 0-5% MeOH in DCM as eluent. The fraction containing the desired compound was evaporated to afford Lipid 7 (160 mg, 40%). $^1$H-NMR (300 MHz, d-chloroform): δ 7.29 (d, 4H), 7.04 (d, 4H), 5.29-5.34 (m, 2H), 4.86 (m, 1H), 4.11 (t, 4H), 3.58 (t, 4H), 2.77-2.90 (m, 8H), 2.51-2.79

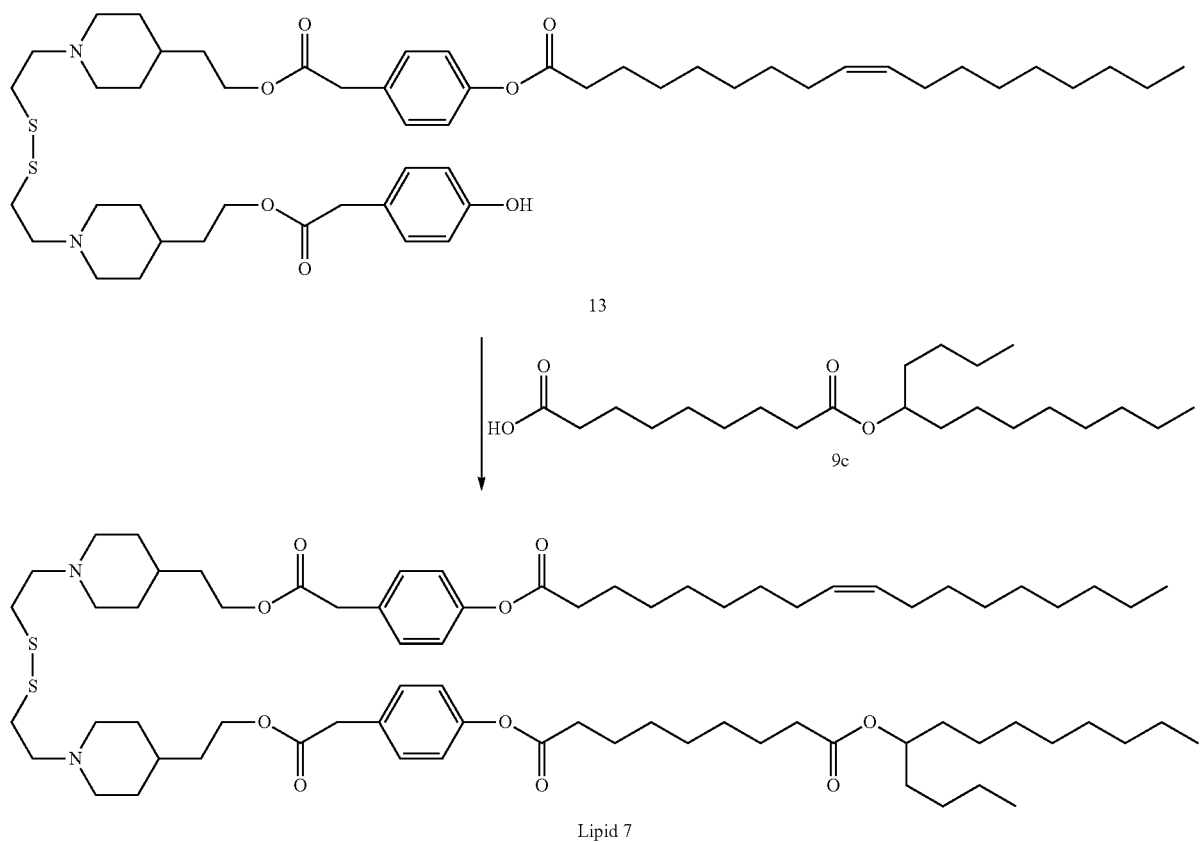

Lipid 7

(m, 8H), 2.28 (m, 2H), 1.94-2.05 (m, 8H), 1.70-1.80 (m, 4H), 1.49-1.67 (m, 18H), 1.10-1.40 (m, 46H), 0.88 (t, 9H).

Example 8: Synthesis of 1-(4-(2-(2-(1-(2-((2-(4-(2-(2-(4-(oleoyloxy)phenyl)acetoxy)ethyl)piperidin-1-yl)ethyl)disulfaneyl)ethyl)piperidin-4-yl)ethoxy)-2-oxoethyl)phenyl) 9-(pentadecan-7-yl) nonanedioate (Lipid 8)

Synthesis of pentadecan-7-ol (8d)

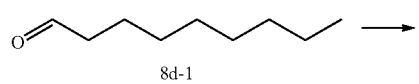

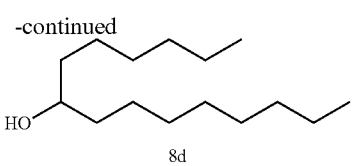

Synthesis of pentadecan-7-ol (8d). To a solution of aldehyde 8d-1 (7.1 g, 0.05 mol) in 100 ml anhydrous THF was added a solution of 2 M hexylmagnesium bromide in THF (27 ml) at −78° C. The resulted mixture was stirred at −78° C. for 2 hrs and then at room temperature overnight. The reaction was quenched by adding water and partitioned between 1 N HCl and ether. The organic layer was collected, dried over $MgSO_4$ and evaporated to give crude 8d (11 g, 100%) as a white solid, which was used directly for next step without further purification.

Synthesis of 9-oxo-9-(pentadecan-7-yloxy)nonanoic acid (9d)

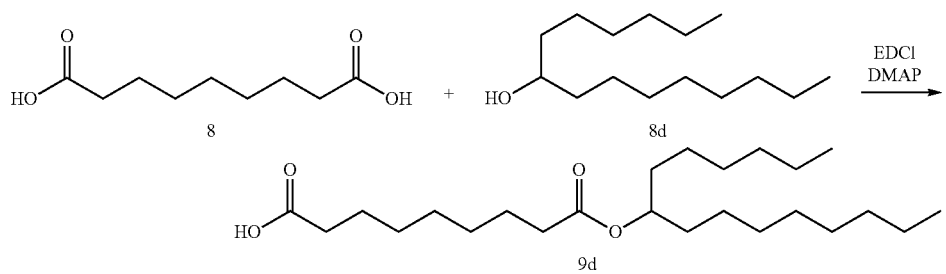

Synthesis of 9-oxo-9-(pentadecan-7-yloxy)nonanoic acid (9d). To a stirred solution of nonanedioic acid (8) (9.4 g, 0.05 mol) and pentadecane-7-ol (8d) (5.7 g, 0.025 mol) in DCM (1000 ml) was added DMAP (3.05 g, 0.025 mol) followed by EDCI (3.88 g, 0.025 mol). The resulting mixture was stirred at room temperature overnight, then washed with 1 N HCl solution (500 ml) and water (500 ml). The organic layer was dried over $MgSO_4$, evaporated to dryness, and purified by silica gel column chromatography using 0-10% MeOH in DCM as eluent. The fractions containing the desired compound were pooled and evaporated to afford 9d (6.2 g, 62%) as a white solid. $^1$H-NMR (300 MHz, d-chloroform): δ 4.86 (t, 1H), 2.28-2.34 (m, 4H), 1.58-1.63 (m, 8H), 1.26-1.32 (m, 27H), 0.85-0.87 (t, 6H).

Synthesis of Lipid 8

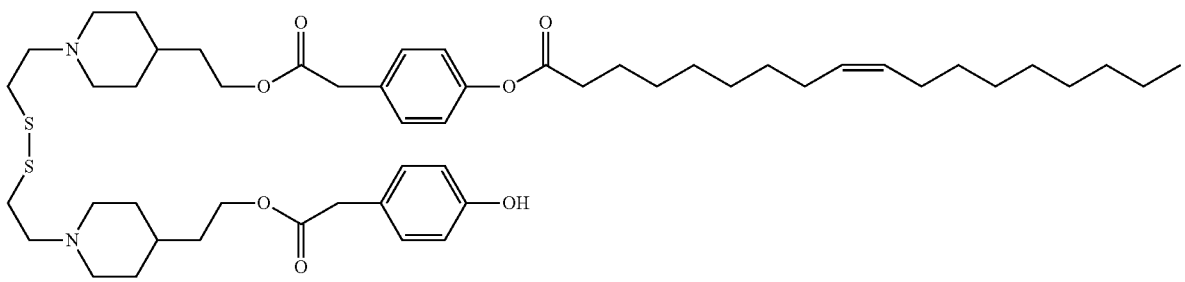

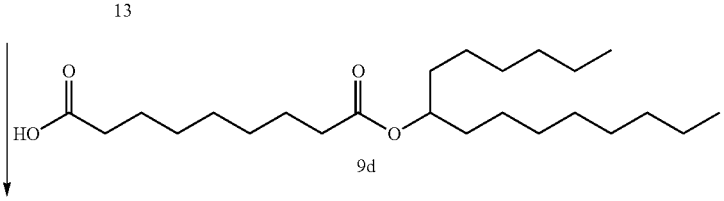

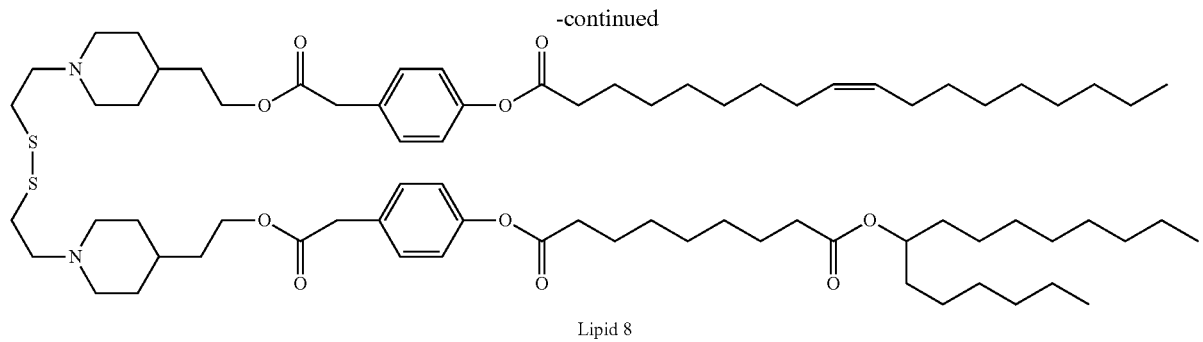

Lipid 8

Synthesis of 1-(4-(2-(2-(1-(2-((2-(4-(2-(2-(4-(oleoyloxy)phenyl)acetoxy)ethyl)piperidin-1-yl)ethyl)disulfaneyl)ethyl)piperidin-4-yl)ethoxy)-2-oxoethyl)phenyl) 9-(pentadecan-7-yl) nonanedioate (Lipid 8). To a stirred solution of disulfide 13 (synthesis described in Example 6) (250 mg, 0.27 mmol) and acid 9d (120 mg, 0.33 mmol) in DCM (20 ml) was added DMAP (40 mg, 0.33 mmol) followed by EDCI (51 mg, 0.33 mmol). The resulting mixture was stirred at room temperature overnight, then washed with saturated sodium bicarbonate solution (20 ml), brine (20 ml) and dried over $Na_2SO_4$. Solvent was removed under reduced pressure and the residue was purified by silica gel column chromatography using 0-5% MeOH in DCM as eluent. The fraction containing the desired compound was evaporated to afford Lipid 8 (170 mg, 40%). $^1$H-NMR (300 MHz, d-chloroform): δ 7.29 (d, 4H), 7.04 (d, 4H), 5.29-5.34 (m, 2H), 4.86 (m, 1H), 4.11 (t, 4H), 3.58 (t, 4H), 2.80-2.93 (m, 8H), 2.51-2.68 (m, 8H), 2.28 (m, 2H), 1.97-2.05 (m, 8H), 1.70-1.80 (m, 4H), 1.50-1.70 (m, 18H), 1.10-1.40 (m, 58H), 0.87 (t, 9H).

Example 9: Synthesis of 1-nonyl 9-(4-(2-oxo-2-(2-(1-(2-((2-(4-(2-(2-(4-((9-oxo-9-(undecan-3-yloxy)nonanoyl)oxy)phenyl)acetoxy)ethyl)piperidin-1-yl)ethyl)disulfaneyl)ethyl)piperidin-4-yl)ethoxy)ethyl)phenyl) nonanedioate (Lipid 9)

Synthesis of 1-(4-(2-(2-(1-(2-((2-(4-(2-(2-(4-hydroxyphenyl)acetoxy)ethyl)piperidin-1-yl)ethyl)disulfaneyl)ethyl)piperidin-4-yl)ethoxy)-2-oxoethyl)phenyl) 9-nonyl nonanedioate (14)

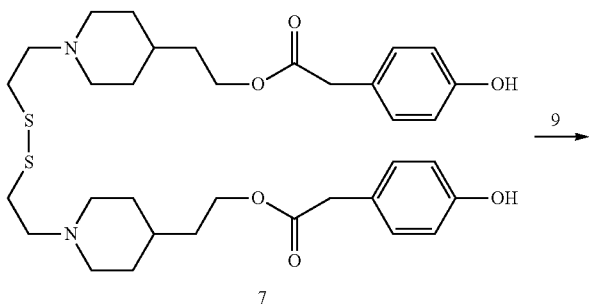

7

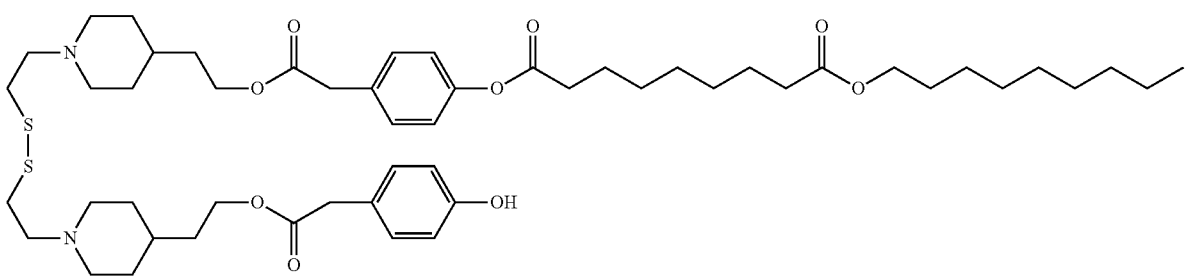

14

Synthesis of 1-(4-(2-(2-(1-(2-((2-(4-(2-(2-(4-hydroxyphenyl)acetoxy)ethyl)piperidin-1-yl)ethyl)disulfaneyl)ethyl)piperidin-4-yl)ethoxy)-2-oxoethyl)phenyl) 9-nonyl nonanedioate (14). To a stirred solution of disulfide 7 (step-by-step synthesis described in Example 1) (3.1 g, 4.8 mmol) and 9-(nonyloxy)-9-oxononanoic acid (9) (synthesis described in Example 1) (1.51 g, 4.8 mmol) in dichloromethane (200 ml) was added DMAP (587 mg, 4.8 mmol) followed by EDCI (746 mg, 4.8 mmol). The resulting mixture was stirred at room temperature. overnight, then a saturated sodium bicarbonate solution (50 ml) was added. The reaction mixture was extracted with dichloromethane (2×50 ml). The combined organic phase was washed with brine (30 ml), dried over $Na_2SO_4$ and concentrated. The residue was purified by silica gel column chromatography using 0-5% MeOH in DCM as eluent to give the desired product 14 (2.47 g, 55%). The product was used directly in the next step without further characterization.

Synthesis of 1-nonyl 9-(4-(2-oxo-2-(2-(1-(2-((2-(4-(2-(2-(4-((9-oxo-9-(undecan-3-yloxy)nonanoyl)oxy)phenyl)acetoxy)ethyl)piperidin-1-yl)ethyl)disulfaneyl)ethyl)piperidin-4-yl)ethoxy)ethyl)phenyl) nonanedioate (Lipid 9). To a stirred solution of disulfide 14 (250 mg, 0.26 mmol) and acid 9b (synthesis described in Example 6) (110 mg, 0.32 mmol) in dichloromethane (20 ml) was added DMAP (46 mg, 0.37 mmol) followed by EDCI (50 mg, 0.32 mmol). The resulting mixture was stirred at room temperature overnight, then washed with saturated sodium bicarbonate solution (20 ml), brine (20 ml) and dried over $Na_2SO_4$. Solvent was removed under reduced pressure and the residue was purified by silica gel column chromatography using 0-5% MeOH in DCM as eluent. The fraction containing the desired compound was evaporated to afford Lipid 9 (230 mg, 68%). $^1$H-NMR (300 MHz, d-chloroform): δ 7.28 (d, 4H), 7.04 (d, 4H), 4.86 (m, 1H), 4.06-4.12 (t, 4H), 4.04 (t, 2H), 3.59 (s, 4H), 2.60-2.90 (m, 8H), 2.27-2.60 (m, 10H), 1.97 (t, 3H), 1.52-1.80 (m, 18H), 1.10-1.40 (m, 40H), 0.88 (t, 9H).

Synthesis of Lipid 9

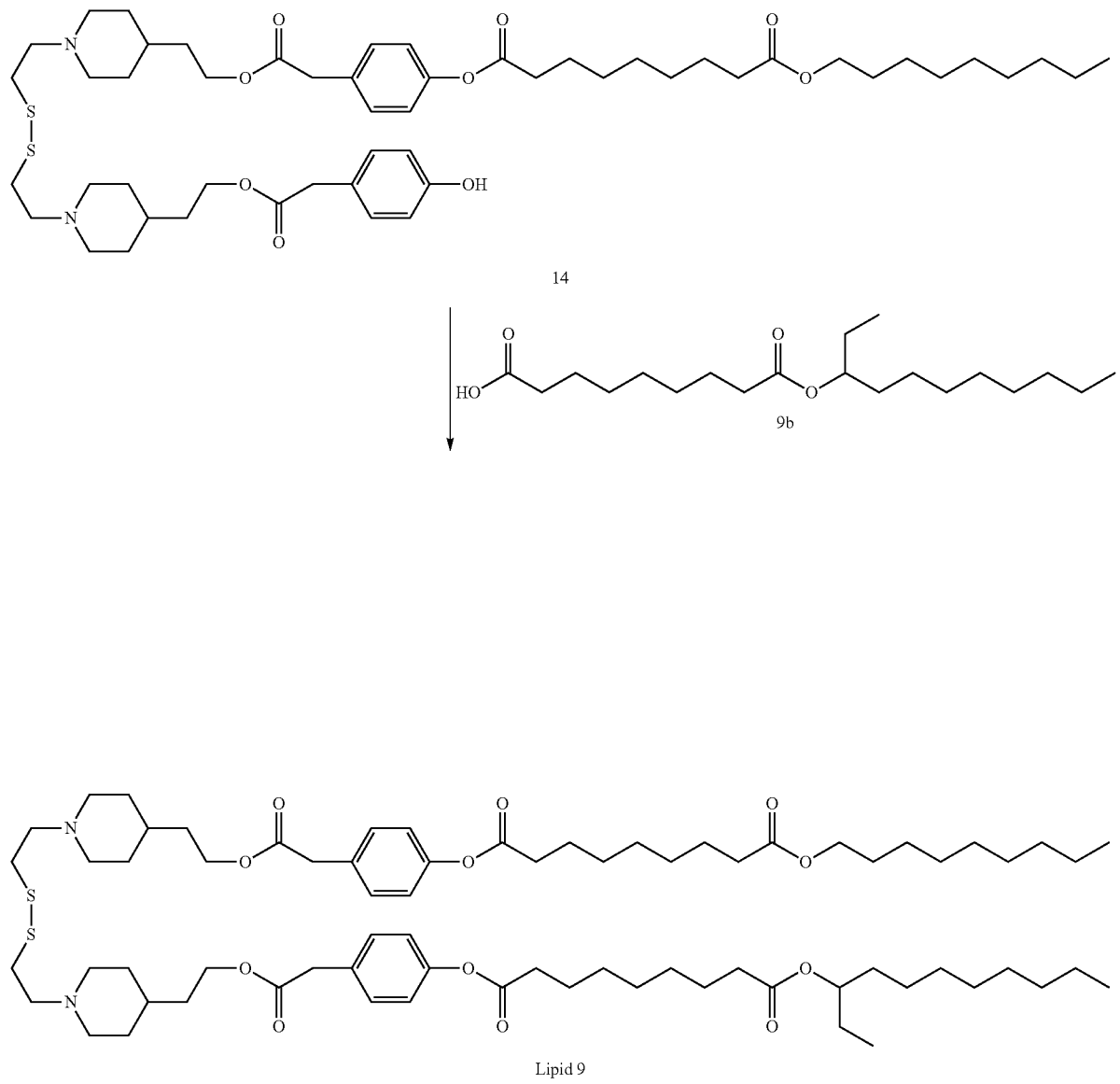

Lipid 9

Example 10: Synthesis of 1-nonyl 9-(4-(2-oxo-2-(2-(1-(2-((2-(4-(2-(2-(4-((9-oxo-9-(tridecan-5-yloxy)nonanoyl)oxy)phenyl)acetoxy)ethyl)piperidin-1-yl)ethyl)disulfaneyl)ethyl)piperidin-4-yl)ethoxy)ethyl)phenyl) nonanedioate (Lipid 10)

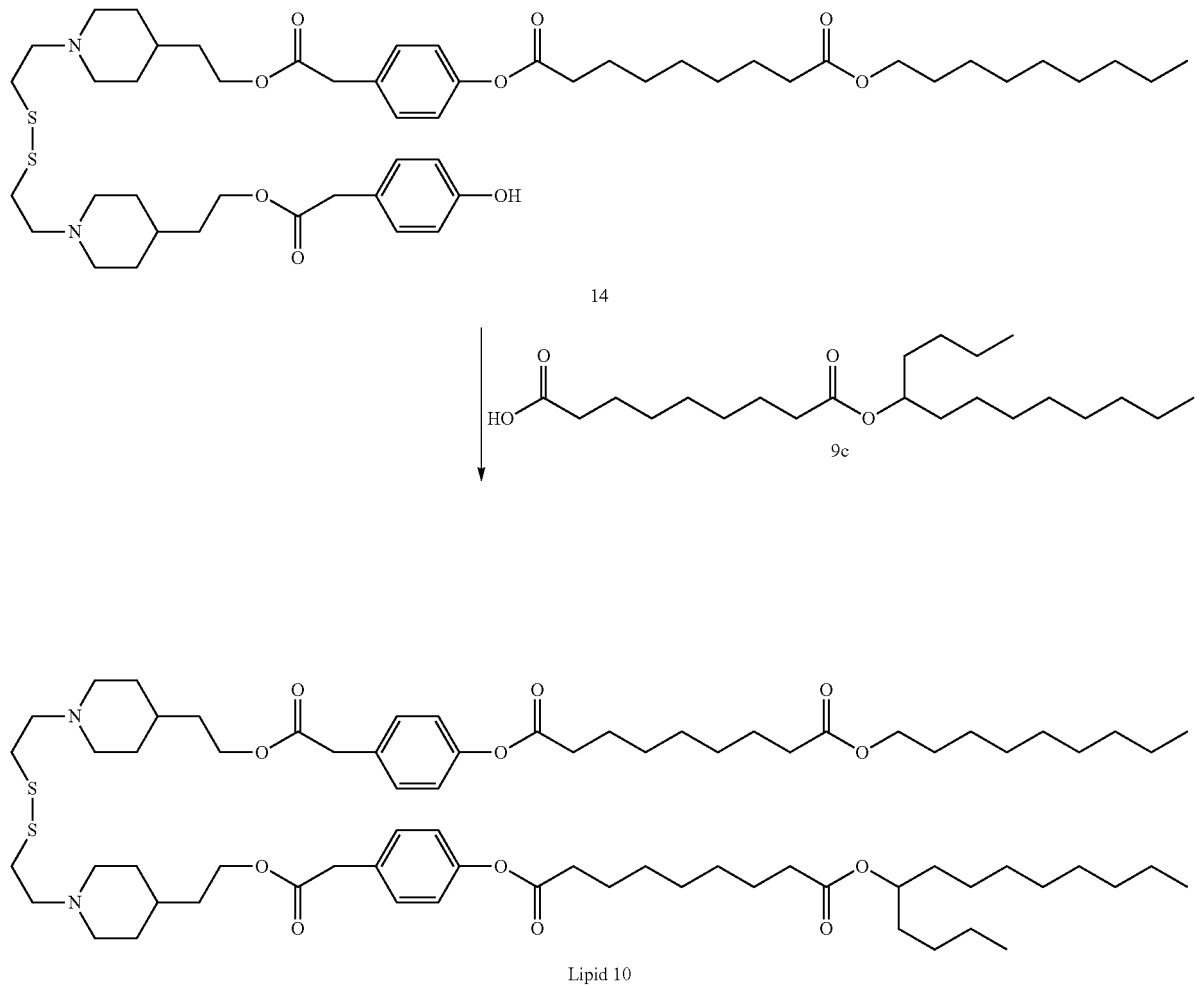

Synthesis of 1-nonyl 9-(4-(2-oxo-2-(2-(1-(2-((2-(4-(2-(2-(4-((9-oxo-9-(tridecan-5-yloxy)nonanoyl)oxy)phenyl)acetoxy)ethyl)piperidin-1-yl)ethyl)disulfaneyl)ethyl)piperidin-4-yl)ethoxy)ethyl)phenyl) nonanedioate (Lipid 10). To a stirred solution of disulfide 14 (synthesis described in Example 9) (330 mg, 0.35 mmol) and acid 9c (synthesis described in Example 7 (143 mg, 0.39 mmol) in dichloromethane (20 ml) was added DMAP (47 mg, 0.39 mmol) followed by EDCI (60 mg, 0.39 mmol). The resulting mixture was stirred at room temperature overnight, then washed with saturated sodium bicarbonate solution (20 ml), brine (20 ml) and dried over $Na_2SO_4$. Solvent was removed under reduced pressure and the residue was purified by silica gel column chromatography using 0-5% methanol in dichloromethane as eluent. The fraction containing the desired compound was evaporated to afford Lipid 10 (150 mg, 33%). $^1$H-NMR (300 MHz, d-chloroform): δ 7.26 (d, 4H), 7.03 (d, 4H), 4.86 (m, 1H), 4.05-4.11 (t, 6H), 3.58 (s, 4H), 2.80-2.90 (m, 8H), 2.50-2.70 (m, 8H), 2.26-2.29 (m, 4H), 1.92-1.99 (m, 4H), 1.50-1.80 (m, 24H), 1.16-1.40 (m, 46H), 0.87 (t, 9H).

Example 11: Synthesis of 1-nonyl 9-(4-(2-oxo-2-(2-(1-(2-((2-(4-(2-(2-(4-((9-oxo-9-(pentadecan-7-yloxy)nonanoyl)oxy)phenyl)acetoxy)ethyl)piperidin-1-yl)ethyl)disulfaneyl)ethyl)piperidin-4-yl)ethoxy)ethyl)phenyl) nonanedioate (Lipid 11)

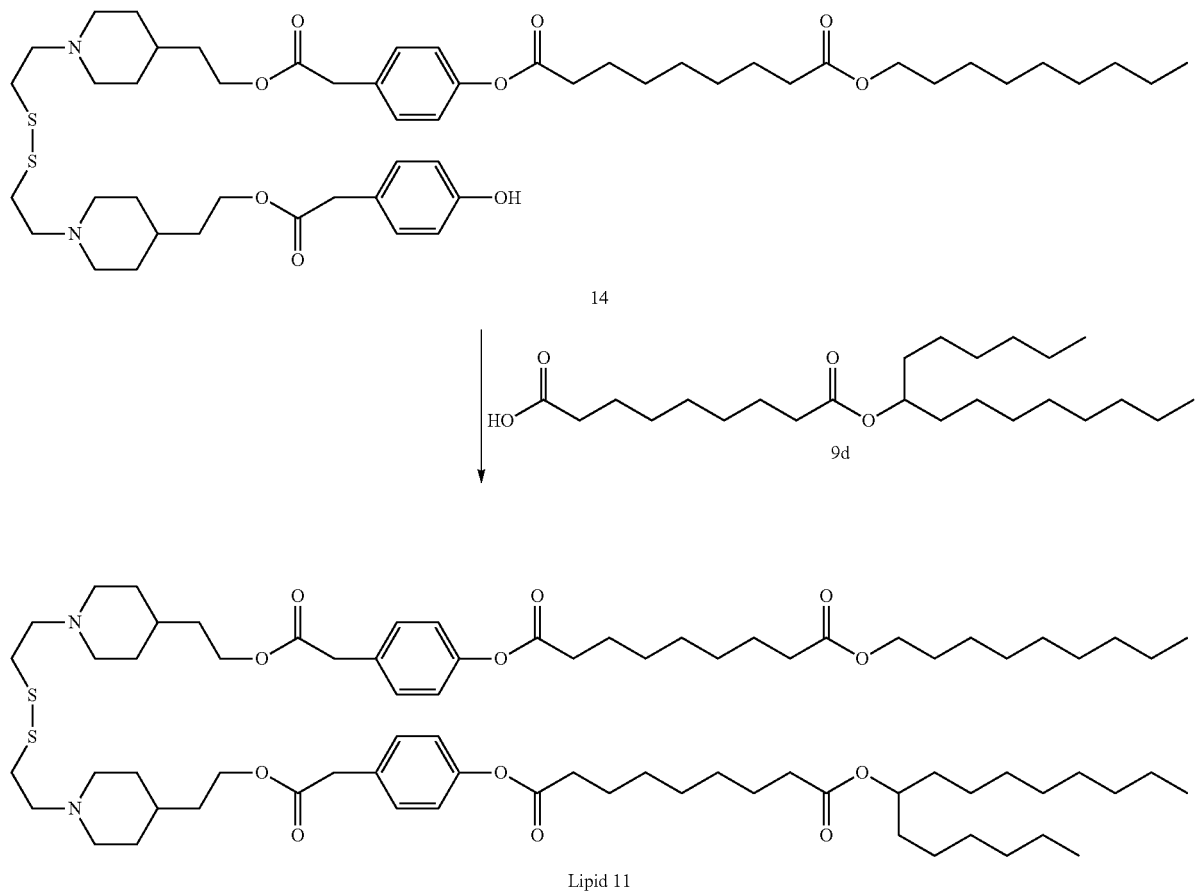

Synthesis of 1-nonyl 9-(4-(2-oxo-2-(2-(1-(2-((2-(4-(2-(2-(4-((9-oxo-9-(pentadecan-7-yloxy)nonanoyl)oxy)phenyl)acetoxy)ethyl)piperidin-1-yl)ethyl)disulfaneyl)ethyl)piperidin-4-yl)ethoxy)ethyl)phenyl) nonanedioate (Lipid 11). To a stirred solution of disulfide 14 (synthesis described in Example 9) (260 mg, 0.28 mmol) and acid 9d (synthesis described in Example 8) (122 mg, 0.3 mmol) in DCM (20 ml) was added DMAP (37 mg, 0.3 mmol) followed by EDCI (47 mg, 0.3 mmol). The resulting mixture was stirred at room temperature overnight, then washed with saturated sodium bicarbonate solution (20 ml), brine (20 ml) and dried over $Na_2SO_4$. Solvent was removed under reduced pressure and the residue was purified by silica gel column chromatography using 0-5% MeOH in DCM as eluent. The fraction containing the desired compound was evaporated to afford Lipid 11 (110 mg, 30%). $^1$H-NMR of Lipid 11 (300 MHz, d-chloroform): δ 7.26 (d, 4H), 7.02 (d, 4H), 4.86 (m, 1H), 4.05-4.11 (t, 6H), 3.59 (s, 4H), 2.80-2.90 (m, 8H), 2.50-2.70 (m, 8H), 2.27-2.29 (m, 4H), 1.90-2.20 (t, 4H), 1.50-1.82 (m, 24H), 1.10-1.40 (m, 50H), 0.87 (t, 9H).

The following Lipids 12-20 in Table 4 were prepared following similar procedures with the appropriate starting materials and other modifications that would be within the knowledge of the person having ordinary skill in the art.

TABLE 4

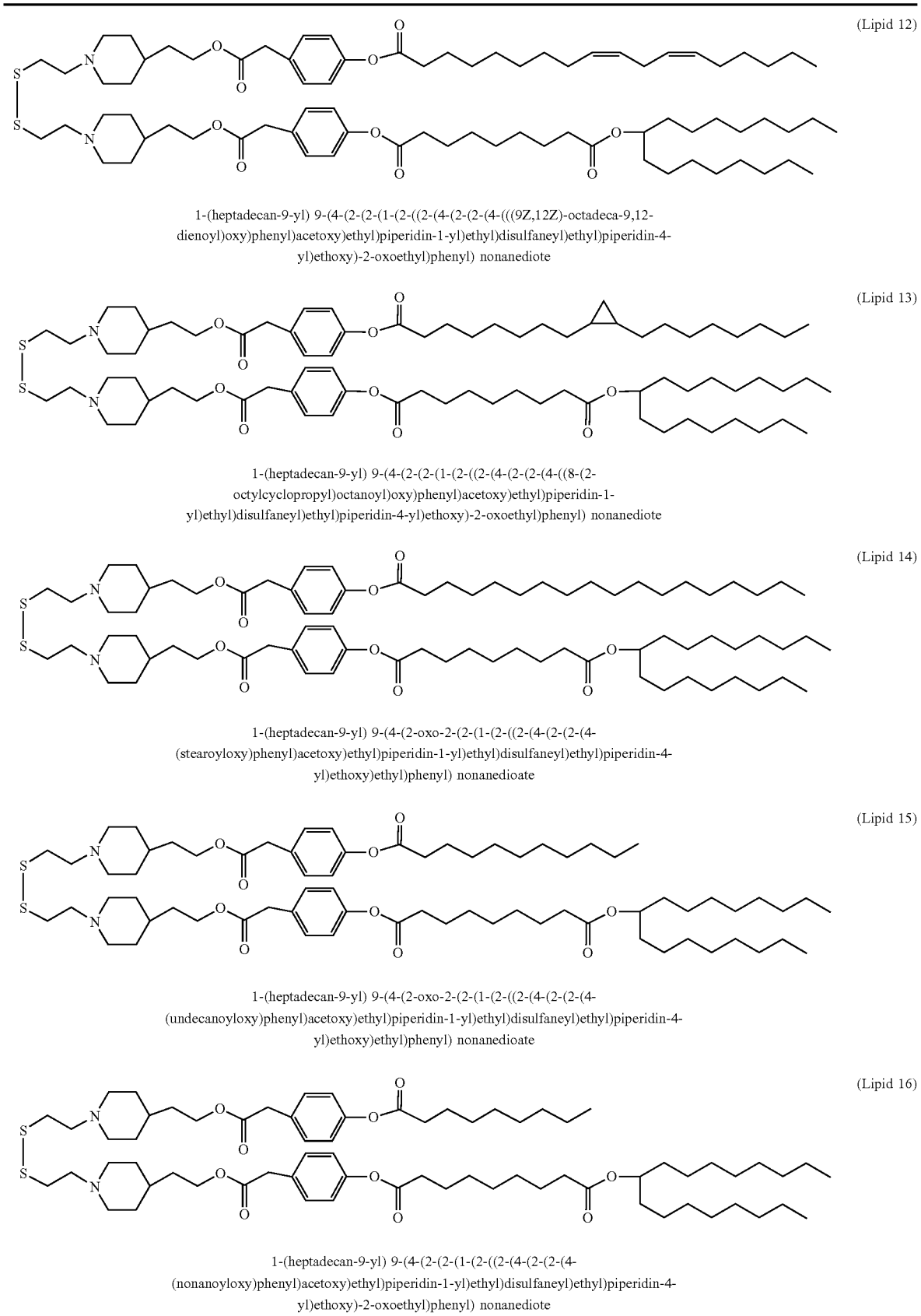

(Lipid 12)

1-(heptadecan-9-yl) 9-(4-(2-(2-(1-(2-((2-(4-(2-(2-(4-(((9Z,12Z)-octadeca-9,12-dienoyl)oxy)phenyl)acetoxy)ethyl)piperidin-1-yl)ethyl)disulfaneyl)ethyl)piperidin-4-yl)ethoxy)-2-oxoethyl)phenyl) nonanediote (Lipid 13)

1-(heptadecan-9-yl) 9-(4-(2-(2-(1-(2-((2-(4-(2-(2-(4-((8-(2-octylcyclopropyl)octanoyl)oxy)phenyl)acetoxy)ethyl)piperidin-1-yl)ethyl)disulfaneyl)ethyl)piperidin-4-yl)ethoxy)-2-oxoethyl)phenyl) nonanediote (Lipid 14)

1-(heptadecan-9-yl) 9-(4-(2-oxo-2-(2-(1-(2-((2-(4-(2-(2-(4-(stearoyloxy)phenyl)acetoxy)ethyl)piperidin-1-yl)ethyl)disulfaneyl)ethyl)piperidin-4-yl)ethoxy)ethyl)phenyl) nonanedioate (Lipid 15)

1-(heptadecan-9-yl) 9-(4-(2-oxo-2-(2-(1-(2-((2-(4-(2-(2-(4-(undecanoyloxy)phenyl)acetoxy)ethyl)piperidin-1-yl)ethyl)disulfaneyl)ethyl)piperidin-4-yl)ethoxy)ethyl)phenyl) nonanedioate (Lipid 16)

1-(heptadecan-9-yl) 9-(4-(2-(2-(1-(2-((2-(4-(2-(2-(4-(nonanoyloxy)phenyl)acetoxy)ethyl)piperidin-1-yl)ethyl)disulfaneyl)ethyl)piperidin-4-yl)ethoxy)-2-oxoethyl)phenyl) nonanediote TABLE 4-continued

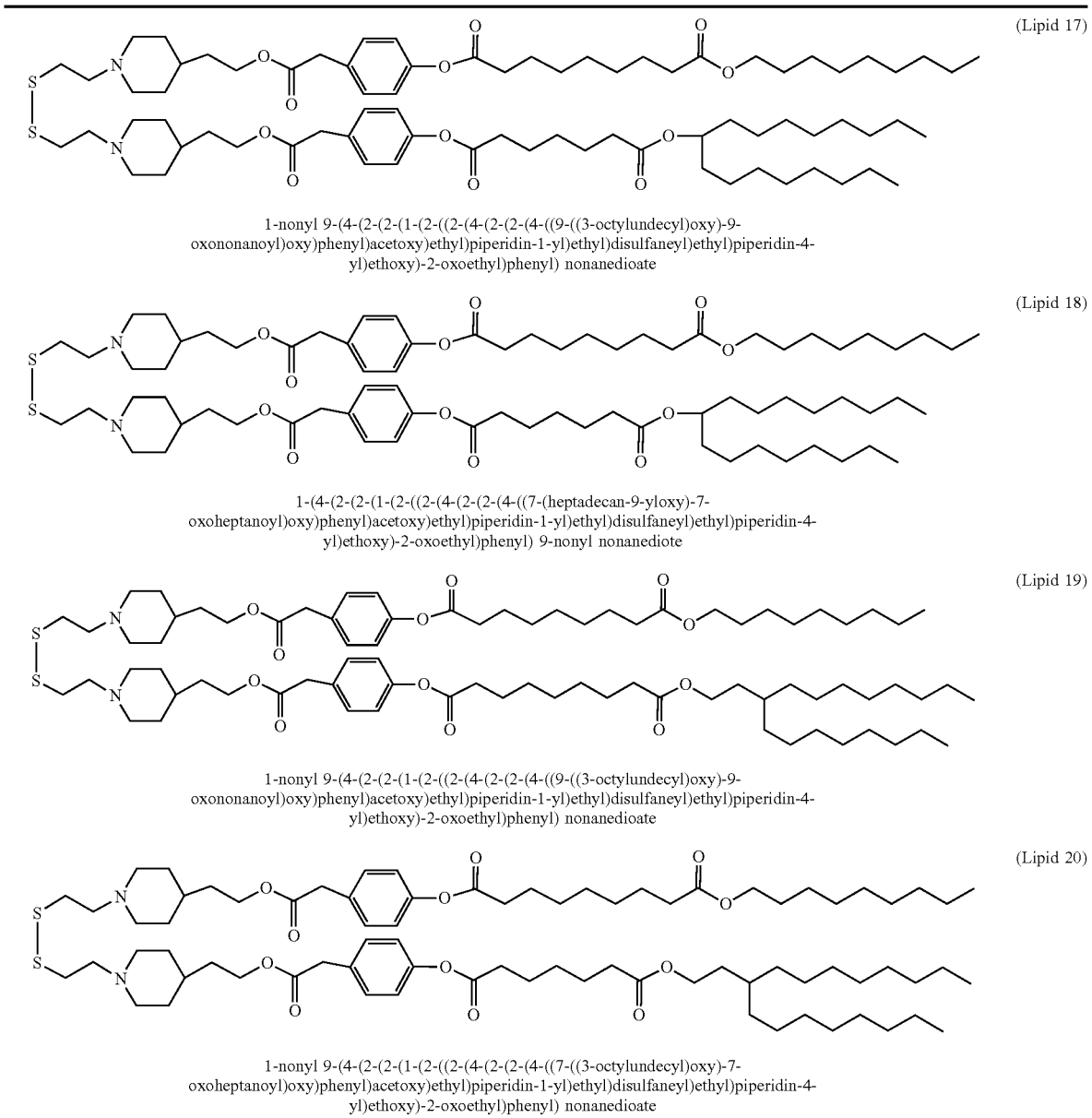

1-nonyl 9-(4-(2-(2-(1-(2-((2-(4-(2-(2-(4-((9-((3-octylundecyl)oxy)-9-
oxononanoyl)oxy)phenyl)acetoxy)ethyl)piperidin-1-yl)ethyl)disulfaneyl)ethyl)piperidin-4-
yl)ethoxy)-2-oxoethyl)phenyl) nonanedioate
(Lipid 17)

1-(4-(2-(2-(1-(2-((2-(4-(2-(2-(4-((7-(heptadecan-9-yloxy)-7-
oxoheptanoyl)oxy)phenyl)acetoxy)ethyl)piperidin-1-yl)ethyl)disulfaneyl)ethyl)piperidin-4-
yl)ethoxy)-2-oxoethyl)phenyl) 9-nonyl nonanediote
(Lipid 18)

1-nonyl 9-(4-(2-(2-(1-(2-((2-(4-(2-(2-(4-((9-((3-octylundecyl)oxy)-9-
oxononanoyl)oxy)phenyl)acetoxy)ethyl)piperidin-1-yl)ethyl)disulfaneyl)ethyl)piperidin-4-
yl)ethoxy)-2-oxoethyl)phenyl) nonanedioate
(Lipid 19)

1-nonyl 9-(4-(2-(2-(1-(2-((2-(4-(2-(2-(4-((7-((3-octylundecyl)oxy)-7-
oxoheptanoyl)oxy)phenyl)acetoxy)ethyl)piperidin-1-yl)ethyl)disulfaneyl)ethyl)piperidin-4-
yl)ethoxy)-2-oxoethyl)phenyl) nonanedioate
(Lipid 20)

Example 2: Preparation of Lipid Nanoparticles

Lipid nanoparticles (LNP) were prepared at a total lipid to ceDNA weight ratio of approximately 10:1 to 30:1. Briefly, an ionizable lipid of the present invention, a non-cationic lipid (e.g., distearoylphosphatidylcholine (DSPC)), a component to provide membrane integrity (such as a sterol, e.g., cholesterol) and a conjugated lipid molecule (such as a PEG-lipid, e.g., 1-(monomethoxy-polyethyleneglycol)-2,3-dimyristoylglycerol, with an average PEG molecular weight of 2000 ("PEG-DMG")), were solubilized in alcohol (e.g., ethanol) at a molar ratio of, for example, 50:10:37:3 or 20:40:38:2. The ceDNA was diluted to a desired concentration in buffer solution. For example, the ceDNA were diluted to a concentration of 0.1 mg/ml to 0.25 mg/ml in a buffer solution comprising sodium acetate, sodium acetate and magnesium chloride, citrate, malic acid, or malic acid and sodium chloride. In one example, the ceDNA was diluted to 0.2 mg/mL in 10 to 50 mM citrate buffer, pH 4. The alcoholic lipid solution was mixed with ceDNA aqueous solution using, for example, syringe pumps or an impinging jet mixer, at a ratio of about 1:5 to 1:3 (vol/vol) with total flow rates above 10 ml/min. In one example, the alcoholic lipid solution was mixed with ceDNA aqueous at a ratio of about 1:3 (vol/vol) with a flow rate of 12 ml/min. The alcohol was removed, and the buffer was replaced with PBS by dialysis. Alternatively, the buffers were replaced with PBS using centrifugal tubes. Alcohol removal and simultaneous buffer exchange were accomplished by, for example, dialysis or tangential flow filtration. The obtained lipid nanoparticles are filtered through a 0.2 m pore sterile filter.

In one study, lipid nanoparticles comprising exemplary ceDNAs were prepared using a lipid solution comprising SS-OP, DSPC, Cholesterol and DMG-PEG2000 (mol ratio 50:10:37:3) as control. In some examples, a tissue target moiety like N-Acetylgalactosamine (GalNAc) was included.

A GalNAc moiety such as tri-antennary GalNAc (GalNAc3) or tetra-antennary GalNAc (GalNAc4) can be synthesized as known in the art (see, WO2017/084987 and WO2013/166121) and chemically conjugated to lipid or PEG as well-known in the art (see, Resen et al., J. Biol. Chem. (2001) "Determination of the Upper Size Limit for Uptake and Processing of Ligands by the Asialoglycoprotein Receptor on Hepatocytes in Vitro and in Vivo" 276:375577-37584). Aqueous solutions of ceDNA in buffered solutions were prepared. The lipid solution and the ceDNA solution were mixed using an in-house procedure on a NanoAssembler at a total flow rate of 12 mL/min at a lipid to ceDNA ratio of 1:3 (v/v).

TABLE 2A

Test Material Administration in Study A

| Group No. | Animals per Group | LNP Treatment | Dose Level (mg/kg) | Dose Volume (mL/kg) | Treatment Regimen | Terminal Time Point |
|---|---|---|---|---|---|---|
| 1 | 5 | PBS | 0.25 | 5 | Once on Day 0, IV | Day 7 |
| 2 | 5 | LNP 1 | | | | |
| 3 | 5 | LNP 2 | | | | |
| 4 | 5 | LNP 3 | | | | |
| 5 | 5 | LNP 4 | | | | |
| 6 | 5 | LNP 5 | | | | |
| 7 | 5 | LNP 6 | | | | |
| 8 | 5 | LNP 7 | | | | |
| 9 | 5 | LNP 8 | | | | |
| 10 | 5 | LNP 9 | | | | |
| 11 | 5 | LNP 10 | | | | |
| 12 | 5 | LNP 11 | | | | |
| 13 | 5 | LNP 12 | | | | |

No. = Number;
IV = intravenous;
ROA = route of administration;
LNP = lipid nanoparticle

TABLE 2B

TEST MATERIAL ADMINISTRATION IN STUDY B

| Group No. | Animals per Group | LNP Treatment | Dose Level (mg/kg) | Dose Volume (mL/kg) | Treatment Regimen | Terminal Time Point |
|---|---|---|---|---|---|---|
| 14 | 5 | PBS | 0.25 | 5 | Once on Day 0, IV | Day 7 |
| 15 | 5 | LNP 13 | | | | |
| 16 | 5 | LNP 14 | | | | |
| 17 | 5 | LNP 15 | | | | |
| 18 | 5 | LNP 16 | | | | |
| 19 | 5 | LNP 17 | | | | |
| 20 | 5 | LNP 18 | | | | |

No. = Number;
IV = intravenous;
ROA = route of administration;
LNP = lipid nanoparticle

TABLE 2C

Test Material Administration in Study C

| Group No. | Animals per Group | LNP Treatment | Dose Level (mg/kg) | Dose Volume (mL/kg) | Treatment Regimen | Terminal Time Point |
|---|---|---|---|---|---|---|
| 21 | 5 | PBS | 0.25 | 5 | Once on Day 0, IV | Day 7 |
| 22 | 5 | LNP 19 | 0.25 | | | |
| 23 | 5 | LNP 19 | 1 | | | |
| 24 | 5 | LNP 20 | 0.25 | | | |
| 25 | 5 | LNP 20 | 1 | | | |

TABLE 2C-continued

Test Material Administration in Study C

| Group No. | Animals per Group | LNP Treatment | Dose Level (mg/kg) | Dose Volume (mL/kg) | Treatment Regimen | Terminal Time Point |
|---|---|---|---|---|---|---|
| 26 | 5 | LNP 21 | 0.25 | | | |
| 27 | 5 | LNP 21 | 1 | | | |

No. = Number;
IV = intravenous;
ROA = route of administration;
LNP = lipid nanoparticle

TABLE 2D

Test Material Administration in Study D

| Group No. | Animals per Group | LNP Treatment | Dose Level (mg/kg) | Dose Volume (mL/kg) | Treatment Regimen | Terminal Time Point |
|---|---|---|---|---|---|---|
| 28 | 5 | PBS | 0.25 | 5 | Once on Day 0, IV | Day 7 |
| 29 | 5 | LNP 22 | | | | |
| 30 | 5 | LNP 23 | | | | |
| 31 | 5 | LNP 24 | | | | |
| 32 | 5 | LNP 25 | | | | |
| 33 | 5 | LNP 26 | | | | |

No. = Number;
IV = intravenous;
ROA = route of administration;
LNP = lipid nanoparticle

TABLE 2E

Test Material Administration in Study E

| Group No. | Animals per Group | LNP Treatment | Dose Level (mg/kg) | Dose Volume (mL/kg) | Treatment Regimen | Terminal Time Point |
|---|---|---|---|---|---|---|
| 34 | 5 | PBS | 0.25 | 5 | Once on Day 0, IV | Day 7 |
| 35 | 5 | LNP 27 | | | | |
| 36 | 5 | LNP 28 | | | | |
| 37 | 5 | LNP 29 | | | | |
| 38 | 5 | LNP 30 | | | | |

No. = Number;
IV = intravenous;
ROA = route of administration;
LNP = lipid nanoparticle

TABLE 3A

Description of LNP Compositions in Study A

| LNP | Components of LNP (mol ratio) |
|---|---|
| PBS | Not Applicable |
| *LNP 1 | SS-OP:DOPC:Chol:DMG-PEG2000:DSPE-PEG2000-GalNAc4 (50.7:7.2:38.6:2.9:0.48) in malic acid |
| *LNP 2 | SS-OP:DOPC:Chol:DMG-PEG2000:DSPE-PEG2000-GalNAc4 (50.7:7.2:38.6:2.9:0.48) in malic acid |
| LNP 3 | Lipid 5:DOPC:chol:DMG-PEG2000:DSPE-PEG2000-GalNAc4 (50.7:7.2:38.6:2.9:0.48) |
| LNP 4 | Lipid 2:DOPC:chol:DMG-PEG2000:DSPE-PEG2000-GalNAc4 (50.7:7.2:38.6:2.9:0.48) |
| LNP 5 | Lipid 1:DOPC:chol:DMG-PEG2000:DSPE-PEG2000-GalNAc4 (50.7:7.2:38.6:2.9:0.48) |
| LNP 6 | Lipid 3:DOPC:chol:DMG-PEG2000:DSPE-PEG2000-GalNAc4 (50.7:7.2:38.6:2.9:0.48) |
| LNP 7 | SS-OP:DOPC:Chol:DSPE-PCB1-5:DSPE-PEG2000-GalNAc4 (47.0:6.7:35.8:10.0:0.50) |
| LNP 8 | SS-OP:DOPC:Chol:DSPE-PCB1-10:DSPE-PEG2000-GalNAc4 (47.0:6.7:35.8:10.0:0.50) |

TABLE 3A-continued

Description of LNP Compositions in Study A

| LNP | Components of LNP (mol ratio) |
|---|---|
| LNP 9 | SS-OP:DOPC:Chol:DSPE-PCB1-30:DSPE-PEG2000-GalNAc4 (47.0:6.7:35.8:10.0:0.50) |
| LNP 10 | SS-OP:DOPC:Chol:DSPE-PCB1-5:DSPE-PEG2000-GalNAc4 (50.7:7.3:38.6:2.9:0.50) |
| LNP 11 | SS-OP:DOPC:Chol:DSPE-PCB1-10:DSPE-PEG2000-GalNAc4 (50.7:7.3:38.6:2.9:0.50) |
| LNP 12 | SS-OP:DOPC:Chol:DSPE-PCB1-30:DSPE-PEG2000-GalNAc4 (50.7:7.3:38.6:2.9:0.50) |

DOPC = dioleoylphosphatidylcholine; Chol = Cholesterol; DSPE = distearoyl-phosphatidyl-ethanolamine; DMG-PEG2000 = 1-(monomethoxy-polyethyleneglycol)-2,3-dimyristoylglycerol (PEG$_{2000}$-DMG); and SS-OP = COATSOME ® SS-OP (NOF); GalNAc = N-Acetylgalactosamine; GalNAc4 = tetra-antennary GalNAc
*LNP1 and LNP2 contain the same components and molar ratio of the components, but were made in different batches and used as control.

TABLE 3B

Description of LNP Compositions in Study B

| LNP | Components of LNP (mol ratio) |
|---|---|
| PBS | Not Applicable |
| LNP 13 | SS-OP:DOPC:Chol:DMG-PEG2000:DSPE-PEG2000-GalNAc4 (50.7:7.3:38.6:2.9:0.5) |
| LNP 14 | Lipid 4:DOPC:Chol:DMG-PEG2000:DSPE-PEG2000-GalNAc4 (50.7:7.3:38.6:2.9:0.5) |
| LNP 15 | Lipid 5:DOPC:Chol:DMG-PEG2000:DSPE-PEG2000-GalNAc4 (50.7:7.3:38.6:2.9:0.5) |
| LNP 16 | Lipid 2:DOPC:Chol:DMG-PEG2000:DSPE-PEG2000-GalNAc4 (50.7:7.3:38.6:2.9:0.5) |
| LNP 17 | Lipid 1:DOPC:Chol:DMG-PEG2000:DSPE-PEG2000-GalNAc4 (50.7:7.3:38.6:2.9:0.5) |
| LNP 18 | Lipid 3:DOPC:Chol:DMG-PEG2000:DSPE-PEG2000-GalNAc4 (50.7:7.3:38.6:2.9:0.5) |

DOPC = dioleoylphosphatidylcholine; Chol = Cholesterol; DSPE = distearoyl-phosphatidyl-ethanolamine; DMG-PEG2000 = 1-(monomethoxy-polyethyleneglycol)-2,3-dimyristoylglycerol (PEG$_{2000}$-DMG); and SS-OP = COATSOME ® SS-OP (NOF); GalNAc = N-Acetylgalactosamine; GalNAc4 = tetra-antennary GalNAc

TABLE 3C

Description of LNP Compositions in Study C

| LNP | Components of LNP (mol ratio) |
|---|---|
| PBS | Not Applicable |
| LNP 19 | SS-OP:DOPC:Chol:DMG-PEG2000:DSPE-PEG2000-GalNAc4 (50.7:7.3:38.6:2.9:0.5) |
| LNP 20 | Lipid 1:DOPC:Chol:DMG-PEG2000:DSPE-PEG2000-GalNAc4 (50.7:7.3:38.6:2.9:0.5) |
| LNP 21 | Lipid 3:DOPC:Chol:DMG-PEG2000:DSPE-PEG2000-GalNAc4 (50.7:7.3:38.6:2.9:0.5) |

DOPC = dioleoylphosphatidylcholine; Chol = Cholesterol; DSPE = distearoyl-phosphatidyl-ethanolamine; DMG-PEG2000 = 1-(monomethoxy-polyethyleneglycol)-2,3-dimyristoylglycerol (PEG$_{2000}$-DMG); and SS-OP = COATSOME ® SS-OP (NOF); GalNAc = N-Acetylgalactosamine; GalNAc4 = tetra-antennary GalNAc

TABLE 3D

Description of LNP Compositions in Study D

| LNP | Components of LNP (mol ratio) |
|---|---|
| PBS | Not Applicable |
| LNP 22 | Ionizable Lipid A:DOPC:Chol:DMG-PEG2000:DSPE-PEG2000-GalNAc4 (50.7:7.3:38.6:2.9:0.5) |
| LNP 23 | SS-OP:DOPC:Chol:DMG-PEG2000:DSPE-PEG2000-GalNAc4 (50.7:7.3:38.6:2.9:0.5) |
| LNP 24 | Lipid 6:DOPC:Chol:DMG-PEG2000:DSPE-PEG2000-GalNAc4 (50.7:7.3:38.6:2.9:0.5) |
| LNP 25 | Lipid 7:DOPC:Chol:DMG-PEG2000:DSPE-PEG2000-GalNAc4 (50.7:7.3:38.6:2.9:0.5) |
| LNP 26 | Lipid 8:DOPC:Chol:DMG-PEG2000:DSPE-PEG2000-GalNAc4 (50.7:7.3:38.6:2.9:0.5) |

DOPC = dioleoylphosphatidylcholine; Chol = Cholesterol; DSPE = distearoyl-phosphatidyl-ethanolamine; DMG-PEG2000 = 1-(monomethoxy-polyethyleneglycol)-2,3-dimyristoylglycerol (PEG$_{2000}$-DMG); and SS-OP = COATSOME ® SS-OP (NOF); GalNAc = N-Acetylgalactosamine; GalNAc4 = tetra-antennary GalNAc

TABLE 3E

Description of LNP Compositions in Study E

| LNP | Components of LNP (mol ratio) |
|---|---|
| PBS | Not Applicable |
| LNP 27 | SS-OP:DOPC:Chol:DMG-PEG2000:DSPE-PEG2000-GalNAc4 (50.7:7.3:38.6:2.9:0.5) |
| LNP 28 | Lipid 9:DOPC:Chol:DMG-PEG2000:DSPE-PEG2000-GalNAc4 (50.7:7.3:38.6:2.9:0.5) |
| LNP 29 | Lipid 10:DOPC:Chol:DMG-PEG2000:DSPE-PEG2000-GalNAc4 (50.7:7.3:38.6:2.9:0.5) |
| LNP 30 | Lipid 11:DOPC:Chol:DMG-PEG2000:DSPE-PEG2000-GalNAc4 (50.7:7.3:38.6:2.9:0.5) |

DOPC = dioleoylphosphatidylcholine; Chol = Cholesterol; DSPE = distearoyl-phosphatidyl-ethanolamine; DMG-PEG2000 = 1-(monomethoxy-polyethyleneglycol)-2,3-dimyristoylglycerol (PEG$_{2000}$-DMG); and SS-OP = COATSOME ® SS-OP (NOF); GalNAc = N-Acetylgalactosamine; GalNAc4 = tetra-antennary GalNAc

TABLE 4

Blood Collection

| Group Number | Sample Collection Times Whole Blood (Tail, saphenous or orbital) SERUM[a] |
|---|---|
| 1-11 | Day 0 about 5-6 hours post Test Material dose (no less than 5.0 hours, no more than 6.5 hours) |
| Volume/ Portion | about 150 μL whole blood |
| Processing/ Storage | 1 aliquot frozen at nominally −70° C. |

[a]Whole blood was collected into serum separator tubes, with clot activator

Species (number, sex, age): CD-1 mice (N=65 and 5 spare, male, about 4 weeks of age at arrival).

Cage Side Observations: Cage side observations were performed daily.

Clinical Observations: Clinical observations were performed about 1, about 5 to about 6 and about 24 hours post the Day 0 Test Material dose. Additional observations were made per exception. Body weights for all animals, as applicable, were recorded on Days 0, 1, 2, 3, 4 & 7 (prior to euthanasia). Additional body weights were recorded as needed.

Dose Administration: Test articles (LNPs: ceDNA-Luc) were dosed at 5 mL/kg on Day 0 for Groups 1-38 by intravenous administration to lateral tail vein.

In-life Imaging: On Day 4, all animals in were dosed with luciferin at 150 mg/kg (60 mg/mL) via intraperitoneal (IP) injection at 2.5 mL/kg.≤15 minutes post each luciferin administration; all animals had an IVIS imaging session according to in vivo imaging protocol described below.

Anesthesia Recovery: Animals were monitored continuously while under anesthesia, during recovery and until mobile.

Interim Blood Collection: All animals had interim blood collected on Day 0; 5-6 hours post Test Material dose (no less than 5.0 hours, no more than 6.5 hours).

After collection animals received 0.5-1.0 mL lactated Ringer's; subcutaneously.

Whole blood for serum were collected by tail-vein nick, saphenous vein or orbital sinus puncture (under inhalant isoflurane). Whole blood was collected into a serum separator with clot activator tube and processed into one (1) aliquot of serum.

In-Vivo Imaging Protocol

Luciferin stock powder was stored at nominally −20° C.
Stored formulated luciferin in 1 mL aliquots at 2-8° C. protect from light.
Formulated luciferin was stable for up to 3 weeks at 2-8° C., protected from light and stable for about 12 hrs at room temperature (RT).
Dissolved luciferin in PBS to a target concentration of 60 mg/mL at a sufficient volume and adjusted to pH=7.4 with 5-M NaOH (about 0.5 µl/mg luciferin) and HCl (about 0.5 µL/mg luciferin) as needed.
Prepared the appropriate amount according to protocol including at least a about 50% overage.

Injection and Imaging (Note: Up to 5 Animals May be Imaged at One Time)

Shaved animal's hair coat (as needed).
Per protocol, injected 150 mg/kg of luciferin in PBS at 60 mg/mL via IP.
Imaging was performed immediately or up to 15 minutes post dose.
Set isoflurane vaporizer to 1-3% (usually @2.5%) to anesthetize the animals during imaging sessions.
Isoflurane anesthesia for imaging session:
Placed the Animal into the isoflurane chamber and wait for the isoflurane to take effect, about 2-3 minutes.
Ensured that the anesthesia level on the side of the IVIS machine was positioned to the "on" position.
Placed animal(s) into the IVIS machine Performed desired Acquisition Protocol with settings for highest sensitivity.

Results

Study A

As shown in FIG. 1, on Day 4 the group of mice treated with ceDNA-luciferase (ceDNA-luc) that were formulated with Lipid 1, Lipid 2, Lipid 3, or Lipid 5 (LNPs 5, 4, 6, and 3, respectively, of FIG. 1) exhibited equivalent or higher luciferase expressions and/or activity as compared to that of the groups treated with positive control ceDNA LNPs used in Study A (LNPs 1, 2, and 7-12, each of which was a ceDNA-luc formulated with SS-OP lipids), suggesting that the ionizable lipids described herein possess superior physical attributes as a lipid nanoparticle delivery vehicle.

Study B

Figure 2:
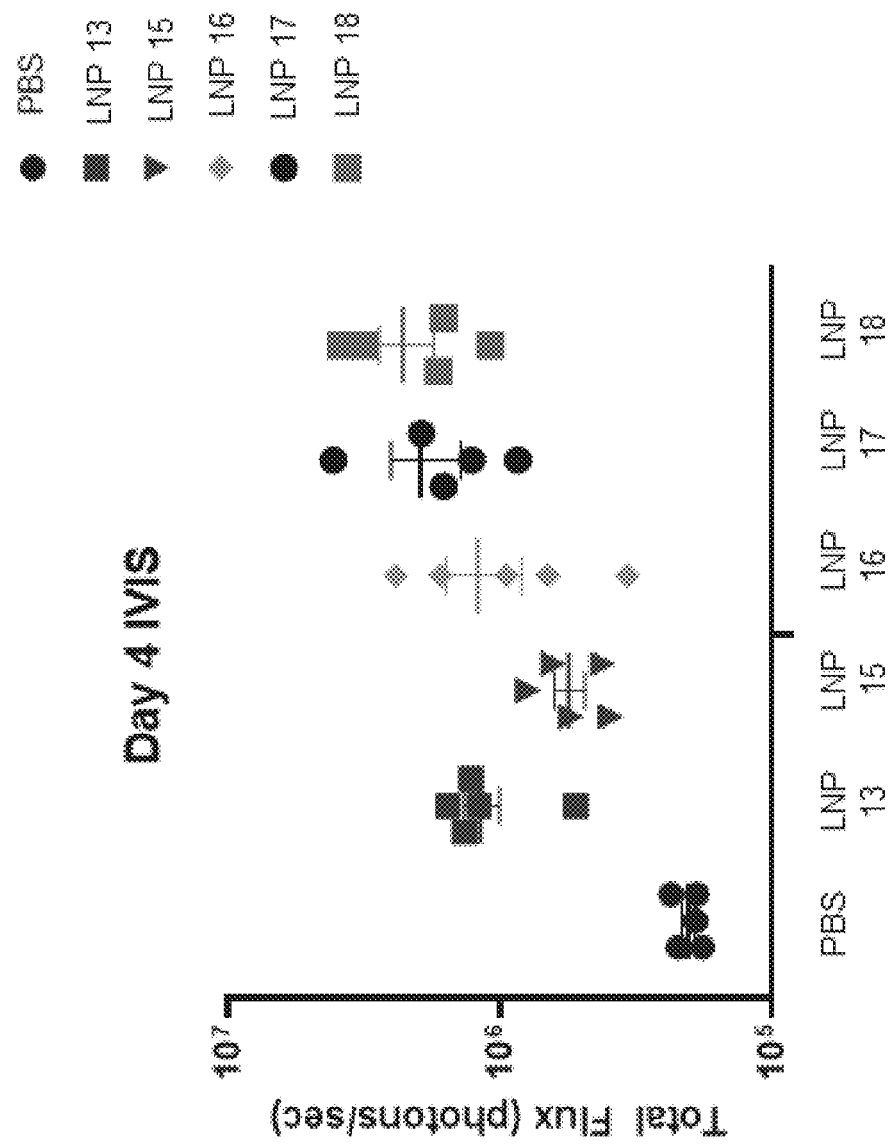
FIG. 2 shows the improvements in ceDNA-luc expression achieved by employing disclosed lipid nanoparticles (e.g., LNP 16 comprising Lipid 2, LNP 17 comprising Lipid 1, and LNP 18 comprising Lipid 3) compared to SS-OP (i.e., LNP 13), as observed in Study B.

As shown in FIG. 2, and consistent with the observations in FIG. 1 of Study A above, on Day 4 the group of mice treated with ceDNA-luc that were formulated with Lipid 1, Lipid 2, Lipid 3, or Lipid 5 (LNPs 17, 16, 18, and 15, respectively, of FIG. 2) exhibited equivalent or higher luciferase activity as compared to that of the groups treated with positive control ceDNA LNPs used in Study B (LNP 13 that was ceDNA-luc formulated with SS-OP lipid), suggesting that the ionizable lipids described herein possess superior physical attributes as a lipid nanoparticle delivery vehicle.

Study C

Figure 3:
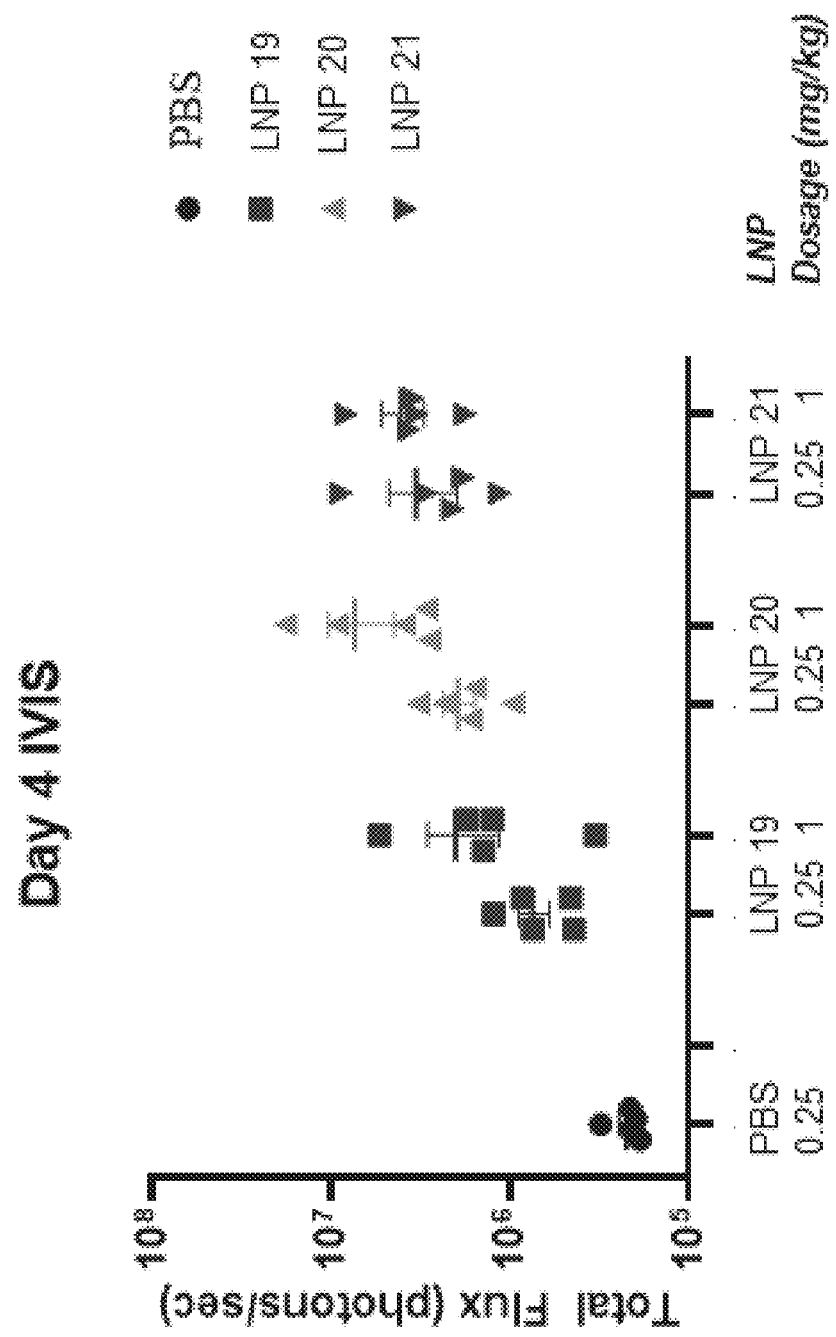
FIG. 3 shows the improvements in responsiveness to increased dosage levels, whereby an increased dosage administered to the mice leads to a greater increase in ceDNA-luc expression, achieved by employing disclosed lipid nanoparticles (e.g., LNP 20 comprising Lipid 1) compared to SS-OP (i.e., LNP 19), as observed in Study C.

Lipids 1 and 3 that exhibited the highest luciferase expression and/or activity in Studies A and B were further studied in Study C for dose response. As shown in FIG. 3, and consistent with the observations of FIGS. 1 and 2 from Studies A and B, on Day 4 the group of mice treated with ceDNA-luc that were formulated with Lipid 1 or Lipid 3 (LNPs 20 and 21, respectively, of FIG. 1) exhibited higher luciferase expression and/or activity at both 25 mg/kg and 1 mg/kg as compared to that of the groups treated with positive control ceDNA LNPs used in Study C (LNP 19 which was a ceDNA-luc formulated with SS-OP lipid), suggesting that the ionizable lipids described herein possess superior physical attributes as a lipid nanoparticle delivery vehicle. Furthermore, the results in FIG. 3 indicate that LNP 20, when increased from a dosage of 0.25 mg/kg to 1 mg/kg, exhibited a higher increase in the expression and/or activity of luciferase, as compared to LNP 19 that was also tested at the same two dosage levels. These results suggest that the LNPs formulated with the ionizable lipids of the present disclosure are more responsive to different dosage levels and that the expression level of the transgene insert in the ceDNA encapsulated by the LNPs formulated with the ionizable lipids of the present disclosure can be more easily adjusted to the level that is required to exert its therapeutic effect for a specific disease, thereby demonstrating another desirable technical feature that these ionizable lipids possess as a lipid nanoparticle delivery vehicle.

Study D

In Study D, LNPs formulated with Lipid 6, Lipid 7, and Lipid 8 (LNPs 24, 25, and 26, respectively of FIGS. 4A and 4B) and ceDNA-luc were evaluated for luciferase expression and/or activity in mice and also tolerability and compared against LNPs formulated with Ionizable Lipid A and SS-OP lipid (LNPs 22 and 23 respectively of FIGS. 4A and 4B) and ceDNA-luc, As shown in FIG. 4A, on Day 4 the group of mice treated with ceDNA-luc constructs that were formulated with Lipid 6, Lipid 7, and Lipid 8 exhibited equivalent or higher luciferase expressions and/or activity as compared to that of the groups treated with ceDNA-luc that was formulated with SS-OP lipid (i.e., LNP 23). FIG. 4B indicates that ce-DNA-luc constructs formulated with Lipid 6, Lipid 7, and Lipid 8 were also well-tolerated in mice because the treatment did not cause changes in body weight in the mice at Day 1. In contrast, as can be seen in FIG. 4B, mice treated with ceDNA-luc formulated with Ionizable Lipid A (i.e., LNP 22) suffered from significant weight loss at Day 1, thereby indicating that the lipid was not well-tolerated by the animals.

Study E

In Study E, LNPs formulated with Lipid 9, Lipid 10, and Lipid 11 (LNPs 28, 29, and 30, respectively of FIGS. 5A and 5B) and ceDNA-luc were evaluated for luciferase expression and/or activity in mice and also tolerability and compared against LNPs formulated with SS-OP lipid (LNP 27 of FIGS. 5A and 5B) and ceDNA-luc, As shown in FIG. 5A, on Day 4 the group of mice treated with ceDNA-luc constructs that were formulated with Lipid 9, Lipid 10, and Lipid 11 exhibited equivalent or higher luciferase expressions and/or activity as compared to that of the groups treated with ceDNA-luc that was formulated with SS-OP lipid (i.e., LNP 27). FIG. 5B indicates that, with the exception of an outlier data point in LNP 30, ce-DNA-luc constructs formulated with Lipid 9, Lipid 10, and Lipid 11 were generally well-tolerated in mice because the treatment did not cause significant changes in body weight in the mice at Day 1.

Thus, Studies A-E overall demonstrate that LNPs formulated with the ionizable lipids of the present disclosure: (i) have excellent in vivo expression level of the transgene insert of the ceDNA; (ii) are responsive to different dosage levels, thereby enable the in vivo expression level of the transgene insert of the ceDNA to be adjusted as necessary; and (iii) are well-tolerated in vivo.

REFERENCES

All publications and references, including but not limited to patents and patent applications, cited in this specification and Examples herein are incorporated by reference in their entirety as if each individual publication or reference were specifically and individually indicated to be incorporated by reference herein as being fully set forth. Any patent application to which this application claims priority is also incorporated by reference herein in the manner described above for publications and references.

---

---

What is claimed is:

1. A lipid represented by the Formula (I):

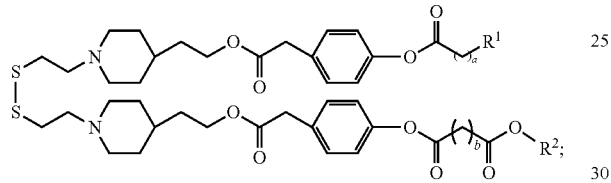

(I)

or a pharmaceutically acceptable salt thereof, wherein:
  a is an integer ranging from 1 to 20;
  b is an integer ranging from 2 to 10;
  $R^1$ is absent or is selected from the group consisting of $(C_2\text{-}C_{20})$alkenyl, $-C(O)O(C_2\text{-}C_{20})$alkyl, and cyclopropyl substituted with $(C_2\text{-}C_{20})$alkyl; and
  $R^2$ is $(C_2\text{-}C_{20})$alkyl.

2. The lipid of claim 1, or a pharmaceutically acceptable salt thereof, wherein the lipid is represented by the Formula (II):

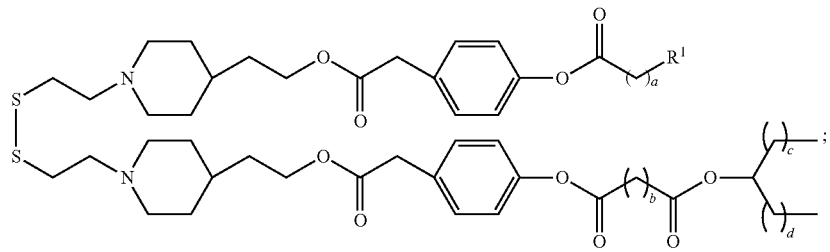

(II)

wherein c and d are each independently integers ranging from 1 to 8.

3. The lipid of claim 2, or a pharmaceutically acceptable salt thereof, wherein c and d are each independently integers ranging from 2 to 8, or from 4 to 8, or from 6 to 8.

4. The lipid of claim 2, or a pharmaceutically acceptable salt thereof, wherein c and d are each independently 1, 3, 5, or 7.

5. The lipid of claim 2, or a pharmaceutically acceptable salt thereof, wherein at least one of c and d is 7.

6. The lipid of claim 1, or a pharmaceutically acceptable salt thereof, wherein the lipid is represented by the Formula (III):

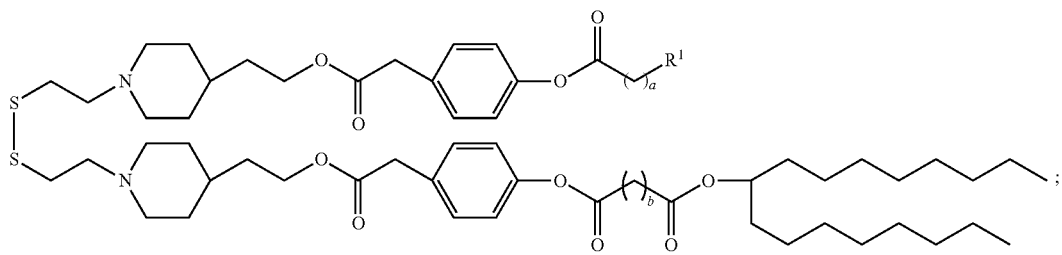

(III)

7. The lipid of claim 1, or a pharmaceutically acceptable salt thereof, wherein b is an integer ranging from 3 to 9, or from 5 to 7.

8. The lipid of claim 1, or a pharmaceutically acceptable salt thereof, wherein b is 5 or 7.

9. The lipid of claim 1, or a pharmaceutically acceptable salt thereof, wherein a is an integer ranging from 2 to 18, or from 3 to 17, or from 6 to 18, or from 4 to 12, or from 2 to 5, or from 6 to 8, or from 16 to 18, or from 9 to 11.

10. The lipid of claim 9, or a pharmaceutically acceptable salt thereof, wherein a is 3, 7, 8, 10 or 17.

11. The lipid of claim 1, or a pharmaceutically acceptable salt thereof, wherein $R^1$ is absent or is selected from the group consisting of $(C_5\text{-}C_{15})$alkenyl, —C(O)O$(C_4\text{-}C_{18})$alkyl, and cyclopropyl substituted with $(C_4\text{-}C_{16})$alkyl.

12. The lipid of claim 11, or a pharmaceutically acceptable salt thereof, wherein $R^1$ is —C(O)O$(C_4\text{-}C_{18})$alkyl, —C(O)O$(C_4\text{-}C_{12})$alkyl, or -C(O)O$(C_4\text{-}C_{10})$alkyl; and wherein the alkyl is a branched alkyl.

13. The lipid of claim 12, or a pharmaceutically acceptable salt thereof, wherein $R^1$ is —C(O)O($C_{17}$ alkyl).

14. The lipid of claim 1, or a pharmaceutically acceptable salt thereof, wherein $R^1$ is absent or is selected from the group consisting of $(C_5\text{-}C_{12})$alkenyl, —C(O)O$(C_4\text{-}C_{12})$alkyl, and cyclopropyl substituted with $(C_4\text{-}C_{12})$alkyl.

15. The lipid of claim 1, or a pharmaceutically acceptable salt thereof, wherein $R^1$ is $C_{10}$ alkenyl.

16. The lipid of claim 1, or a pharmaceutically acceptable salt thereof, wherein $R^1$ is —C(O)O$(C_2\text{-}C_{20})$alkyl, —C(O)O$(C_4\text{-}C_{18})$alkyl, —C(O)O$(C_4\text{-}C_{12})$alkyl, or -C(O)O$(C_4\text{-}C_{10})$alkyl, and wherein the alkyl is an unbranched alkyl.

17. The lipid of claim 16, or a pharmaceutically acceptable salt thereof, wherein $R^1$ is —C(O)O($C_9$ alkyl).

18. The lipid of claim 1, or a pharmaceutically acceptable salt thereof, wherein $R^1$ is selected from the group consisting of:

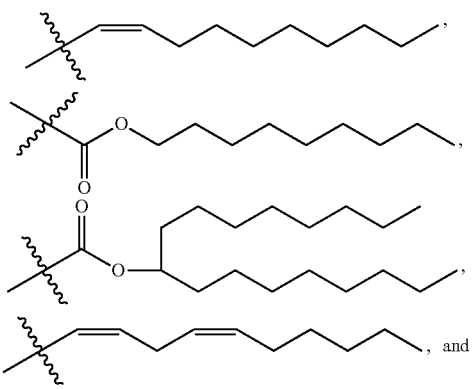

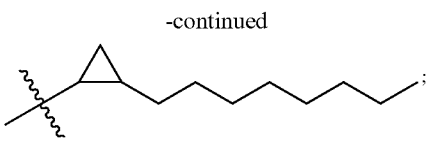

and/or wherein $R^2$ is selected from the group consisting of:

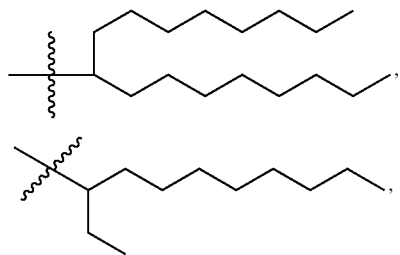

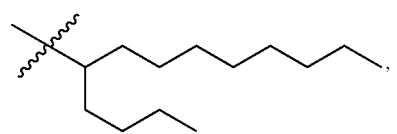

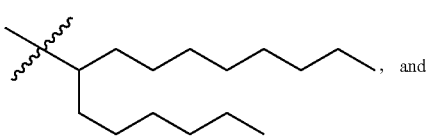

, and

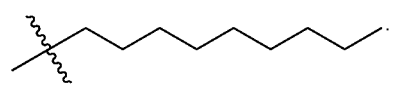

19. The lipid of claim 1, wherein the lipid is selected from the group consisting of:

TABLE 3

Exemplary ionizable lipids of the disclosure

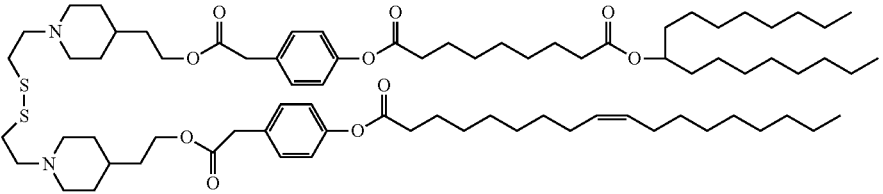 [SMILES: CCCCCCCC/C=C\CCCCCCCC(=O)Oc1ccc(CC(=O)OCCC2CCN(CCSSCCN3CCC(CCOC(=O)Cc4ccc(OC(=O)CCCCCCCC(=O)OC(CCCCCCCC)CCCCCCCC)cc4)CC3)CC2)cc1]

1-(heptadecan-9-yl) 9-(4-(2-(2-(1-(2-((2-(4-(2-(2-(4-(oleoyloxy)phenyl)acetoxy)ethyl)piperidin-1-yl)ethyl)disulfaneyl)ethyl)piperidin-4-yl)ethoxy)-2-oxoethyl)phenyl) nonanedioate Lipid 1

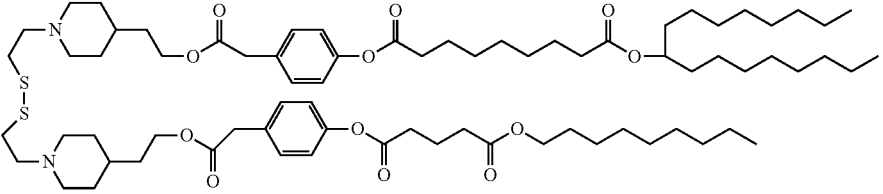 [SMILES: CCCCCCCCCOC(=O)CCCC(=O)Oc1ccc(CC(=O)OCCC2CCN(CCSSCCN3CCC(CCOC(=O)Cc4ccc(OC(=O)CCCCCCCC(=O)OC(CCCCCCCC)CCCCCCCC)cc4)CC3)CC2)cc1]

1-(heptadecan-9-yl) 9-(4-(2-(2-(1-(2-((2-(4-(2-(2-(4-((5-(nonyloyx)-5-oxopentanoyl)oxy)phenyl)acetoxy)ethyl) piperidin-1-yl)ethyl)disulfaneyl)ethyl) piperidin-4-yl)ethoxy)-2-oxoethyl)phenyl) nonanediote Lipid 2

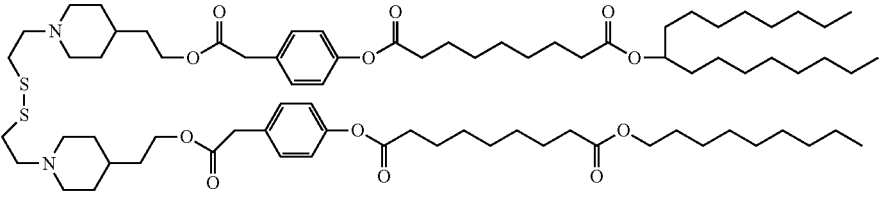 [SMILES: CCCCCCCCCOC(=O)CCCCCCCC(=O)Oc1ccc(CC(=O)OCCC2CCN(CCSSCCN3CCC(CCOC(=O)Cc4ccc(OC(=O)CCCCCCCC(=O)OC(CCCCCCCC)CCCCCCCC)cc4)CC3)CC2)cc1]

1-(heptadecan-9-yl) 9-(4-(2-(1-(2-((2-(4-(2-(2-(4-((9-(nonyloxy)-9-oxononanoyl)oxy)phenyl)acetoxy)ethyl)piperidin-1-yl)ethyl)disulfaneyl)ethyl)piperidin-4-yl)ethoxy)-2-oxoethyl)phenyl) nonanediote Lipid 3

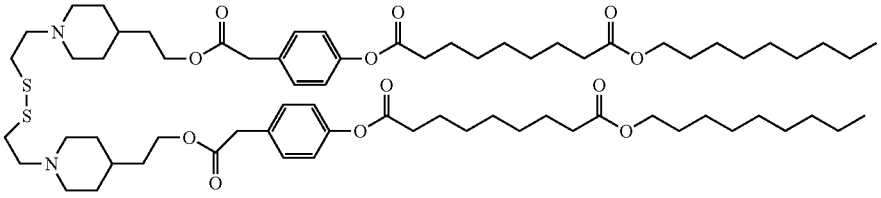 [SMILES: CCCCCCCCCOC(=O)CCCCCCCC(=O)Oc1ccc(CC(=O)OCCC2CCN(CCSSCCN3CCC(CCOC(=O)Cc4ccc(OC(=O)CCCCCCCC(=O)OCCCCCCCCC)cc4)CC3)CC2)cc1]

1-(heptadecan-9-yl) 9-(4-(2-(2-(1-(2-((2-(4-(2-(2-(4-((5-(nonyloxy)-5-oxopentanoyl)oxy)phenyl)acetoxy)ethyl) piperidin-1-yl)ethyl)disulfaneyl)ethyl)piperidin-4-yl)ethoxy)-2-oxoethyl)phenyl) nonanediote Lipid 4

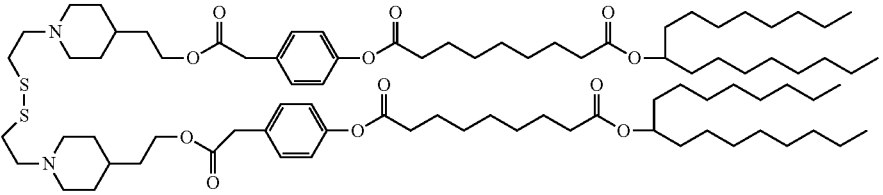 [SMILES: CCCCCCCCC(CCCCCCCC)OC(=O)CCCCCCCC(=O)Oc1ccc(CC(=O)OCCC2CCN(CCSSCCN3CCC(CCOC(=O)Cc4ccc(OC(=O)CCCCCCCC(=O)OC(CCCCCCCC)CCCCCCCC)cc4)CC3)CC2)cc1]

O'1,O1-((((((disulfanediylbis(ethane-2,1-diyl))bis(piperidine-1,4-diyl))bis(ethane-2,1-diyl))bis(oxy))bis(2-oxoethane-2,1-diyl))bis(4,1-phenylene)) 9,9'-di(heptadecan-9-yl) di(nonanediote)

Lipid 5

TABLE 3-continued

Exemplary ionizable lipids of the disclosure

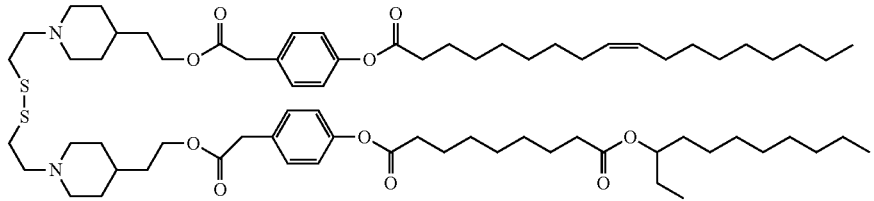 [SMILES: CCCCCCCC/C=C\CCCCCCCC(=O)Oc1ccc(CC(=O)OCCC2CCN(CCSSCCN3CCC(CCOC(=O)Cc4ccc(OC(=O)CCCCCCCC(=O)OC(CC)CCCCCCCC)cc4)CC3)CC2)cc1]

Lipid 6

1-(4-(2-(2-(1-(2-((2-(4-(2-(4-(oleoyloxy)phenyl)acetoxy)ethyl)piperidin-1-yl)ethyl)disulfaneyl)ethyl)piperidin-4-yl)ethoxy)-2-oxoethyl)phenyl) 9-(undecan-3-yl) nonanediote

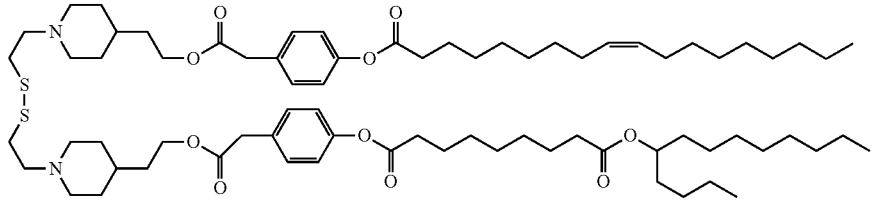 [SMILES: CCCCCCCC/C=C\CCCCCCCC(=O)Oc1ccc(CC(=O)OCCC2CCN(CCSSCCN3CCC(CCOC(=O)Cc4ccc(OC(=O)CCCCCCCC(=O)OC(CCCC)CCCCCCCC)cc4)CC3)CC2)cc1]

Lipid 7

1-(4-(2-(2-(1-(2-((2-(4-(2-(4-(oleoyloxy)phenyl)acetoxy)ethyl)piperidin-1-yl)ethyl)disulfaneyl)ethyl)piperidin-4-yl)ethoxy)-2-oxoethyl)phenyl) 9-(tridecan-5-yl) nonanediote

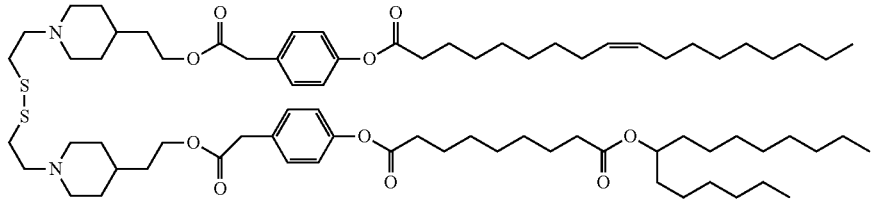 [SMILES: CCCCCCCC/C=C\CCCCCCCC(=O)Oc1ccc(CC(=O)OCCC2CCN(CCSSCCN3CCC(CCOC(=O)Cc4ccc(OC(=O)CCCCCCCC(=O)OC(CCCCCC)CCCCCCCC)cc4)CC3)CC2)cc1]

Lipid 8

1-(4-(2-(2-(1-(2-((2-(4-(2-(4-(oleoyloxy)phenyl)acetoxy)ethyl)piperidin-1-yl)ethyl)disulfaneyl)ethyl)piperidin-4-yl)ethoxy)-2-oxoethyl)phenyl 9-(pentadecan-7-yl) nonanediote

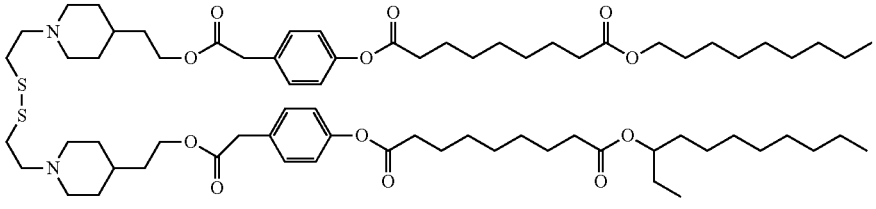 [SMILES: CCCCCCCCCOC(=O)CCCCCCCC(=O)Oc1ccc(CC(=O)OCCC2CCN(CCSSCCN3CCC(CCOC(=O)Cc4ccc(OC(=O)CCCCCCCC(=O)OC(CC)CCCCCCCC)cc4)CC3)CC2)cc1]

Lipid 9

1-nonyl 9-(4-(2-oxo-2-(2-(1-(2-((2-(4-(2-(2-(4-((9-oxo-9-(undecan-3-yloxy)nonayl)oxy)phenyl)acetoxy)ethyl)piperidin-1-yl)ethyl)disulfaneyl)ethyl)piperidin-4-yl)ethoxy)ethyl)phenyl) nonanediote

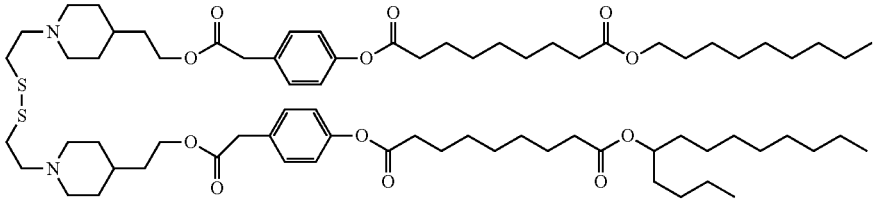 [SMILES: CCCCCCCCCOC(=O)CCCCCCCC(=O)Oc1ccc(CC(=O)OCCC2CCN(CCSSCCN3CCC(CCOC(=O)Cc4ccc(OC(=O)CCCCCCCC(=O)OC(CCCC)CCCCCCCC)cc4)CC3)CC2)cc1]

Lipid 10

1-nonyl 9-(4-(2-oxo-2-(2-(1-(2-((2-(4-(2-(2-(4-((9-oxo-9-(tridecan-5-yloxy)nonanoyl)oxy)phenyl)acetoxy)ethyl)piperidin-1-yl)ethyl)disulfaneyl)ethyl)piperidin-4-yl)ethoxy)ethyl)phenyl) nonanedioate TABLE 3-continued Exemplary ionizable lipids of the disclosure

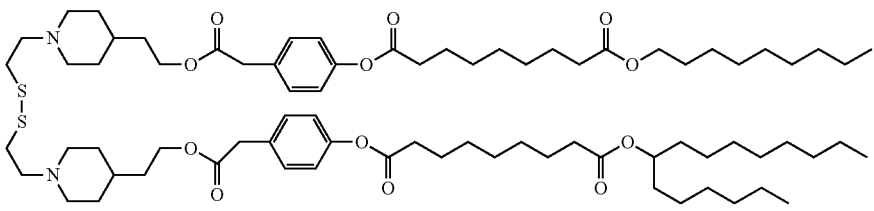 [SMILES: CCCCCCCCCOC(=O)CCCCCCCC(=O)Oc1ccc(CC(=O)OCCC2CCN(CCSSCCN3CCC(CCOC(=O)Cc4ccc(OC(=O)CCCCCCCC(=O)OC(CCCCCC)CCCCCCCC)cc4)CC3)CC2)cc1]

Lipid 11

1-nonyl 9-(4-(2-oxo-2-(2-(1-(2-((2-(4-(2-(2-(4-((9-oxo-9-(pentadecan-7-yloxy)nonanoyl)oxy)phenyl)acetoxy)ethyl)piperidin-1-yl)ethyl)disulfaneyl)ethyl)piperidin-4-yl)ethoxy)ethyl)phenyl) nonanedioate

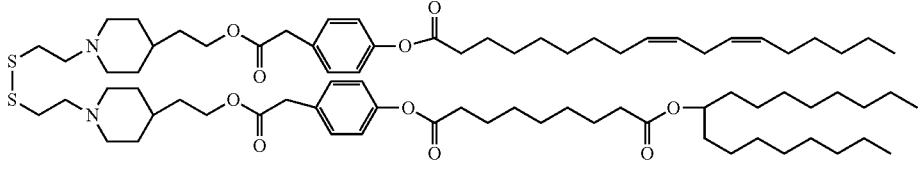 [SMILES: CCCCC/C=C\C/C=C\CCCCCCCC(=O)Oc1ccc(CC(=O)OCCC2CCN(CCSSCCN3CCC(CCOC(=O)Cc4ccc(OC(=O)CCCCCCCC(=O)OC(CCCCCCCC)CCCCCCCC)cc4)CC3)CC2)cc1]

Lipid 12

1-(heptadecan-9-yl) 9-(4-(2-(2-(1-(2-((2-(4-(2-(2-(4-(((9Z,12Z)-octadeca-9,12-dienoyl)oxy)phenyl)acetoxy)ethyl)piperidin-1-yl)ethyl)disulfaneyl)ethyl)piperidin-4-yl)ethoxy)-2-oxoethyl)phenyl) nonanediote

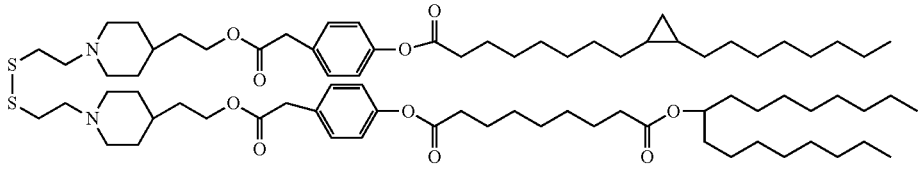 [SMILES: CCCCCCCCC(CCCCCCCC)OC(=O)CCCCCCCC(=O)Oc1ccc(CC(=O)OCCC2CCN(CCSSCCN3CCC(CCOC(=O)Cc4ccc(OC(=O)CCCCCCCC5CC5CCCCCCCC)cc4)CC3)CC2)cc1]

Lipid 13

1-(heptadecan-9-yl) 9-(4-(2-(2-(1-(2-((2-(4-(2-(2-(4-((8-(2-octylcyclopropyl)octanoyl)oxy)phenyl)acetoxy)ethyl)piperidin-1-yl)ethyl)disulfaneyl)ethyl)piperidin-4-yl)ethoxy)-2-oxoethyl)phenyl) nonanediote

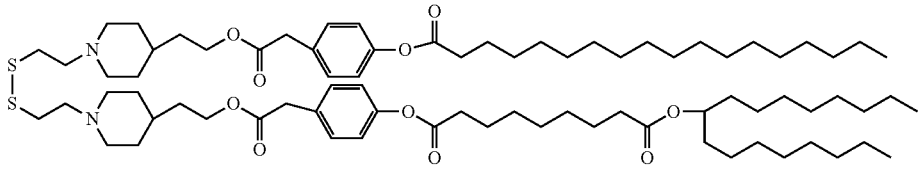 [SMILES: CCCCCCCCCCCCCCCCCC(=O)Oc1ccc(CC(=O)OCCC2CCN(CCSSCCN3CCC(CCOC(=O)Cc4ccc(OC(=O)CCCCCCCC(=O)OC(CCCCCCCC)CCCCCCCC)cc4)CC3)CC2)cc1]

Lipid 14

1-(heptadecan-9-yl) 9-(4-(2-oxo-2-(2-(1-(2-((2-(4-(2-(2-(4-(stearoyloxy)phenyl)acetoxy)ethyl)piperidin-1-yl)ethyl)disulfaneyl)ethyl)piperidin-4-yl)ethoxy)ethyl)phenyl) nonanedioate

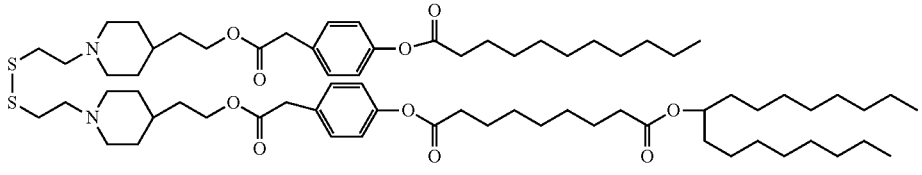 [SMILES: CCCCCCCCCCC(=O)Oc1ccc(CC(=O)OCCC2CCN(CCSSCCN3CCC(CCOC(=O)Cc4ccc(OC(=O)CCCCCCCC(=O)OC(CCCCCCCC)CCCCCCCC)cc4)CC3)CC2)cc1]

Lipid 15

1-(heptadecan-9-yl) 9-(4-(2-oxo-2-(2-(1-(2-((2-(4-(2-(2-(4-(undecanoyloxy)phenyl)acetoxy)ethyl)piperidin-1-yl)ethyl)disulfaneyl)ethyl)piperidin-4-yl)ethoxy)ethyl)phenyl) nonanedioate

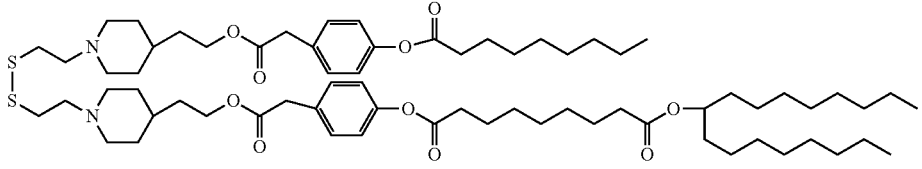 [SMILES: CCCCCCCCC(=O)Oc1ccc(CC(=O)OCCC2CCN(CCSSCCN3CCC(CCOC(=O)Cc4ccc(OC(=O)CCCCCCCC(=O)OC(CCCCCCCC)CCCCCCCC)cc4)CC3)CC2)cc1]

Lipid 16

1-(heptadecan-9-yl) 9-(4-(2-(2-(1-(2-((2-(4-(2-(2-(4-(nonanoyloxy)phenyl)acetoxy)ethyl)piperidin-1-yl)ethyl)disulfaneyl)ethyl)piperidin-4-yl)ethoxy)-2-oxoethyl)phenyl) nonanediote TABLE 3-continued Exemplary ionizable lipids of the disclosure

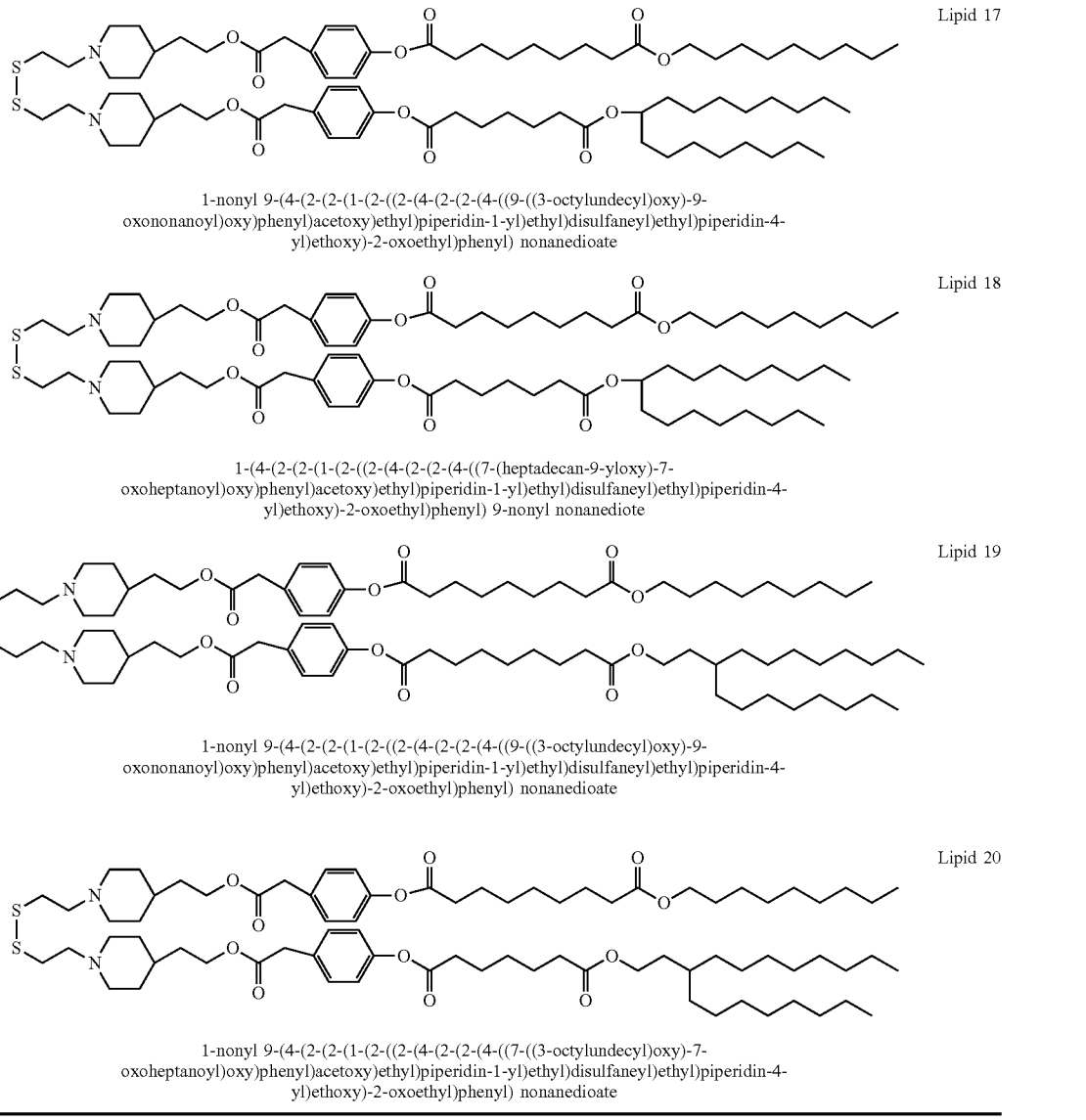

Lipid 17

1-nonyl 9-(4-(2-(2-(1-(2-((2-(4-(2-(2-(4-((9-((3-octylundecyl)oxy)-9-oxononanoyl)oxy)phenyl)acetoxy)ethyl)piperidin-1-yl)ethyl)disulfaneyl)ethyl)piperidin-4-yl)ethoxy)-2-oxoethyl)phenyl) nonanedioate Lipid 18

1-(4-(2-(2-(1-(2-((2-(4-(2-(2-(4-((7-(heptadecan-9-yloxy)-7-oxoheptanoyl)oxy)phenyl)acetoxy)ethyl)piperidin-1-yl)ethyl)disulfaneyl)ethyl)piperidin-4-yl)ethoxy)-2-oxoethyl)phenyl) 9-nonyl nonanediote Lipid 19

1-nonyl 9-(4-(2-(2-(1-(2-((2-(4-(2-(2-(4-((9-((3-octylundecyl)oxy)-9-oxononanoyl)oxy)phenyl)acetoxy)ethyl)piperidin-1-yl)ethyl)disulfaneyl)ethyl)piperidin-4-yl)ethoxy)-2-oxoethyl)phenyl) nonanedioate Lipid 20

1-nonyl 9-(4-(2-(2-(1-(2-((2-(4-(2-(2-(4-((7-((3-octylundecyl)oxy)-7-oxoheptanoyl)oxy)phenyl)acetoxy)ethyl)piperidin-1-yl)ethyl)disulfaneyl)ethyl)piperidin-4-yl)ethoxy)-2-oxoethyl)phenyl) nonanedioate or a pharmaceutically acceptable salt thereof.

20. A lipid, wherein the lipid is Lipid 7 represented by the following structure:

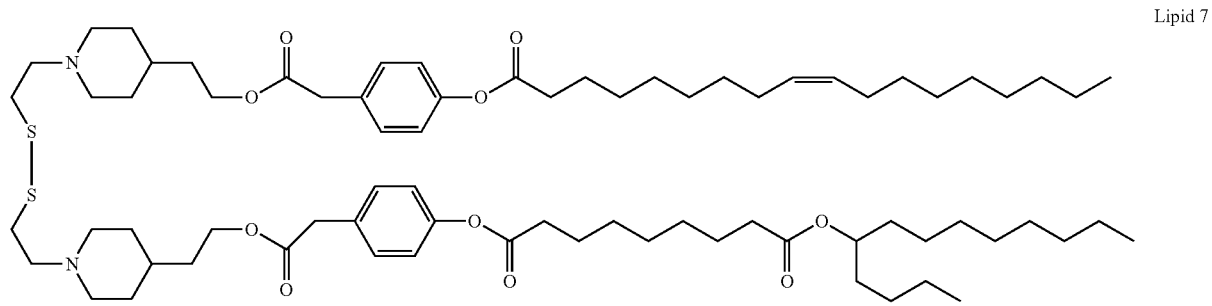 [SMILES: CCCCCCCC/C=C\CCCCCCCC(=O)Oc1ccc(CC(=O)OCCC2CCN(CCSSCCN3CCC(CCOC(=O)Cc4ccc(OC(=O)CCCCCCCC(=O)OC(CCCC)CCCCCCCC)cc4)CC3)CC2)cc1]

Lipid 7

1-(4-(2-(2-(1-(2-((2-(4-(2-(2-(4-(oleoyloxy)phenyl)acetoxy)ethyl)piperidin-1-yl)ethyl)disulfaneyl)ethyl)piperidin-4-yl)ethoxy)-2-oxoethyl)phenyl) 9-(tridecan-5-yl) nonanedioate,
or a pharmaceutically acceptable salt thereof.

* * * * *

SEQUENCE LISTING

```
Sequence total quantity: 1
SEQ ID NO: 1           moltype = DNA   length = 16
FEATURE                Location/Qualifiers
source                 1..16
                       mol_type = unassigned DNA
                       organism = Adeno associated virus 2
SEQUENCE: 1
gcgcgctcgc tcgctc                                                        16
```